(12) United States Patent
Dorich et al.

(10) Patent No.: US 12,351,578 B2
(45) Date of Patent: *Jul. 8, 2025

(54) COMPOUNDS FOR INHIBITING NLRP3 AND USES THEREOF

(71) Applicant: Ventus Therapeutics U.S., Inc., Waltham, MA (US)

(72) Inventors: Stéphane Dorich, Pointe-Claire (CA); Miguel St-Onge, Saint-Lazare (CA)

(73) Assignee: Ventus Therapeutics U.S., Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/974,342

(22) Filed: Oct. 26, 2022

(65) Prior Publication Data

US 2023/0159526 A1 May 25, 2023

Related U.S. Application Data

(63) Continuation of application No. 17/679,898, filed on Feb. 24, 2022, which is a continuation of application No. 17/528,928, filed on Nov. 17, 2021, now Pat. No. 11,319,319.

(60) Provisional application No. 63/171,932, filed on Apr. 7, 2021.

(51) Int. Cl.
| | |
|---|---|
| *C07D 471/04* | (2006.01) |
| *A61K 31/501* | (2006.01) |
| *A61K 31/502* | (2006.01) |
| *A61K 31/5025* | (2006.01) |
| *A61K 31/5377* | (2006.01) |
| *C07D 405/12* | (2006.01) |
| *C07D 491/048* | (2006.01) |
| *C07D 495/04* | (2006.01) |
| *C07D 519/00* | (2006.01) |

(52) U.S. Cl.
CPC .......... *C07D 471/04* (2013.01); *A61K 31/501* (2013.01); *A61K 31/502* (2013.01); *A61K 31/5025* (2013.01); *A61K 31/5377* (2013.01); *C07D 405/12* (2013.01); *C07D 491/048* (2013.01); *C07D 495/04* (2013.01); *C07D 519/00* (2013.01)

(58) Field of Classification Search
CPC .................................................... C07D 471/04
USPC .................................................... 514/248
See application file for complete search history.

(56) References Cited

U.S. PATENT DOCUMENTS

| | | |
|---|---|---|
| 3,753,988 A | 8/1973 | Rodway et al. |
| 4,522,811 A | 6/1985 | Eppstein et al. |
| 5,089,494 A | 2/1992 | Iwase et al. |
| 5,324,727 A | 6/1994 | Iwase et al. |
| 5,565,472 A | 10/1996 | Hamanaka |
| 5,621,027 A | 4/1997 | Roschger et al. |
| 5,763,263 A | 6/1998 | Dehlinger |
| 5,849,741 A | 12/1998 | Watanabe et al. |
| 6,114,530 A | 9/2000 | Yuan et al. |
| 6,218,392 B1 | 4/2001 | Watanabe et al. |
| 6,288,064 B1 | 9/2001 | Watanabe et al. |
| 6,316,438 B1 | 11/2001 | Yu et al. |
| 6,353,103 B1 | 3/2002 | Yuan et al. |
| 6,486,158 B1 | 11/2002 | Wang et al. |
| 6,858,624 B2 | 2/2005 | Hagen et al. |
| 7,087,621 B2 | 8/2006 | Sang et al. |
| 7,560,551 B2 | 7/2009 | Cee et al. |
| 7,666,898 B2 | 2/2010 | Chang et al. |
| 7,790,882 B2 | 9/2010 | Carreira |
| 8,067,608 B2 | 11/2011 | Beachy et al. |
| 8,106,066 B2 | 1/2012 | Schumacher et al. |
| 8,318,793 B2 | 11/2012 | Turner et al. |
| 8,329,698 B2 | 12/2012 | Cravo et al. |
| 8,338,591 B2 | 12/2012 | Yoon et al. |
| 8,445,473 B2 | 5/2013 | Wang et al. |
| 8,575,183 B2 | 11/2013 | Cushing et al. |
| 8,642,660 B2 | 2/2014 | Goldfarb |
| 8,658,801 B2 | 2/2014 | Loiseleur et al. |
| 8,674,097 B2 | 3/2014 | Cravo et al. |
| 8,791,113 B2 | 7/2014 | Dorsch et al. |
| 8,846,673 B2 | 9/2014 | Duan et al. |

(Continued)

FOREIGN PATENT DOCUMENTS

| | | |
|---|---|---|
| CL | 202203510 | 7/2023 |
| CL | 202302956 | 3/2024 |

(Continued)

OTHER PUBLICATIONS

Database Registry No. RN30181-95-4, "1-Phthalazinamine, N-[2-(4-morpholinyl)ethyl]-4-phenyl-" (CA Index Name). STN, Chemical Abstracts Service; entered Nov. 16, 1984; 1 printed page.

Database Registry No. RN296248-99-2, "4-Piperidinol, 1-[3-ethyl-9-[[2-(4-morpholinyl)ethyl]amino]-3Hpyrazolo [4',3':5,6]pyrido[3,4-d]pyridazin-6-yl]-" (CA Index Name). STN, Chemical Abstracts Service; entered Oct. 17, 2000; 1 printed page.

Database Registry No. RN1340993-30-7, "1-Phthalazinamine, N-[2-(4-morpholinyl)ethyl]-4-(3-phenyl-1,2,4-oxadiazol-5-yl)-" (CA Index Name). STN, Chemical Abstracts Service; entered Nov. 4, 2011; 1 printed page.

(Continued)

*Primary Examiner* — Niloofar Rahmani
(74) *Attorney, Agent, or Firm* — Elizabeth A. Dingess-Hammond; Leon Y. Lum

(57) ABSTRACT

The present disclosure relates to inhibitors of NLRP3 useful in the treatment of diseases and disorders inhibited by said protein and having the Formula (I):

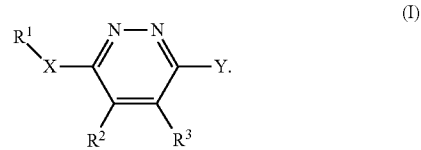

20 Claims, No Drawings

(56) References Cited

U.S. PATENT DOCUMENTS

| | | |
|---|---|---|
| 8,895,587 B2 | 11/2014 | Cassayre et al. |
| 8,912,202 B2 | 12/2014 | Staehle et al. |
| 8,932,557 B2 | 1/2015 | Chen et al. |
| 8,940,724 B2 | 1/2015 | Cushing et al. |
| 8,980,929 B2 | 3/2015 | Hicks et al. |
| 8,981,087 B2 | 3/2015 | Shuttleworth et al. |
| 9,023,490 B2 | 5/2015 | Che |
| 9,198,907 B2 | 12/2015 | Lahser et al. |
| 9,266,855 B2 | 2/2016 | Turner et al. |
| 9,309,231 B2 | 4/2016 | Zhang et al. |
| 9,458,168 B2 | 10/2016 | Trzupek et al. |
| 9,481,672 B2 | 11/2016 | Fürstner et al. |
| 9,593,108 B2 | 3/2017 | Maccoss et al. |
| 9,598,417 B2 | 3/2017 | Haßfeld et al. |
| 9,617,279 B1 | 4/2017 | Zhang |
| 9,675,073 B2 | 6/2017 | Rawal et al. |
| 9,765,039 B2 | 9/2017 | Fairfax et al. |
| 9,879,022 B2 | 1/2018 | Trzupek et al. |
| 9,949,977 B2 | 4/2018 | Fürstner et al. |
| 9,949,978 B2 | 4/2018 | Fürstner et al. |
| 10,167,294 B2 | 1/2019 | Mohan et al. |
| 10,287,284 B2 | 5/2019 | Mjalli et al. |
| 10,300,062 B2 | 5/2019 | Fürstner et al. |
| 10,519,146 B2 | 12/2019 | Lanman et al. |
| 10,717,734 B2 | 7/2020 | Findlay et al. |
| 10,736,897 B2 | 8/2020 | Li et al. |
| 10,793,577 B2 | 10/2020 | Mohan et al. |
| 10,857,123 B2 | 12/2020 | Hacini-Rachinel |
| 10,874,672 B2 | 12/2020 | Babu et al. |
| 11,254,653 B2 | 2/2022 | Farady et al. |
| 11,319,319 B1 * | 5/2022 | Dorich .................. A61P 25/00 |
| 11,851,422 B2 | 12/2023 | Vandyck et al. |
| 2003/0124053 A1 | 7/2003 | Barrett et al. |
| 2004/0242886 A1 | 12/2004 | Gupta et al. |
| 2006/0156485 A1 | 7/2006 | Lim |
| 2006/0276505 A1 | 12/2006 | Nelson et al. |
| 2007/0179123 A1 | 8/2007 | Chiang et al. |
| 2009/0082358 A1 | 3/2009 | Nishimura et al. |
| 2009/0105266 A1 | 4/2009 | Glatthar et al. |
| 2009/0124624 A1 | 5/2009 | Augereau et al. |
| 2009/0239896 A1 | 9/2009 | Chang et al. |
| 2009/0318476 A1 | 12/2009 | Ramtohul |
| 2011/0124661 A1 | 5/2011 | Brnardic et al. |
| 2011/0150833 A1 | 6/2011 | Feng et al. |
| 2011/0152246 A1 | 6/2011 | Buckman et al. |
| 2011/0160187 A1 | 6/2011 | Yoon et al. |
| 2011/0178117 A1 | 7/2011 | Converso et al. |
| 2011/0218211 A1 | 9/2011 | Bergeron et al. |
| 2012/0030841 A1 | 2/2012 | Koerber et al. |
| 2013/0079342 A1 | 3/2013 | Dransfield et al. |
| 2013/0165440 A1 | 6/2013 | Anand et al. |
| 2014/0107151 A1 | 4/2014 | Goldstein et al. |
| 2014/0194480 A1 | 7/2014 | Hoppe et al. |
| 2016/0194320 A1 | 7/2016 | Turner et al. |
| 2016/0237059 A1 | 8/2016 | Straub et al. |
| 2018/0093956 A1 | 4/2018 | Dai et al. |
| 2018/0215731 A1 | 8/2018 | Crew et al. |
| 2020/0055865 A1 | 2/2020 | Kim et al. |
| 2020/0061063 A1 | 2/2020 | Fürstner et al. |
| 2020/0075870 A1 | 3/2020 | Boudreault et al. |
| 2020/0123133 A1 | 4/2020 | No et al. |
| 2020/0207720 A1 | 7/2020 | Tanzer et al. |
| 2020/0266360 A1 | 8/2020 | Jeon et al. |
| 2020/0361898 A1 | 11/2020 | Farady et al. |
| 2021/0009577 A1 | 1/2021 | Lanman et al. |
| 2021/0130359 A1 | 5/2021 | Cooper et al. |
| 2021/0221808 A1 | 7/2021 | Chen et al. |
| 2022/0340567 A1 | 10/2022 | Dorich et al. |
| 2023/0159526 A1 | 5/2023 | Dorich et al. |
| 2023/0212152 A1 | 7/2023 | Arnold et al. |
| 2023/0303559 A1 | 9/2023 | Dorich et al. |
| 2024/0158396 A1 | 5/2024 | Dorich et al. |
| 2024/0174668 A1 | 5/2024 | Dorich et al. |
| 2024/0199606 A1 | 6/2024 | Dorich et al. |
| 2024/0239808 A1 | 7/2024 | Berry et al. |

FOREIGN PATENT DOCUMENTS

| | | |
|---|---|---|
| CL | 202400067 | 8/2024 |
| CN | 1984904 A | 6/2007 |
| CN | 103992311 A | 8/2014 |
| CN | 108697709 A | 10/2018 |
| CN | 110563722 A | 12/2019 |
| CN | 111093773 A | 5/2020 |
| CN | 202011562172.X | 12/2020 |
| CN | 202110090687.2 | 1/2021 |
| CN | 202110172665.0 | 2/2021 |
| CN | 202110592769.7 | 5/2021 |
| CN | 202110629439.0 | 6/2021 |
| CN | 202110791592.3 | 7/2021 |
| CN | 202110843496.9 | 7/2021 |
| CN | 202110940013.7 | 8/2021 |
| CN | 202110940018.X | 8/2021 |
| CN | 202210015181.X | 1/2022 |
| CN | 202210015699.3 | 1/2022 |
| CN | 115417856 A | 12/2022 |
| CN | 116726020 A | 9/2023 |
| CN | 116789674 | 9/2023 |
| CN | 116969920 A | 10/2023 |
| CN | 118056822 A | 5/2024 |
| EP | 0449203 A1 | 10/1991 |
| EP | 0623112 A1 | 11/1994 |
| EP | 0683212 A1 | 11/1995 |
| EP | 0722936 A1 | 7/1996 |
| EP | 1451202 A1 | 9/2004 |
| EP | 1984353 A1 | 10/2008 |
| EP | 1984354 A1 | 10/2008 |
| EP | 2285786 A1 | 2/2011 |
| EP | 2411379 A1 | 2/2012 |
| EP | 2445886 A1 | 5/2012 |
| EP | 2459543 A1 | 6/2012 |
| EP | 2571876 A1 | 3/2013 |
| EP | 2585461 A1 | 5/2013 |
| EP | 2621914 A1 | 8/2013 |
| EP | 2709983 A1 | 3/2014 |
| EP | 2742029 A1 | 6/2014 |
| EP | 2847190 A1 | 3/2015 |
| EP | 2852572 A1 | 4/2015 |
| EP | 2880030 A1 | 6/2015 |
| EP | 3045456 A1 | 7/2016 |
| EP | 3066100 A1 | 9/2016 |
| EP | 3126330 A1 | 2/2017 |
| EP | 3237419 A1 | 11/2017 |
| EP | 3536685 A1 | 9/2019 |
| EP | 3553049 A1 | 10/2019 |
| EP | 3604298 A1 | 2/2020 |
| EP | 3613751 A1 | 2/2020 |
| GB | 1303061 A | 1/1973 |
| GB | 2063249 A | 6/1981 |
| HK | 20098858 | 4/2024 |
| JP | H03284669 A | 12/1991 |
| JP | H06135938 A | 5/1994 |
| JP | 2009120486 A | 6/2009 |
| WO | 1989011279 A1 | 11/1989 |
| WO | 1993015058 A1 | 8/1993 |
| WO | 1996005176 A1 | 2/1996 |
| WO | 1998007430 A1 | 2/1998 |
| WO | 2000056719 A1 | 9/2000 |
| WO | 2003045967 A1 | 6/2003 |
| WO | 2004099158 A1 | 11/2004 |
| WO | 2005016000 A1 | 2/2005 |
| WO | 2005033288 A2 | 4/2005 |
| WO | 2006004589 A1 | 1/2006 |
| WO | 2006090273 A2 | 8/2006 |
| WO | 2006110516 A1 | 10/2006 |
| WO | 2007038367 A1 | 4/2007 |
| WO | 2007056184 A2 | 5/2007 |
| WO | 2007056580 A2 | 5/2007 |
| WO | 2007087276 A1 | 8/2007 |
| WO | 2007093402 A1 | 8/2007 |
| WO | 2008017161 A1 | 2/2008 |
| WO | 2008128968 A1 | 10/2008 |
| WO | 2008137084 A2 | 11/2008 |
| WO | 2009035568 A1 | 3/2009 |

(56) References Cited

FOREIGN PATENT DOCUMENTS

| | | |
|---|---|---|
| WO | 2009038812 A1 | 3/2009 |
| WO | 2009079008 A1 | 6/2009 |
| WO | 2009086303 A2 | 7/2009 |
| WO | 2009126947 A2 | 10/2009 |
| WO | 2009140163 A1 | 11/2009 |
| WO | 2009152909 A1 | 12/2009 |
| WO | 2009157386 A1 | 12/2009 |
| WO | 2010021934 A2 | 2/2010 |
| WO | 2010036544 A1 | 4/2010 |
| WO | 2010101949 A1 | 9/2010 |
| WO | 2010109005 A1 | 9/2010 |
| WO | 2010112545 A1 | 10/2010 |
| WO | 2010117935 A1 | 10/2010 |
| WO | 2010117936 A1 | 10/2010 |
| WO | 2010151791 A1 | 12/2010 |
| WO | 2011012883 A1 | 2/2011 |
| WO | 2011019780 A1 | 2/2011 |
| WO | 2011075607 A1 | 6/2011 |
| WO | 2011123751 A2 | 10/2011 |
| WO | 2011146358 A1 | 11/2011 |
| WO | 2012000595 A1 | 1/2012 |
| WO | 2012003264 A1 | 1/2012 |
| WO | 2012037132 A1 | 3/2012 |
| WO | 2012041814 A1 | 4/2012 |
| WO | 2012156400 A1 | 11/2012 |
| WO | 2012158810 A1 | 11/2012 |
| WO | 2013020622 A1 | 2/2013 |
| WO | 2013026939 A1 | 2/2013 |
| WO | 2013078254 A1 | 5/2013 |
| WO | 2013167495 A1 | 11/2013 |
| WO | 2013176698 A1 | 11/2013 |
| WO | 2014019344 A1 | 2/2014 |
| WO | 2014079935 A1 | 5/2014 |
| WO | 2014079941 A1 | 5/2014 |
| WO | 2014080291 A2 | 5/2014 |
| WO | 2014086737 A1 | 6/2014 |
| WO | 2014131315 A1 | 9/2014 |
| WO | 2015001348 A1 | 1/2015 |
| WO | 2015036560 A1 | 3/2015 |
| WO | 2015067549 A1 | 5/2015 |
| WO | 2015150995 A1 | 10/2015 |
| WO | 2016086200 A1 | 6/2016 |
| WO | 2016103037 A1 | 6/2016 |
| WO | 2016131098 A1 | 8/2016 |
| WO | 2017136871 A1 | 8/2017 |
| WO | 2017140778 A1 | 8/2017 |
| WO | 2017144341 A1 | 8/2017 |
| WO | 2017184604 A1 | 10/2017 |
| WO | 2017184623 A1 | 10/2017 |
| WO | 2017184624 A1 | 10/2017 |
| WO | 2018015445 A1 | 1/2018 |
| WO | 2018031680 A1 | 2/2018 |
| WO | 2018080216 A1 | 5/2018 |
| WO | 2018138050 A1 | 8/2018 |
| WO | 2018144649 A1 | 8/2018 |
| WO | 2018172925 A1 | 9/2018 |
| WO | 2018174678 A1 | 9/2018 |
| WO | 2018217651 A1 | 11/2018 |
| WO | 2018218071 A1 | 11/2018 |
| WO | 2018221433 A1 | 12/2018 |
| WO | 2019017741 A1 | 1/2019 |
| WO | 2019038215 A1 | 2/2019 |
| WO | 2019223548 A1 | 11/2019 |
| WO | 2020021015 A1 | 1/2020 |
| WO | 2020163248 A1 | 8/2020 |
| WO | 2020234715 A1 | 11/2020 |
| WO | 2021193897 A1 | 9/2021 |
| WO | 2021239885 A1 | 12/2021 |
| WO | 2022135567 A1 | 6/2022 |
| WO | 2022166890 A1 | 8/2022 |
| WO | 2022216971 A1 | 10/2022 |
| WO | 2022229315 A1 | 11/2022 |
| WO | 2022230912 A1 | 11/2022 |
| WO | 2022238347 A1 | 11/2022 |
| WO | 2022253326 A1 | 12/2022 |
| WO | 2022253936 A1 | 12/2022 |
| WO | 2023003002 A1 | 1/2023 |
| WO | 2023275366 A1 | 1/2023 |
| WO | 2023278438 A1 | 1/2023 |
| WO | 2023/026222 | 3/2023 |
| WO | 2023/028534 | 3/2023 |
| WO | 2023/028536 | 3/2023 |
| WO | 2023088856 A1 | 5/2023 |
| WO | 2023088987 A1 | 5/2023 |
| WO | 2023129987 A1 | 7/2023 |
| WO | 2023131277 A1 | 7/2023 |
| WO | 2023178099 A1 | 9/2023 |
| WO | 2023183943 A1 | 9/2023 |
| WO | 2023186020 A1 | 10/2023 |
| WO | 2023194964 A1 | 10/2023 |
| WO | 2023220408 A1 | 11/2023 |
| WO | 2023232917 A1 | 12/2023 |
| WO | 2024/013395 A1 | 1/2024 |
| WO | 2024006559 A1 | 1/2024 |
| WO | 2024012551 A1 | 1/2024 |
| WO | 2024017924 A1 | 1/2024 |
| WO | 2024023266 A1 | 2/2024 |
| WO | 2024028782 A1 | 2/2024 |
| WO | 2024033845 A1 | 2/2024 |
| WO | 2024041460 A1 | 2/2024 |
| WO | 2024064245 | 3/2024 |
| WO | 2024090469 A1 | 5/2024 |
| WO | 2024094150 A1 | 5/2024 |
| WO | 2024094185 A1 | 5/2024 |
| WO | 2024097598 A1 | 5/2024 |
| WO | 2024099992 A1 | 5/2024 |
| WO | 2024099993 A1 | 5/2024 |
| WO | 2024099996 A1 | 5/2024 |
| WO | 2024109922 A1 | 5/2024 |
| WO | 2024121086 | 6/2024 |
| WO | 2024121184 | 6/2024 |
| WO | 2024137319 A1 | 6/2024 |
| WO | 2024138045 A1 | 6/2024 |
| WO | 2024140704 | 7/2024 |
| WO | 2024140824 | 7/2024 |
| WO | 2024141535 A1 | 7/2024 |
| WO | 2024145623 A1 | 7/2024 |
| WO | 2024148029 A2 | 7/2024 |

OTHER PUBLICATIONS

Database Registry No. RN1340906-77-5, "1-Phthalazinamine, 4-(3-cyclopropyl-1,2,4-oxadiazol-5-yl)-N-[2-(4-morpholinyl)ethyl]-" (CA Index Name). STN, Chemical Abstracts Service; entered Nov. 4, 2011; 1 printed page.

Database Registry No. RN1340893-35-7, "1-Phthalazinamine, 4-[3-(4-fluorophenyl)-1,2,4-oxadiazol-5-yl]-N-[2-(4-morpholinyl)ethyl]-" (CA Index Name). STN, Chemical Abstracts Service; entered Nov. 4, 2011; 1 printed page.

Database Registry No. RN1217112-04-3, "1-Phthalazinamine, 4-(4-methylphenyl)-N-[2-(4-morpholinyl)ethyl]-, ethanedioate (1:2) (CA Index Name). STN, Chemical Abstracts Service; entered Apr. 6, 2010; 1 printed page."

Database Registry No. RN1135019-11-2, "1-Phthalazinamine, 4-(3,4-dimethylphenyl)-N-[2-(4-morpholinyl)ethyl]-, ethanedioate (1:2)" (CA Index Name). STN, Chemical Abstracts Service; entered Apr. 15, 2009; 1 printed page.

Database Registry No. RN1090983-56-4, "1-Phthalazinamine, 4-(4-fluorophenyl)-N-[2-(4-methoxyphenyl)-2-(4-morpholinyl)ethyl]-" (CA Index Name). STN, Chemical Abstracts Service; entered Dec. 28, 2008; 1 printed page.

Database Registry No. RN1090015-30-7, "1-Phthalazinamine, 4-(4-fluorophenyl)-N-[2-methyl-2-(4-morpholinyl)propyl]-" (CA Index Name). STN, Chemical Abstracts Service; entered Dec. 25, 2008; 1 printed page.

Database Registry No. RN1078602-84-2, "1-Phthalazinamine, N-[2-(4-morpholinyl)ethyl]-4-phenyl-, ethanedioate (1:1)" (CA Index Name). STN, Chemical Abstracts Service; entered Dec. 2, 2008; 1 printed page.

Database Registry No. RN1002033-19-3, "1-Phthalazinamine, 4-(4-methylphenyl)-N-[2-(4-morpholinyl)ethyl]-" (CA Index Name). STN, Chemical Abstracts Service; entered Feb. 7, 2008; 1 printed page.

(56) References Cited

OTHER PUBLICATIONS

Database Registry No. RN 1027552-60-8, "Pyrido[3,4-d]pyridazin-4-amine, 7-(3-methyl-2-pyridinyl)-1-[4-(trifluoromethyl)phenyl]-" (CA Index Name). STN, Chemical Abstracts Service; entered Jun. 12, 2008; 3 printed page.
Database Registry No. RN 1018166-04-5, "3-Pyridazinamine, 6-(4-bromophenyl)-N-[(tetrahydro-2-furanyl)methyl]-" (CA Index Name). STN, Chemical Abstracts Service; entered Apr. 29, 2008; 1 printed page.
Cheung et al. (2018) "Discovery of small molecule splicing modulators of survival motor neuron-2 (SMN2) for the treatment of spinal muscular atrophy (SMA)". Journal of Medicinal Chemistry, 61: 11021-11036.
Kakeya et al., "Studies on Prodrugs of Cephalosporins. I. Synthesis and Biological Properties of Glycyloxybenzoyloxymethyl and Glycylaminobenzoyloxymethyl Esters of 7?-[2-(2-Aminothiazol-4-yl)-(Z)-2-methoxyiminoacetamido]-3-methyl-3-cephem-4-carboxylic Acid", Chem. Pharm. Bull., 1984, vol. 32, pp. 692-698.
Higuchi et al., "Pro-Drugs as Novel Delivery Systems", A.C.S. Symposium Series, Sep. 1974, vol. 14, pp. 1-245.
Cahn et al., "The Specification of Asymmetric Configuration in Organic Chemistry", Experientia, 1956, vol. 12, pp. 81-94.
Cahn et al., "Specification of Molecular Chirality", Angew. Chem. Inter. Edit., 1966, vol. 5, No. 4, pp. 385-415; errata 511.
Cahn et al., "Specification of Configuration about Quadricovalent Asymmetric Atoms", J. Chem. Soc., Jan. 1951, pp. 612-622.
Bundgaard, H., "Means to Enhance Penetration", Advanced Drug Delivery Reviews, 1992, vol. 8, pp. 1-38.
Bundgaard, H., "Chapter 5: Design and Application of Pro-drugs", Drug Design and Development, 1991, pp. 113-191.
Cahn et al., "Specification of molecular chirality", Angew. Chem., 1966, vol. 78, pp. 413-447.
Widder et al., Methods in Enzymology, 1985, vol. 112, pp. 309-396.
Smith et al., "Chapter 4: Stereochemistry", March's Advanced Organic Chemistry, 2001, 5th Edition, pp. 125-217.
Alikhan et al., Hidradenitis suppurativa: a comprehensive review. J Am Acad Dermatol. Apr. 2009, 60(4):539-561; quiz 562-563. doi: 10.1016/j.jaad.2008.11.911.
Allen et al. The NLRP3 inflammasome functions as a negative regulator of tumorigenesis during colitis-associated cancer. J Exp Med. May 10, 2010;207(5):1045-56. doi: 10.1084/jem.20100050. Epub Apr. 12, 2010.
Artlett et al. The inflammasome activating caspase 1 mediates fibrosis and myofibroblast differentiation in systemic sclerosis. Arthritis Rheum. Nov. 2011;63(11):3563-74. doi: 10.1002/art.30568.
Baldwin et al. Inhibiting the Inflammasome: A Chemical Perspective. J Med Chem. Mar. 10, 2016;59(5):1691-710. doi: 10.1021/acs.jmedchem.5b01091.
Basiorka et al. The NLRP3 inflammasome functions as a driver of the myelodysplastic syndrome phenotype. Blood. Dec. 22, 2016; 128(25):2960-2975. doi: 10.1182/blood-2016-07-730556. Epub Oct. 13, 2016.
Braddock et al. Targeting IL-1 in inflammatory disease: new opportunities for therapeutic intervention. Nat Rev Drug Discov. Apr. 2004;3(4):330-9. doi: 10.1038/nrd1342.
Coll et al. A small-molecule inhibitor of the NLRP3 inflammasome for the treatment of inflammatory diseases. Nat Med. Mar. 2015;21(3):248-55. doi: 10.1038/nm.3806. Epub Feb. 16, 2015.
Cook et al., The NLRP3 inflammasome, a target for therapy in diverse disease states. Eur J Immunol. Mar. 2010;40 (3):631-634. doi: 10.1002/eji.200940162.
Database Registry No. RN 1018067-04-3, "3-Pyridazinamine, 6-(4-chlorophenyl)-N-[(tetrahydro-2-furanyl)methyl]-" (CA Index Name). STN, Chemical Abstracts Service; entered Apr. 29, 2008; 1 printed page.
De Nardo et al. New insights into mechanisms controlling the NLRP3 inflammasome and its role in lung disease. Am J Pathol. Jan. 2014;184(1):42-54. doi: 10.1016/j.ajpath.2013.09.007. Epub Oct. 30, 2013.

Dempsey et al. Inhibiting the NLRP3 inflammasome with MCC950 promotes non-phlogistic clearance of amyloid-? and cognitive function in APP/PS1 mice. Brain Behav Immun. Mar. 2017;61:306-316. doi: 10.1016/j.bbi.2016.12.014. Epub Dec. 18, 2016.
Dolunay et al. Inhibition of NLRP3 Inflammasome Prevents LPS-Induced Inflammatory Hyperalgesia in Mice: Contribution of NF-? B, Caspase-1/11, ASC, NOX, and NOS Isoforms. Inflammation. Apr. 2017,40(2):366-386. doi: 10.1007/s10753-016-0483-3.
Doyle et al. NLRP3 has a protective role in age-related macular degeneration through the induction of IL-18 by drusen components. Nat Med. May 2012;18(5):791-8. doi: 10.1038/nm.2717.
Duewell et al. NLRP3 inflammasomes are required for atherogenesis and activated by cholesterol crystals. Nature. Apr. 29, 2010;464(7293):1357-61. doi: 10.1038/nature08938. Erratum in: Nature. Jul. 29, 2010;466(7306):652.
Fang et al. Increased expression of NLRP3 inflammasome components and interleukin-18 in patients with bullous pemphigoid. J Dermatol Sci. Aug. 2016;83(2):116-23. doi: 10.1016/j.jdermsci.2016.04.009. Epub Apr. 29, 2016.
Feng et al., The role of NLRP3 inflammasome in 5-fluorouracil resistance of oral squamous cell carcinoma. J Exp Clin Cancer Res. Jun. 21, 2017;36(1):81. doi: 10.1186/s13046-017-0553-x.
Granata et al., NLRP3 inflammasome activation in dialyzed chronic kidney disease patients. PLoS One. Mar. 23, 2015;10(3):e0122272. doi: 10.1371/journal.pone.0122272.
Gugliandolo et al. NLRP3 Inflammasome Activation in a Transgenic Amyotrophic Lateral Sclerosis Model. Inflammation. Feb. 2018;41(1):93-103. doi: 10.1007/s10753-017-0667-5.
Henao-Meija et al. Inflammasome-mediated dysbiosis regulates progression of NAFLD and obesity. Nature. Feb. 1, 2012;482(7384):179-85. doi: 10.1038/nature 10809.
Hu et al. ATM is down-regulated by N-Myc-regulated microRNA-421. Proc Natl Acad Sci U S A. Jan. 26, 2010;107(4):1506-11. doi: 10.1073/pnas.0907763107. Epub Jan. 4, 2010.
Huang et al., NLRP3 inflammasome activation promotes inflammation-induced carcinogenesis in head and neck squamous cell carcinoma. J Exp Clin Cancer Res. Sep. 2, 2017;36(1):116. doi: 10.1186/s13046-017-0589-y.
Iannitti et al., IL-1 receptor antagonist ameliorates inflammasome-dependent inflammation in murine and human cystic fibrosis. Nat Commun. Mar. 14, 2016;7:10791. doi: 10.1038/ncomms10791.
Inoue et al. The role of interferon-? in the treatment of multiple sclerosis and experimental autoimmune encephalomyelitis—in the perspective of inflammasomes. Immunology. May 2013;139(1):11-8. doi: 10.1111/mm.12081.
Ismael et al., MCC950, the Selective Inhibitor of Nucleotide Oligomerization Domain-Like Receptor Protein-3 Inflammasome, Protects Mice against Traumatic Brain Injury. J Neurotrauma. Jun. 1, 2018;35(11):1294-1303. doi: 10.1089/neu.2017.5344.
Jager et al., D38 Flying: Reaching New Heights in Sarcoidosis: Key Role of Nlrp3 Inflammasome Activation In Granuloma Generation of Sarcoidosis. American Journal of Respiratory and Critical Care Medicine 191 (2015): 1 page.
Jia et al. Activation of NLRP3 inflammasome in peripheral nerve contributes to paclitaxel-induced neuropathic pain. Mol Pain. Jan.-Dec. 2017; 13:1744806917719804. doi: 10.1177/1744806917719804.
Kaizerman et al. Addressing PXR liabilities of phthalazine-based hedgehog/smoothened antagonists using novel byridopyridazines. Bioorg Med Chem Lett. Aug. 1, 2010;20(15):4607-10. doi: 10.1016/j.bmcl.2010.06.006. Epub Jun. 8, 2010.
Kim et al. Role for NLRP3 Inflammasome-mediated, IL-1?-Dependent Responses in Severe, Steroid-Resistant Asthma. Am J Respir Crit Care Med. Aug. 1, 2017;196(3):283-297. doi: 10.1164/rccm.201609-18300C.
Lazaridis et al. Activation of NLRP3 Inflammasome in Inflammatory Bowel Disease: Differences Between Crohn's Disease and Ulcerative Colitis. Dig Dis Sci. Sep. 2017; 62(9):2348-2356. doi: 10.1007/s10620-017-4609-8. Epub May 18, 2017.
Li et al. (2016) Dysregulation of the NLRP3 inflammasome complex and related cytokines in patients with multiple myeloma, Hematology, 21:3, 144-151, DOI: 10.1179/1607845415Y.0000000029.

(56) References Cited

OTHER PUBLICATIONS

Li et al. Aging-related gene signature regulated by Nlrp3 predicts glioma progression. Am J Cancer Res. 2015;5 (1):442-9.
Loukovaara et al. NLRP3 inflammasome activation is associated with proliferative diabetic retinopathy. Acta Ophthalmol. Dec. 2017;95(8):803-808. doi: 10.1111/aos.13427. Epub Mar. 8, 2017.
Lu et al. Hyperactivation of the NLRP3 Inflammasome in Myeloid Cells Leads to Severe Organ Damage in Experimental Lupus. J Immunol. Feb. 1, 2017; 198(3):1119-1129; DOI: https://doi.org/10.4049/jimmunol.1600659.
Masters, Specific inflammasomes in complex diseases. Clin Immunol. Jun. 2013;147(3):223-228. doi: 10.1016/j.clim.2012.12.006.
Menu et al. The NLRP3 inflammasome in health and disease: the good, the bad and the ugly. Clin Exp Immunol. Oct. 2011; 166(1):1-15. doi: 10.1111/j.1365-2249.2011.04440.x. Epub Jul. 15, 2011.
Mridha et al., NLRP3 inflammasome blockade reduces liver inflammation and fibrosis in experimental NASH in mice. J Hepatol. May 2017;66(5):1037-1046. doi: 10.1016/j.jhep.2017.01.022.
Neudecker et al., Myeloid-derived miR-223 regulates intestinal inflammation via repression of the NLRP3 Inflammasome. J Exp Med. Jun. 5, 2017;214(6):1737-1752. doi: 10.1084/jem.20160462.
Niebuhr et al., Impaired NLRP3 inflammasome expression and function in atopic dermatitis due to Th2 milieu. Allergy. Aug. 2014;69(8):1058-1067. doi: 10.1111/all.12428.
Ozaki et al., Targeting the NLRP3 inflammasome in chronic inflammatory diseases: current perspectives. J Inflamm Res. Jan. 16, 2015;8:15-27. doi: 10.2147/JIR.S51250.
Perregaux et al.; Identification and characterization of a novel class of interleukin-1 post-translational processing inhibitors. J Pharmacol Exp Ther. Oct. 2001;299(1):187-197.
Primiano et al., Efficacy and Pharmacology of the NLRP3 Inflammasome Inhibitor CP-456,773 (CRID3) in Murine Models of Dermal and Pulmonary Inflammation. J Immunol. Sep. 15, 2016;197(6):2421-2433. doi: 10.4049/immunol.1600035.
Puyang et al., Retinal Ganglion Cell Loss is Delayed Following Optic Nerve Crush in NLRP3 Knockout Mice. Sci Rep. Feb. 19, 2016;6:20998. doi: 10.1038/srep20998.
Qin et al., Propionibacterium acnes induces IL-1? secretion via the NLRP3 inflammasome in human monocytes. J Invest Dermatol. Feb. 2014;134(2):381-388. doi: 10.1038/jid.2013.309.
Ridker et al., CANTOS Trial Group. Antiinflammatory Therapy with Canakinumab for Atherosclerotic Disease. N Engl J Med. Sep. 21, 2017;377(12):1119-1131. doi: 10.1056/NEJMoa1707914.
Ridker et al., CANTOS Trial Group. Effect of interleukin-1? inhibition with canakinumab on incident lung cancer in patients with atherosclerosis: exploratory results from a randomised, double-blind, placebo-controlled trial. Lancet. Oct. 21, 2017;390(10105):1833-1842. doi: 10.1016/S0140-6736(17)32247-X.
Sano et al., Tet2-Mediated Clonal Hematopoiesis Accelerates Heart Failure Through a Mechanism Involving the IL-1?/NLRP3 Inflammasome. J Am Coll Cardiol. Feb. 27, 2018;71(8):875-886. doi: 10.1016/j.jacc.2017.12.037.
Schroder et al., The inflammasomes. Cell. Mar. 19, 2010;140(6):821-832. doi: 10.1016/j.cell.2010.01.040.
Schroder et al., The NLRP3 inflammasome: a sensor for metabolic danger? Science. Jan. 15, 2010;327(5963):296-300. doi: 10.1126/science.1184003.
Scott et al., A randomised trial evaluating anakinra in early active rheumatoid arthritis. Clin Exp Rheumatol. Jan.-Feb. 201634(1):88-93.
Behalo et al., "Synthesis of Novel Phthalazine Derivatives as Potential Anticancer and Antioxidant Agents Based on 1-Chloro-4-(4-phenoxyphenyl)phthalazine", J Heterocyclic Chem, Sep. 2017, vol. 54, No. 6, pp. 3591-3599.
Colotta, et al., "Synthesis and structure-activity relationships of 1-aminophthalazinium salts as GABAA receptor antagonists", European Journal of Medicinal Chemistry, 1994, vol. 29, No. 2, pp. 95-105.

Johnsen et al., "New antithrombotic 1-Phthalazinamines with Serotonin Antagonistic Properties", Arch. Pharm, Dec. 2003, vol. 336, No. 12, pp. 591-597.
Sayed et al., "Synthesis and reactions of 4-aryl-1(2H) phthalazinones", Chinese Journal of Chemistry, Jan. 1991, vol. 9, No. 1, pp. 45-53.
U.S. Appl. No. 17/984,018, filed Nov. 9, 2022.
Kassab (2005). Synthesis and behaviour of 4-[4?-chloro-3?-methyl phenyl]-1 [2H]-phthalazinone towards certain electrophiles and nucleophiles. Egyptian Journal of Chemistry, 48(2), 183-199.
Database Registry No. RN1181498-12-3, "Benzamide, 4-[4-(cyclopentylamino)-1-phthalazinyl]-" (CA Index Name). STN, Chemical Abstracts Service; entered Sep. 9, 2009; 1 printed page.
Database Registry No. RN1267866-53-4, "1-Phthalazinamine, 4-(4-fluorophenyl)-N-3-pyrrolidinyl-"(CA Index Name). STN, Chemical Abstracts Service; entered Mar. 10, 2011; 1 printed page.
Database Registry No. RN1310214-26-6, "1-Phthalazinamine, 4-(4-methylphenyl)-N-3-pyrrolidinyl-"CA Index Name). STN, Chemical Abstracts Service; entered Jun. 23, 2011; 1 printed page.
Database Registry No. RN2198981-59-6, "Cyclopentanecarboxylic acid, 3-hydroxy-4-[[4-(4-methoxyphenyl)-1-phthalazinyl]amino]-" (CA Index Name). STN, Chemical Abstracts Service; Mar. 26, 2018; 1 printed page.
Database Registry No. RN447430-57-1, "1-Phthalazinamine, N-cyclohexyl-4-(3,4-dimethylphenyl)-" (CA Index Name). STN, Chemical Abstracts Service; entered Sep. 6, 2002; 1 printed page.
Database Registry No. RN447430-58-2, "1-Phthalazinamine, N-cyclohexyl-4-(4-methylphenyl)-" (CA Index Name). STN, Chemical Abstracts Service; entered Sep. 6, 2002; 1 printed page.
Database Registry No. RN447430-60-6, "1-Phthalazinamine, N-cyclohexyl-4-(2,4-dimethylphenyl)-" (CA Index Name). STN, Chemical Abstracts Service; entered Sep. 6, 2002; 1 printed page.
Database Registry No. RN447430-62-8, "1-Phthalazinamine, N-cyclohexyl-4-(2,5-dimethylphenyl)-" (CA Index Name). STN, Chemical Abstracts Service; entered Sep. 6, 2002; 1 printed page.
Database Registry No. RN447430-63-9, "1-Phthalazinamine, N-cyclohexyl-4-(4-fluorophenyl)-" (CA Index Name). STN, Chemical Abstracts Service; entered Sep. 6, 2002; 1 printed page.
Database Registry No. RN447430-65-1, "1-Phthalazinamine, 4-(4-chlorophenyl)-N-cyclohexyl-" (CA Index Name). STN, Chemical Abstracts Service; entered Sep. 6, 2002; 1 printed page.
Database Registry No. RN694474-51-6 "Phthalazine, 1-(cyclohexyloxy)-4-(4-methylphenyl)-"(CA Index Name). STN, Chemical Abstracts Service; entered Jun. 17, 2004; 1 printed page.
Database Registry No. RN852664-73-4, "1-Phthalazinamine, N-cycloheptyl-4-(4-methylphenyl)-"(CA Index Name). STN, Chemical Abstracts Service; entered Jun. 22, 2005; 1 printed page.
Database Registry No. RN1351271-90-3, "3-Pyridazinamine, N-(1-methylethyl)-6-(1,2,3,4-tetrahydro-5-isoquinolinyl)-" (CA Index Name). STN, Chemical Abstracts Service; entered Dec. 19, 2011; 1 printed page.
Database Registry No. RN1482843-77-5, "1-Naphthalenol, 2-[6-(propylamino)-3-pyridazinyl]-" (CA Index Name). STN, Chemical Abstracts Service; entered Nov. 28, 2013; 1 printed page.
Database Registry No. RN1485079-65-9, "1-Naphthalenol, 2-[6-(ethylamino)-3-pyridazinyl]-"(CA Index Name). STN, Chemical Abstracts Service; entered Dec. 2, 2013; 1 printed page.
Database Registry No. RN1488322-94-6, "1-Phthalazinamine, 4-(2-methoxyphenyl)-N-methyl-" (CA Index Name). STN, Chemical Abstracts Service; entered Dec. 5, 2013; 1 printed page.
Database Registry No. RN1494117-54-2, "1-Phthalazinamine, 4-(2-methoxy-5-methylphenyl)-N-methyl-" (CA Index Name). STN, Chemical Abstracts Service; entered Dec. 13, 2013; 1 printed page.
Database Registry No. RN1496330-00-7, "1-Phthalazinamine, 4-(5-fluoro-2-methoxyphenyl)-N-methyl-"(CA Index Name). STN, Chemical Abstracts Service; entered Dec. 16, 2013; 1 printed page.
Database Registry No. RN1562335-33-4, "2,7-Naphthalenediol, 3-[6-[(2,2,6,6-tetramethyl-4-piperidinyl)oxy]-3-pyridazinyl]-" (CA Index Name). STN, Chemical Abstracts Service; entered Mar. 4, 2014; 1 printed page.
Database Registry No. RN1562335-37-8, "2,7-Naphthalenediol, 3-[6-[(2,2,6,6-tetramethyl-4-piperidinyl)amino]-3-pyridazinyl]-" (CA Index Name). STN, Chemical Abstracts Service; entered Mar. 4, 2014; 1 printed page.

(56) References Cited

OTHER PUBLICATIONS

Database Registry No. RN1647113-18-5, "6-Isoquinolinol, 7-[6-[(2,2,6,6-tetramethyl-4-piperidinyl)oxy]-3-pyridazinyl]-"(CA Index Name). STN, Chemical Abstracts Service; entered Feb. 13, 2015; 1 printed page.
Database Registry No. RN1647113-19-6, "Isoquinoline, 6-methoxy-7-[6-[(2,2,6,6-tetramethyl-4-piperidinyl)oxy]-3-pyridazinyl]-"(CA Index Name). STN, Chemical Abstracts Service; entered Feb. 13, 2015; 1 printed page.
Database Registry No. RN1647116-09-3, "6-Isoquinolinol, 3-propyl-7-[6-[(2,2,6,6-tetramethyl-4-piperidinyl)oxy]-3-pyridazinyl]-"(CA Index Name). STN, Chemical Abstracts Service; entered Feb. 13, 2015; 1 printed page.
Database Registry No. RN1647116-10-6, "6-Isoquinolinol, 3-(1-methylethyl)-7-[6-[(2,2,6,6-tetramethyl-4-piperidinyl)oxy]-3-pyridazinyl]-"(CA Index Name). STN, Chemical Abstracts Service; entered Feb. 13, 2015; 1 printed page.
Database Registry No. RN174542-71-3, "Phthalazine, 1-(4-methoxyphenyl)-4-(4-methylphenoxy)-"(CA Index Name). STN, Chemical Abstracts Service; entered Mar. 26, 1996; 1 printed page.
Database Registry No. RN1892513-27-7, "Acetonitrile, 2-[[6-(5,6,7,8-tetrahydro-2-naphthalenyl)-3-pyridazinyl]amino]-"(CA Index Name). STN, Chemical Abstracts Service; entered Apr. 18, 2016; 1 printed page.
Database Registry No. RN1893453-26-3, "3-Pyridazinamine, N-(1-methylethyl)-6-(2-naphthalenyl)-" (CA Index Name). STN, Chemical Abstracts Service; entered Apr. 20, 2016; 1 printed page.
Database Registry No. RN2332630-59-6, Index Name Not yet Assigned. STN, Chemical Abstracts Service; entered Jun. 13, 2019; 1 printed page.
Database Registry No. RN2344192-58-9, "3-Pyridazinamine, N-pentyl-6-(5,6,7,8-tetrahydro-2-naphthalenyl)-" (CA Index Name). STN, Chemical Abstracts Service; entered Jun. 24, 2019; 1 printed page.
Database Registry No. RN361998-09-6, "1-Phthalazinamine, N-(3,4-dichlorophenyl)-4-(4-methoxyphenyl)-" (CA Index Name). STN, Chemical Abstracts Service; entered Oct. 14, 2001; 1 printed page.
Database Registry No. RN447431-24-5, "1-Phthalazinamine, N,4-bis(4-fluorophenyl)-" (CA Index Name). STN, Chemical Abstracts Service; entered Sep. 6, 2002; 1 printed page.
Database Registry No. RN487025-40-1, "Benzamide, 4-[[4-(4-hydroxyphenyl)-1-phthalazinyl]amino]-" (CA Index Name). STN, Chemical Abstracts Service; entered Feb. 7, 2003; 1 printed page.
Database Registry No. RN496027-82-8, "1-Propanone, 1-[4-[[4-(3,4-dimethylphenyl)-1-phthalazinyl]oxy]phenyl]-"(ca Index Name). STN, Chemical Abstracts Service; entered Feb. 28, 2003; 1 printed page.
Database Registry No. RN742121-05-7, "Ethanone, 1-[4-[[4-(4-methylphenyl)-1-phthalazinyl]oxy]phenyl]-"(CA Index Name). STN, Chemical Abstracts Service; entered Sep. 10, 2004; 1 printed page.
Database Registry No. RN78351-72-1, "1-Phthalazinamine, N-(4-fluorophenyl)-4-phenyl-" (CA Index Name). STN, Chemical Abstracts Service; entered Nov. 16, 1984; 1 printed page.
Database Registry No. RN78352-14-4, "1-Phthalazinamine, 4 (4-chlorophenyl)-N-[3-(trifluoromethyl) phenyl]-" (CA Index Name). STN, Chemical Abstracts Service; entered Nov. 16, 1984; 1 printed page.
Database Registry No. RN934264-83-2, "1-Phthalazinamine, 7-methoxy-4-(4-methoxyphenyl)-N-4-piperidinyl-" (CA Index Name). STN, Chemical Abstracts Service; entered May 4, 2007; 1 printed page.
International Search Report and Written Opinion for International Application No. PCT/US2022/023893, mailed Oct. 28, 2022, 17 pages.
Cahn, "An Introduction to the Sequence Rule", J. Chem. Educ., Mar. 1964, vol. 41, No. 3 pp. 116-125.
Nielsen et al., "Glycolamide esters as biolabile prodrugs of carboxylic acid agents: synthesis, stability, bioconversion, and physicochemical properties", Journal of Pharmaceutical Sciences, Apr. 1988, vol. 77, No. 4, pp. 285-298.

Database Registry No. RN930002-29-2, "1-Phthalazinamine, 4-(3,4-dimethylphenyl)-N-[2-(4-morpholinyl)ethyl]-" (CA Index Name). STN, Chemical Abstracts Service; entered Apr. 13, 2007; 1 printed page.
Database Registry No. RN852915-63-0, "1-Phthalazinamine, N-[2-methyl-2-(4-morpholinyl)propyl]-4-phenyl-" (CA Index Name). STN, Chemical Abstracts Service; entered Jun. 24, 2005; 1 printed page.
Database Registry No. RN792956-18-4, "1-Phthalazinamine, 4-(4-fluorophenyl)-N-[2-(4-morpholinyl)ethyl]-" (CA Index Name). STN, Chemical Abstracts Service; entered Dec. 6, 2004; 1 printed page.
Database Registry No. RN312591-18-7, "1-Phthalazinamine, 4-(4-chlorophenyl)-N-[2-(4-morpholinyl)ethyl]-" (CA Index Name). STN, Chemical Abstracts Service; entered Jan. 3, 2001; 1 printed page.
Strowig et al., Inflammasomes in health and disease. Nature. Jan. 18, 2012;481(7381):278-286. doi: 10.1038/nature 10759.
Tarallo et al., DICER1 loss and Alu RNA induce age-related macular degeneration via the NLRP3 inflammasome and MyD88. Cell. May 11, 2012;149(4):847-859. doi: 10.1016/j.cell.2012.03.036.
U.S. Appl. No. 17/704,983, filed Mar. 25, 2022.
Van Hout et al., The selective NLRP3-inflammasome inhibitor MCC950 reduces infarct size and preserves cardiac function in a pig model of myocardial infarction. Eur Heart J. Mar. 14, 2017;38(11):828-836. doi: 10.1093/eurheartj/ehw247.
Walsh et al., Inflammasomes in the CNS. Nat Rev Neurosci. Feb. 2014;15(2):84-97. doi: 10.1038/nrn3638.
Wang et al., Activation of NLRP3 inflammasome enhances the proliferation and migration of A549 lung cancer cells. Oncol Rep. Apr. 2016;35(4):2053-2064. doi: 10.3892/or.2016.4569.
Wen et al., A role for the NLRP3 inflammasome in metabolic diseases—did Warburg miss inflammation? Nat Immunol. Mar. 19, 2012;13(4):352-357. doi: 10.1038/ni.2228.
Wu et al., NLRP3 (Nucleotide Oligomerization Domain-Like Receptor Family, Pyrin Domain Containing 3)-Caspase-1 Inflammasome Degrades Contractile Proteins: Implications for Aortic Biomechanical Dysfunction and Aneurysm and Dissection Formation. Arterioscler Thromb Vasc Biol. Apr. 2017;37(4):694-706. doi: 10.1161/ATVBAHA.116.307648.
Zhang et al., Increased Expression of NLRP3 Inflammasome in Wall of Ruptured and Unruptured Human Cerebral Aneurysms: Preliminary Results. J Stroke Cerebrovasc Dis. May 2015;24(5):972-979. doi: 10.1016/j.istrokecerebrovasdis.2014.12.019.
Su et al., "Recent Progress on the Discovery of NLRP3 Inhibitors and their Therapeutic Potential", Current Medicinal Chemistry, 2021, vol. 28, pp. 569-582.
Li et al., "Recent Progress and Prospects of Small Molecules for NLRP3 Inflammasome Inhibition", Journal of Medicinal Chemistry, Oct. 2023, pp. 1-27.
Peukert et al., "A method for estimating the risk of drug-induced phototoxicity and its application to smoothened inhibitors", MedChemComm, Aug. 2011, vol. 2, pp. 973-976.
Lee et al., "MPTP-driven NLRP3 inflammasome activation in microglia plays a central role in dopaminergic neurodegeneration", Cell Death Differ., May 2018, vol. 26, No. 2, pp. 213-228.
Cheng et al., "Microglial autophagy defect causes Parkinson disease-like symptoms by accelerating inflammasome activation in mice," Autophagy, Jan. 2020, vol. 16, No. 12, pp. 2193-2205.
Qin et al., "Impaired autophagy in microglia aggravates dopaminergic neuro?degeneration by regulating NLRP3 inflammasome activation in experimental models of Parkinson's disease", Brain Behav. Immun., Oct. 2020, vol. 91, pp. 324-338.
Ma et al., "Prussian blue nanozyme as a pyroptosis inhibitor alleviates neurodegeneration", Adv. Mater., Mar. 2022, vol. 34, No. 15, e2106723, pp. 1-12.
Siew et al., "Galectin-3 is required for the microglia-mediated brain inflammation in a model of Huntington's disease", Nat. Commun., Aug. 2019, vol. 10, No. 1, Article No. 3473, pp. 1-18.
Paldino et al., "Pyroptotic cell death in the R6/2 mouse model of Huntington's disease: new insight on the inflammasome", Cell Death Discov., Jul. 2020, vol. 6, No. 69, pp. 1-12.

(56) References Cited

OTHER PUBLICATIONS

Gu et al., "Mitochondrial uncoupling protein 1 antagonizes atherosclerosis by blocking NLRP3 inflammasome-dependent interleukin-1beta production", Sci. Adv., Dec. 2021, vol. 7, No. 50, eabl4024, pp. 1-14.
Duewell et al., "NLRP3 inflammasomes are required for atherogenesis and activated by cholesterol crystals," Nature, Apr. 2010, vol. 464, No. 7293, pp. 1357-1361.
Wang et al., "Thioredoxin-1 attenuates atherosclerosis development through inhibiting NLRP3 inflammasome," Endocrine., Jun. 2020, vol. 70, No. 1, pp. 65-70.
Wu et al., "Nicotine promotes atherosclerosis via ROS-NLRP3-mediated endothelial cell pyroptosis," Cell Death Dis., Feb. 2018, vol. 9, No. 2, pp. 1-12.
Zeng et al., "NLRP3 inflammasome-mediated pyroptosis contributes to the pathogenesis of non-ischemic dilated cardiomyopathy," Redox Biol., Mar. 2020, vol. 34, 101523, pp. 1-13.
Byrne et al., "Empaglifozin blunts worsening cardiac dysfunction associated with reduced NLRP3 (nucleotide-binding domain-like receptor protein 3) inflammasome activation in heart failure", Circ. Heart Fail., Jan. 2020, vol. 13, No. 1, e006277 pp. 1-19.
Mridha et al., "NLRP3 inflammasome blockade reduces liver inflammation and fibrosis in experimental NASH in mice", J. Hepatol., Feb. 2017, vol. 66, No. 5, pp. 1037-1046.
Jimenez Calvente et al., "MicroRNA 223 3p negatively regulates the NLRP3 inflammasome in acute and chronic liver injury", Mol. Ther., Sep. 2019, vol. 28, No. 2, pp. 653-663.
Ma et al., "NLRP3 inflammasome activation in liver cirrhotic patients", Biochem. Biophys. Res. Commun., Sep. 2018, vol. 505, No. 1, pp. 40-44.
Chen et al., "Stem cells from human exfoliated deciduous teeth alleviate liver cirrhosis via inhibition of Gasdermin D—executed hepatocyte pyroptosis", Front. Immunol., May 2022, vol. 13, 860225, pp. 1-12.
Zhu et al., "Alpinetin exerts anti-inflammatory, anti-oxidative and anti-angio?genic effects through activating the Nrf2 pathway and inhibiting NLRP3 pathway in carbon tetrachloride-induced liver fibrosis", Int. Immunopharmacology, Apr. 2021, vol. 96, 107660, pp. 1-11.
Kim et al., "Auranofin prevents liver fibrosis by system Xc-mediated inhibition of NLRP3 inflammasome", Commun. Biol., Jun. 2021, vol. 4, No. 1, pp. 1-15.
Gaul et al., "Hepatocyte pyroptosis and release of inflammasome particles induce stellate cell activation and liver fibrosis", J. Hepatol., Aug. 2020, vol. 74, No. 1, pp. 156-167.
Ackley et al., "Metabolic Stability Assessed by Liver Microsomes and Hepatocytes", Methods in Pharmacology and Toxicology, 2004, pp. 151-162.
Alsenz et al., "High throughput solubility measurement in drug discovery and development", Advanced Drug Delivery Reviews, Jul. 2007, vol. 59, No. 7, pp. 546-567.
Kirsch et al., "Variability in the measurement of hERG potassium channel inhibition: effects of temperature and stimulus pattern", Journal of Pharmacological and Toxicological Methods, Sep. 2004, vol. 50, pp. 93-101.
Marrannes et al., "Computer programs to facilitate the estimation of time-dependent drug effects on ion channels", Computer Methods and Programs in Biomedicine, May 2004, vol. 74, No. 2, pp. 167-181.
Miller et al. "Integrating the Impact of Lipophilicity on Potency and Pharmacokinetic Parameters Enables the Use of Diverse Chemical Space during Small Molecule Drug Optimization", J. Med. Chem., Jul. 2020, vol. 63, No. 21, pp. 12156-12170.
Roche et al., "A Virtual Screening Method for Prediction of the hERG Potassium Channel Liability of Compound Libraries", ChemBioChem, May 2002, vol. 3, No. 5, pp. 455-459.
Smith et al., "Clearance in Drug Design", J. Med. Chem., Oct. 2018, vol. 62, pp. 2245-2255.
Wang et al., "Determination of in vitro permeability of drug candidates through a caco-2 cell monolayer by liquid chromatography/tandem mass spectrometry", J Mass Spectrom, Jan. 2000, vol. 25, pp. 71-76.
Co-pending U.S. Appl. No. 18/480,164, inventors Dorich; Stéphane et al., filed Oct. 3, 2023.
Co-pending U.S. Appl. No. 18/480,925, inventors Dorich; Stéphane et al., filed Oct. 4, 2023.
Epsztajn et al. "Application of organolithium and related reagents in synthesis, Part XII. Synthesis of phenyl-and pyridylpyridopyridazinones and their derivatives". Monatshefte für Chemie/Chemical Monthly (May 21, 1993) 124 (5):549-558.
PubChem CID 42507259 "2-methoxy-1-(1,3,4,5-tetrahydro-2H-pyrido[4,3-b]indol-2-yl)ethanone" Entered May 30, 2009, Modified Jan. 15, 2023, 7 pages.
Sako "Product class 18: pyridopyridazines". Science of Synthesis (2004) 16:1109-1153.
Li, H., et al.; "Therapeutic potential of MCC950, a specific inhibitor of NLRP3 inflammasome," Eur J Pharmacol. (2022); 928:175091.
Chakraborty et al. "NLRP3 inflammasome in traumatic brain injury: Its implication in the disease pathophysiology and potential as a therapeutic target" Life Sciences (2023); 314(121352):1-8.
Corcoran et al. "Pharmacological inhibition of the nod-like receptor family pyrin domain containing 3 inflammasome with MCC950" Pharmacological Reviews (2021); 73(3):968-1000.
Gaidt et al. "The NLRP3 inflammasome renders cell death pro-inflammatory" Journal of Molecular Biology (2018); 430(2):133-141.
Liu, X. et al. "Channelling inflammation: gasdermins in physiology and disease" Nature Reviews Drug Discovery (2021); 20(5):384-405.
Nguyen, L.T., et al.; "Role of NLRP3 Inflammasome in Parkinson's Disease and Therapeutic Considerations," J Parkinsons Dis. (2022); 12(7):2117-2133.
PCT/US2023/078143 International Search Report and Written Opinion dated Feb. 27, 2024, 11 pages.
Pike et al. "Dopamine signaling modulates microglial NLRP3 inflammasome activation: implications for Parkinson's disease" Journal of Neuroinflammation (2022); 19(50):1-16.
Sefik et al. "Inflammasome activation in infected macrophages drives COVID-19 pathology" Nature (2022); 606 (7914):585-593.
Sharif et al. "Structural mechanism for NEK7-licensed activation of NLRP3 inflammasome" Nature (2019); 570 (7761):338-343.
Shen, C. et al. "Molecular mechanism for NLRP6 inflammasome assembly and activation" Proceedings of the National Academy of Sciences (2019); 116(6):2052-2057.
Terrone et al. "Inflammation and reactive oxygen species in status epilepticus: Biomarkers and implications for therapy" Epilepsy & Behavior (2019); 101(106275):1-9.
Wang, C. et al. "NLRP3 inflammasome activation triggers gasdermin D-independent inflammation" Science Immunology (2021); 6(64):eabj3859, 1-12.
Xiao, L. et al. "Cryo-EM structures of the active NLRP3 inflammasome disc" Nature (2023); 613(7944):595-600.
Zahid, A., et al.; "Pharmacological Inhibitors of the NLRP3 Inflammasome," Front Immunol. (2019); 10:2538, 10 pages.
Yang et al., "Pannexin 1 channels contribute to IL-1? expression via LRP3/caspase-1 inflammasom in Aspergillus Fumigatus Keratitis," Current Eye Research, Mar. 2019, vol. 44, pp. 716-725.
Liao et al., "Retinal pigment epithelium cell death is associated with NLRP3 inflammasome activation by All-trans Retinal," Investigative Opthalmology & Visual Science, Jul. 2019, vol. 60, pp. 3034-3045.
Heneka et al., "NLRP3 is activated in Alzheimer's disease and contributes to pathology in APP/PS1 mice," Nature, Dec. 2012, vol. 493, pp. 674-678.
Cho et al., "Autophagy in microglia degrades extracellular beta-amyloid fibrils and regulates the NLRP3 inflammasome", Autophagy, Jul. 2014, vol. 10, pp. 1761-1775.
Zheng et al., "NLRP3 inflammasomes show high expression in aorta of patients with atherosclerosis," Heart, Lung and Circulation, Feb. 2013, vol. 22, No. 9, pp. 746-750.

(56) References Cited

OTHER PUBLICATIONS

Yao et al., "Enhanced cardiomyocyte NLRP3 inflammasome signaling promotes atrial fibrillation," Circulation, Nov. 2018, vol. 138, pp. 2227-2242.
Moossavi et al., "Role of the NLRP3 inflammasome in cancer," Molecular Cancer, Nov. 2018, vol. 17, No. 158, pp. 1-13.
Yan et al., "Dopamine controls systemic inflammation through inhibition of NLRP3 inflammasome", Cell, Jan. 2015, vol. 160, pp. 62-73.
Legrand-Poels et al., "Free fatty acids as modulators of the NLRP3 inflammasome in obesity/type 2 diabetes", Biochem. Pharm., Aug. 2014, vol. 92, pp. 131-141.
Haneklaus et al., "NLRP3 at the interface of metabolism and inflammation", Immunol. Rev. May 2015, vol. 265, pp. 53-62.
Yin et al., "Transcriptome analysis of human adipocytes implicates the NOD-like receptor pathway in obesity-induced adipose inflammation", Mol. Cell. Endocrinol., Jul. 2014, vol. 394, pp. 80-87.
Stienstra et al., "The inflammasome-mediated caspase-1 activation controls adipocyte differentiation and insulin sensitivity", Cell Metab., Dec. 2010, vol. 12, pp. 593-605.
Stienstra et al.,"Inflammasome is a central player in the induction of obesity and insulin resistance", Proc. Natl. Acad. Sci., Aug. 2011, vol. 108, pp. 15324-15329.
Ferreira et al., "NLRP3 Inflammasome and Mineralocorticoid Receptors Are Associated with Vascular Dysfunction in Type 2 Diabetes Mellitus", Cells, Dec. 2019, vol. 8, 1595, pp. 1-13.
Lee et al., "Upregulated NLRP3 inflammasome activation in patients with type 2 diabetes", Diabetes, Oct. 2013, vol. 62, pp. 194-204.
Sandanger et al., "The NLRP3 inflammasome is up-regulated in cardiac fibroblasts and mediates myocardial ischaemia-reperfusion injury", Cardiovasc. Res., Apr. 2013, vol. 99, pp. 164-174.
Bertoni et al., "A novel knock-in mouse model of cryopyrin-associated periodic syndromes with development of amyloidosis: therapeutic efficacy of proton pump inhibitors," J. Allergy Clin. Immunol., Jun. 2019, vol. 145, pp. 368-378 e13.
Chen et al., "The NLRP3 inflammasome: contributions to inflammation-related diseases", Cellular & Molecular Biology Letters, Jun. 2023, vol. 28, Article No. 51, pp. 1-27.
Stackowicz et al., "Neutrophil-specific gain-of-function mutations in Nlrp3 promote development of cryopyrin-associated periodic syndrome", J. Exp. Med., Sep. 2021, vol. 218, pp. 1-15.
Omenetti et al., "Increased NLRP3-dependent interleukin 1beta secretion in patients with familial Mediterranean fever: correlation with MEFV genotype", Ann Rheum Dis., Mar. 2013, vol. 73, No. 2, pp. 462-469.
Ising et al., "NLRP3 inflammasome activation drives tau pathology," Nature, Nov. 2019, vol. 575, No. 7784, pp. 669-673.
Fan et al., "Systemic activation of NLRP3 inflammasome and plasma alpha-synuclein levels are correlated with motor severity and progression in Parkinson's disease," J. Neuroinflamm., Jan. 2020, vol. 17, No. 1, pp. 1-10.
Amsler et al. The inflammasome as a target of modulation by DNA viruses. Future Virol. Apr. 1, 2013;8(4):357-370. doi: 10.2217/fvl.13.22.
U.S. Appl. No. 96/000,401, filed Aug. 22, 2022.
U.S. Appl. No. 96/000,402, filed Aug. 22, 2022.
U.S. Appl. No. 96/000,403, filed Aug. 22, 2022.
U.S. Appl. No. 96/000,404, filed Aug. 22, 2022.
U.S. Appl. No. 96/000,405, filed Aug. 22, 2022.
U.S. Appl. No. 96/000,406, filed Aug. 22, 2022.
U.S. Appl. No. 96/000,407, filed Aug. 22, 2022.
U.S. Appl. No. 96/000,408, filed Aug. 22, 2022.
U.S. Appl. No. 96/000,411, filed Aug. 31, 2022.
Database Registry No. RN 2060799-65-5, "Pyrido[2,3-d]pyridazin-8-a:mine, 5-(5-bromo-2-thienyl)-N-(1-methylethyl)-" (CA Index Name). STN, Chemical Abstracts Service; entered Jan. 29, 2017; 1 printed page.
Database Registry No. RN 2062164-56-9, "Pyrido[2,3-d]pyridazin-8-amine, N-(I-methylethyl)-5-[5-(5-methyl-2-pyridinyl)-2-thienyl] -)" (CA Index Name). STN, Chemical Abstracts Service; entered Jan. 31, 2017; 1 printed page.
Database Registry No. RN 2062164-57-0, Pyrido[2,3-d]pyridazin-8-amine, N-(I-methylethyl)-5-[5-(5-methyl-2-pyridinyl)-2-thienyl]-, hydrochloride (1:1) (CA Index Name). STN, Chemical Abstracts Service; entered Jan. 31, 2017; 1 printed page.
Database Registry No. RN 154865-64-2, "Pyrido[2,3-d]pyridazin-8-amine,N-(1-methylethyl)-5-phenyl- (CA Index Name) ", STN Entry Date May 6, 1994, 1 printed page.

\* cited by examiner

COMPOUNDS FOR INHIBITING NLRP3 AND USES THEREOF

CROSS-REFERENCE RELATED APPLICATION

This application is a continuation application of U.S. patent application Ser. No. 17/679,898, filed Feb. 24, 2022, which is a continuation application of U.S. patent application Ser. No. 17/528,928, filed Nov. 17, 2021, now U.S. Pat. No. 11,319,319, which claims the benefit of U.S. Provisional Patent Application No. 63/171,932, filed Apr. 7, 2021, entitled "COMPOUNDS FOR INHIBITING NLRP3 AND USES THEREOF" the contents of each application is herein incorporated by reference in its entirety.

FIELD OF INVENTION

The present invention is directed to inhibitors of NLR family pyrin domain containing 3 (NLRP3) proteins. The inhibitors described herein are useful in the treatment of diseases and disorders associated with the modulation of NLRP3 proteins. In particular, the invention is concerned with compounds and pharmaceutical compositions inhibiting NLRP3, methods of treating diseases and disorders associated with NLRP3 using said compounds and pharmaceutical compositions, and methods of synthesizing said compounds and compositions.

BACKGROUND OF INVENTION

Innate immune responses are mediated by different types of receptors termed pattern-recognition receptors (PRRs). PRRs recognize the presence of pathogen-associated molecular patterns (PAMPs) and damage-associated molecular patterns (DAMPs). Once engaged these receptors trigger the activation of downstream inflammatory pathways that will help resolve injury. However, in many instances this activation can be uncontrolled and leads to disease.

The inflammasomes represent a class of PRRs that are crucial components of the innate immune response. Activation of the inflammasomes trigger a cascade of events that releases IL-1β, IL-18, and promotes an inflammatory form of cell death called pyroptosis induced by the activation of Gasdermin. Pyroptosis is a unique form of inflammatory cell death that leads to the release of not only cytokines but also other intracellular components that promote a broader immune response both of the innate and acquired immune system. Thus, inflammasome activation is a major regulatory of the inflammatory cascade.

NLRP3 is the most characterized inflammasome and has been shown to be critical in innate immunity and inflammatory responses. While several other NLR complexes, such as NLRC4, are activated under very specific circumstances, NLRP3 can be activated by numerous stimuli and should be seen as a sensor of intracellular homeostatic imbalance. Therefore, its precise functioning is essential. In addition to playing a role in host immune defense, dysregulation of NLRP3 has been linked to the pathogenesis of many inflammatory disorders. These include genetic diseases such as cryopyrin-associated periodic syndromes (CAPS) which is caused by gain-of-function mutations in the NLRP3 gene, as well as many prevalent neurologic and systemic diseases. Importantly, NLRP3 hyperactivation has been demonstrated pre-clinically to play a critical role in a plethora of inflammatory and degenerative diseases including, NASH, atherosclerosis and other cardiovascular diseases, Alzheimer's disease, Parkinson's disease, diabetes, gout, and numerous other autoinflammatory diseases. Thus, there is an unmet need in the field to develop small molecules for modulating NLRP3 activity to treat various diseases and disorders.

SUMMARY OF INVENTION

In a first aspect, the present disclosure provides, inter alia, compounds of Formula (I):

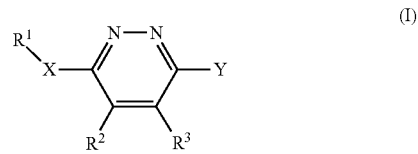

and pharmaceutically acceptable salts, solvates, clathrates, hydrates, stereoisomers, or tautomers thereof, wherein:

X is $N(R^a)$, O, S or $C(R^b)(R^c)$;

$R^a$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl; or $R^a$ cyclizes with $R^1$ to form a 3- to 8-membered heterocycloalkyl;

$R^b$ is hydrogen or $C_1$-$C_6$ alkyl;

$R^c$ is hydrogen or $C_1$-$C_6$ alkyl; or $R^b$ and $R^c$, together with the atoms to which they are attached, form a $C_3$-$C_8$ cycloalkyl;

Y is $C_3$-$C_8$ cycloalkyl, 3- to 8-membered heterocycloalkyl, $C_6$-$C_{10}$ aryl, or 5- to 9-membered heteroaryl, wherein the $C_3$-$C_8$ cycloalkyl, 3- to 8-membered heterocycloalkyl, $C_6$-$C_{10}$ aryl, or 5- to 9-membered heteroaryl is optionally substituted with one or more $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, 5- to 9-membered heteroaryl, halo, cyano, —$R^4OR^5$, —$R^4N(R^5)(R^6)$, —$R^4SR^6$, —$R^4C(O)OR^6$, —$R^4C(O)N(R^7)(R^8)$, —$R^4N(R^7)C(O)R^8$, —$R^8(O)_rR^5$, —$R^4S(O)_rN(R^7)(R^8)$, —$R^4N(R^7)S(O)_r(R^8)$, —$R^4P(O)(R^5)_2$, or —$R^4SF_5$;

$R^1$ is $C_1$-$C_6$ alkyl, $C_2$-$C_6$ alkenyl, $C_2$-$C_6$ alkynyl, $C_1$-$C_6$ haloalkyl, —$(CH_2)_n$—$(C_3$-$C_{10}$ cycloalkyl), —$(CH_2)_n$-(3- to 8-membered heterocycloalkyl), —$(CH_2)_n$—$(C_6$-$C_{10}$ aryl), —$(CH_2)_n$-(5- to 9-membered heteroaryl), —$R^4SR^6$, —$R^4C(O)OR^6$, —$R^4C(O)N(R^7)(R^8)$, —$R^4N(R^7)C(O)R^8$, —$R^4S(O)_rR^5$, —$R^4S(O)_rN(R^7)(R^8)$, —$R^4N(R^7)S(O)_r(R^8)$, or —$R^4P(O)(R^5)_2$ wherein the $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl is optionally substituted with one more halo, CN, $C_1$-$C_6$ alkyl, —$R^4OR^5$, —$NR^5R^6$, an optionally substituted 3- to 8-membered heterocycloalkyl, an optionally substituted $C_6$-$C_{10}$ aryl, or an optionally substituted 5- to 9-membered heteroaryl;

$R^2$ is hydrogen, halo, cyano, $C_1$-$C_6$ alkyl, $C_2$-$C_6$ alkenyl, $C_2$-$C_6$ alkynyl, $C_3$-$C_8$ cycloalkyl, 3- to 8-membered heterocycloalkyl, $C_6$-$C_{10}$ aryl, 5- to 9-membered heteroaryl, —$R^4OR^5$, —$R^4SR^6$, —$R^4C(O)OR^6$, —$R^4C(O)N(R^7)(R^8)$, —$R^4N(R^7)C(O)R^8$, —$R^4S(O)_rR^5$, —$R^4S(O)_rN(R^7)(R^8)$, —$R^4N(R^7)S(O)_r(R^8)$, —$R^4P(O)(R^5)_2$, or —$R^4SF_5$, wherein the $C_1$-$C_6$ alkyl, $C_2$-$C_6$ alkenyl, or $C_2$-$C_6$ alkynyl is optionally substituted with one or more $C_1$-$C_6$ alkyl, halo, or $C_1$-$C_6$ haloalkyl;

$R^3$ is hydrogen, halo, cyano, $C_1$-$C_6$ alkyl, $C_2$-$C_6$ alkenyl, $C_2$-$C_6$ alkynyl, $C_3$-$C_8$ cycloalkyl, 3- to 8-membered heterocycloalkyl, $C_6$-$C_{10}$ aryl, 5- to 9-membered heteroaryl, —$R^4OR^5$, —$R^4SR^6$, —$R^4C(O)OR^6$, —$R^4C(O)N(R^7)(R^8)$, —$R^4N(R^7)C(O)R^8$, —$R^4S(O)_tR^5$, —$R^4S(O)_tN(R^7)(R^8)$, —$R^4N(R^7)S(O)_t(R^8)$, —$R^4P(O)(R^5)_2$, or —$R^4SF_5$, wherein the $C_1$-$C_6$ alkyl, $C_2$-$C_6$ alkenyl, or $C_2$-$C_6$ alkynyl is optionally substituted with one or more $C_1$-$C_6$ alkyl, halo, or $C_1$-$C_6$ haloalkyl; or $R^2$ and $R^3$, together with the atoms to which they are attached, form a $C_3$-$C_8$ cycloalkyl, 3- to 8-membered heterocycloalkyl, $C_6$-$C_{10}$ aryl, or 5- to 9-membered heteroaryl, wherein the $C_3$-$C_8$ cycloalkyl, 3- to 8-membered heterocycloalkyl, $C_6$-$C_{10}$ aryl, or 5- to 9-membered heteroaryl is optionally substituted with one or more $R^{2a}$;

$R^{2a}$ is hydrogen, deuterium, $C_1$-$C_6$ alkyl, halo or $C_1$-$C_6$ haloalkyl;

$R^4$ is a bond, $C_1$-$C_6$ alkyl, $C_2$-$C_6$ alkenyl, or $C_2$-$C_6$ alkynyl;

$R^5$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl, wherein the alkyl is optionally substituted with one or more D;

$R^6$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl;

$R^7$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl;

$R^8$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl; or $R^7$ and $R^8$, together with the atoms to which they are attached, form a 3- to 8-membered heterocycloalkyl;

n is an integer from 0 to 4; and t is 1 or 2;

provided that $R^1$ is not $C_2$ or $C_4$ alkyl substituted with morpholinyl.

Another aspect of the disclosure relates to compounds of Formula I':

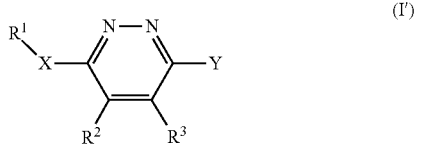

(I')

and pharmaceutically acceptable salts, solvates, clathrates, hydrates, stereoisomers, or tautomers thereof, wherein:

X is $N(R^a)$, O, S or $C(R^b)(R^c)$;

$R^a$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl; or $R^a$ cyclizes with $R^1$ to form a 3- to 8-membered heterocycloalkyl;

$R^b$ is hydrogen or $C_1$-$C_6$ alkyl;

$R^c$ is hydrogen or $C_1$-$C_6$ alkyl; or $R^b$ and $R^c$, together with the atoms to which they are attached, form a $C_3$-$C_8$ cycloalkyl;

Y is $C_3$-$C_8$ cycloalkyl, 3- to 8-membered heterocycloalkyl, $C_6$-$C_{10}$ aryl, or 5- to 9-membered heteroaryl, wherein the $C_3$-$C_8$ cycloalkyl, 3- to 8-membered heterocycloalkyl, $C_6$-$C_{10}$ aryl, or 5- to 9-membered heteroaryl is optionally substituted with one or more $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, 5- to 9-membered heteroaryl, halo, cyano, —$R^4OR^5$, —$R^4N(R^5)(R^6)$, —$R^4SR^6$, —$R^4C(O)OR^6$, —$R^4C(O)N(R^7)(R^8)$, —$R^4N(R^7)C(O)R^8$, —$R^4S(O)_tR^5$, —$R^4S(O)_tN(R^7)(R^8)$, $R^4N(R^7)S(O)_t(R^8)$, —$R^4P(O)(R^5)_2$, or —$R^4SF_5$;

$R^1$ is $C_1$-$C_6$ alkyl, $C_2$-$C_6$ alkenyl, $C_2$-$C_6$ alkynyl, $C_1$-$C_6$ haloalkyl, —$(CH_2)_n$—$(C_3$-$C_{10}$ cycloalkyl), —$(CH_2)_n$—$(C_6$-$C_{10}$ aryl), —$(CH_2)_n$-(3- to 8-membered heterocycloalkyl), or —$(CH_2)_n$-(5- to 9-membered heteroaryl), —$R^4SR^6$, —$R^4C(O)OR^6$, —$R^4C(O)N(R^7)(R^8)$, —$R^4N(R^7)C(O)R^8$, —$R^4S(O)_tR^5$, —$R^4S(O)_tN(R^7)(R^8)$, $R^4N(R^7)S(O)_t(R^8)$, or —$R^4P(O)(R^5)_2$, wherein the $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl is optionally substituted with one more halo, CN, $C_1$-$C_6$ alkyl, —$NR^5R^6$, —$R^4OR^5$, an optionally substituted 3- to 8-membered heterocycloalkyl, an optionally substituted $C_6$-$C_{10}$ aryl, or an optionally substituted 5- to 9-membered heteroaryl;

$R^2$ and $R^3$, together with the atoms to which they are attached, form a $C_3$-$C_8$ cycloalkyl, 3- to 8-membered heterocycloalkyl, $C_6$-$C_{10}$ aryl, or 5- to 9-membered heteroaryl, wherein the $C_3$-$C_8$ cycloalkyl, 3- to 8-membered heterocycloalkyl, $C_6$-$C_{10}$ aryl, or 5- to 9-membered heteroaryl is optionally substituted with one or more $R^{2a}$;

$R^2$, is hydrogen, deuterium, $C_1$-$C_6$ alkyl, halo or $C_1$-$C_6$ haloalkyl;

$R^4$ is a bond, $C_1$-$C_6$ alkyl, $C_2$-$C_6$ alkenyl, or $C_2$-$C_6$ alkynyl;

$R^5$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl, wherein the alkyl is optionally substituted with one or more D;

$R^6$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl;

$R^7$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl;

$R^8$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl; or $R^7$ and $R^8$, together with the atoms to which they are attached, form a 3- to 8-membered heterocycloalkyl;

n is an integer from 0 to 4; and t is 1 or 2;

provided that $R^1$ is not $C_2$ or $C_4$ alkyl substituted with morpholinyl.

Another aspect of the disclosure relates to compounds of Formula I":

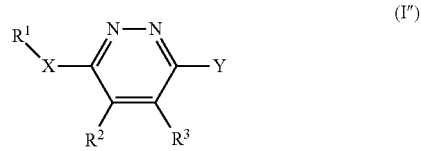

(I")

and pharmaceutically acceptable salts, solvates, clathrates, hydrates, stereoisomers, or tautomers thereof, wherein:

X is $N(R^a)$, O, S or $C(R^b)(R^c)$;

$R^a$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl; or $R^a$ cyclizes with $R^1$ to form a 3- to 8-membered heterocycloalkyl;

$R^b$ is hydrogen or $C_1$-$C_6$ alkyl;

$R^c$ is hydrogen or $C_1$-$C_6$ alkyl; or $R^b$ and $R^c$, together with the atoms to which they are attached, form a $C_3$-$C_8$ cycloalkyl;

Y is $C_3$-$C_8$ cycloalkyl, 3- to 8-membered heterocycloalkyl, $C_6$-$C_{10}$ aryl, or 5- to 9-membered heteroaryl, wherein the $C_3$-$C_8$ cycloalkyl, 3- to 8-membered heterocycloalkyl, $C_6$-$C_{10}$ aryl, or 5- to 9-membered heteroaryl is optionally substituted with one or more $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, 5- to 9-membered heteroaryl, halo, cyano, —$R^4OR^5$, —$R^4N(R^5)(R^6)$, —$R^4SR^6$, —$R^4C(O)OR^6$, —$R^4C(O)N(R^7)(R^8)$, —$R^4N(R^7)C(O)R^8$, —$R^4S(O)_tR^5$, —$R^4S(O)_tN(R^7)(R^8)$, $R^4N(R^7)S(O)_t(R^8)$, —$R^4P(O)(R^5)_2$, or —$R^4SF_5$;

$R^1$ is $C_1$-$C_6$ alkyl, $C_2$-$C_6$ alkenyl, $C_2$-$C_6$ alkynyl, $C_1$-$C_6$ haloalkyl, —$CH_2)_n$—$(C_3$-$C_{10}$ cycloalkyl), —$(CH_2)_n$—$(C_6$-$C_{10}$ aryl), —$(CH_2)_n$-(3- to 8-membered heterocycloalkyl), or —$(CH_2)_n$-(5- to 9-membered heteroaryl), —$R^4SR^6$, —$R^4C(O)OR^6$, —$R^4C(O)N(R^7)(R^8)$, —$R^4N(R^7)C(O)R^8$, —$R^4S(O)_tR^5$, —$R^4S(O)_tN(R^7)(R^8)$, $R^4N(R^7)S(O)_t(R^8)$, or —$R^4P(O)(R^5)_2$, wherein the $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl is optionally substituted with one more halo, CN, $C_1$-$C_6$ alkyl, —$NR^5R^6$, —$R^4OR^5$, an optionally substituted 3- to 8-membered heterocycloalkyl, an optionally substituted $C_6$-$C_{10}$ aryl, or an optionally substituted 5- to 9-membered heteroaryl;

$R^2$ is hydrogen, halo, cyano, $C_1$-$C_6$ alkyl, $C_2$-$C_6$ alkenyl, $C_2$-$C_6$ alkynyl, $C_3$-$C_8$ cycloalkyl, 3- to 8-membered heterocycloalkyl, $C_6$-$C_{10}$ aryl, 5- to 9-membered heteroaryl, —$R^4OR^5$, —$R^4SR^6$, —$R^4C(O)OR^6$, —$R^4C(O)N(R^7)(R^8)$, —$R^4N(R^7)C(O)R^8$, —$R^4S(O)_tR^5$, —$R^4S(O)_tN(R^7)(R^8)$, $R^4N(R^7)S(O)_t(R^8)$, —$R^4P(O)(R^5)_2$, or —$R^4SF_5$, wherein the $C_1$-$C_6$ alkyl, $C_2$-$C_6$ alkenyl, or $C_2$-$C_6$ alkynyl, is optionally substituted with one or more $C_1$-$C_6$ alkyl, halo, or $C_1$-$C_6$ haloalkyl;

$R^3$ is hydrogen, halo, cyano, $C_1$-$C_6$ alkyl, $C_2$-$C_6$ alkenyl, $C_2$-$C_6$ alkynyl, $C_1$-$C_8$ cycloalkyl, 3- to 8-membered heterocycloalkyl, $C_6$-$C_{10}$ aryl, 5- to 9-membered heteroaryl, —$R^4OR^5$, —$R^4SR^6$, —$R^4C(O)OR^6$, —$R^4C(O)N(R^7)(R^8)$, —$R^4N(R^7)C(O)R^8$, —$R^4S(O)_tR^5$, —$R^4S(O)_tN(R^7)(R^8)$, $R^4N(R^7)S(O)_t(R^5)$, —$R^4P(O)(R^5)_2$, or —$R^4SF_5$, wherein the $C_1$-$C_6$ alkyl, $C_2$-$C_6$ alkenyl, or $C_2$-$C_6$ alkynyl, is optionally substituted with one or more $C_1$-$C_6$ alkyl, halo, or $C_1$-$C_6$ haloalkyl;

$R^4$ is a bond, $C_1$-$C_6$ alkyl, $C_2$-$C_6$ alkenyl, or $C_2$-$C_6$ alkynyl, wherein $R^4$ can only be a bond with —$R^4OR^5$;

$R^5$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl, wherein the alkyl is optionally substituted with one or more D;

$R^6$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl;

$R^7$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl;

$R^8$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl; or $R^7$ and $R^8$, together with the atoms to which they are attached, form a 3- to 8-membered heterocycloalkyl;

n is an integer from 0 to 4; and t is 1 or 2:

provided that $R^1$ is not $C_2$ or $C_4$ alkyl substituted with morpholinyl.

Another aspect of the disclosure relates to compounds of Formula II:

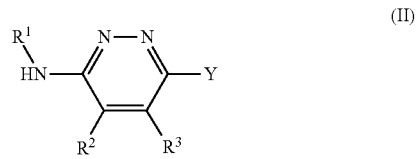

and pharmaceutically acceptable salts, solvates, clathrates, hydrates, stereoisomers, or tautomers thereof, wherein:

Y is $C_3$-$C_8$ cycloalkyl, 3- to 8-membered heterocycloalkyl, $C_6$-$C_{10}$ aryl, or 5- to 9-membered heteroaryl, wherein the $C_3$-$C_8$ cycloalkyl, 3- to 8-membered heterocycloalkyl, $C_6$-$C_{10}$ aryl, or 5- to 9-membered heteroaryl is optionally substituted with one or more $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, 5- to 9-membered heteroaryl, halo, cyano, —$R^4OR^5$, —$R^4N(R^5)(R^6)$, —$R^4SR^6$, —$R^4C(O)OR^6$, —$R^4C(O)N(R^7)(R^8)$, —$R^4N(R^7)C(O)R^8$, —$R^4S(O)_tR^5$, —$R^4S(O)_tN(R^7)(R^8)$, —$R^4N(R^7)S(O)_t(R^8)$, —$R^4P(O)(R^5)_2$, or —$R^4SF_5$;

$R^1$ is $C_1$-$C_6$ alkyl, $C_2$-$C_6$ alkenyl, $C_2$-$C_6$ alkynyl, $C_1$-$C_6$ haloalkyl, —$CH_2)_n$—$(C_3$-$C_{10}$ cycloalkyl), —$(CH_2)_n$—$(C_6$-$C_{10}$ aryl), —$(CH_2)_n$-(3- to 8-membered heterocycloalkyl), or —$(CH_2)_n$-(5- to 9-membered heteroaryl), —$R^4SR^6$, —$R^4C(O)OR^6$, —$R^4C(O)N(R^7)(R^8)$, —$R^4N(R^7)C(O)R^8$, —$R^4S(O)_tR^5$, —$R^4S(O)_tN(R^7)(R^8)$, —$R^4N(R^7)S(O)_t(R^8)$, or —$R^4P(O)(R^5)_2$ wherein the $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl is optionally substituted with one more halo, CN, $C_1$-$C_6$ alkyl, —$NR^5R^6$, —$R^4OR^5$, an optionally substituted 3- to 8-membered heterocycloalkyl, an optionally substituted $C_6$-$C_{10}$ aryl, or an optionally substituted 5- to 9-membered heteroaryl;

$R^2$ is hydrogen, halo, cyano, $C_1$-$C_6$ alkyl, $C_2$-$C_6$ alkenyl, $C_2$-$C_6$ alkynyl, $C_1$-$C_8$ cycloalkyl, 3- to 8-membered heterocycloalkyl, $C_6$-$C_{10}$ aryl, 5- to 9-membered heteroaryl, —$R^4OR^5$, —$R^4SR^6$, —$R^4C(O)OR^6$, —$R^4C(O)N(R^7)(R^8)$, —$R^4N(R^7)C(O)R^8$, —$R^4S(O)_tR^5$, —$R^4S(O)_tN(R^7)(R^8)$, —$R^4N(R^7)S(O)_t(R^8)$, —$R^4P(O)(R^5)_2$, or —$R^4SF_5$, wherein the $C_1$-$C_6$ alkyl, $C_2$-$C_6$ alkenyl, or $C_2$-$C_6$ alkynyl is optionally substituted with one or more $C_1$-$C_6$ alkyl, halo, or $C_1$-$C_6$ haloalkyl;

$R^3$ is hydrogen, halo, cyano, $C_1$-$C_6$ alkyl, $C_2$-$C_6$ alkenyl, $C_2$-$C_6$ alkynyl, $C_3$-$C_8$ cycloalkyl, 3- to 8-membered heterocycloalkyl, $C_6$-$C_{10}$ aryl, 5- to 9-membered heteroaryl, —$R^4OR^5$, —$R^4SR^6$, —$R^4C(O)OR^6$, —$R^4C(O)N(R^7)(R^8)$, —$R^4N(R^7)C(O)R^8$, —$R^4S(O)_tR^5$, —$R^4S(O)_tN(R^7)(R^8)$, —$R^4N(R^7)S(O)_t(R^8)$, —$R^4P(O)(R^5)_2$, or —$R^4SF_5$, wherein the $C_1$-$C_6$ alkyl, $C_2$-$C_6$ alkenyl, or $C_2$-$C_6$ alkynyl is optionally substituted with one or more $C_1$-$C_6$ alkyl, halo, or $C_1$-$C_6$ haloalkyl; or $R^2$ and $R^3$, together with the atoms to which they are attached, form a $C_3$-$C_8$ cycloalkyl, 3- to 8-membered heterocycloalkyl, $C_6$-$C_{10}$ aryl, or 5- to 9-membered heteroaryl, wherein the $C_3$-$C_8$ cycloalkyl, 3- to 8-membered heterocycloalkyl, $C_6$-$C_{10}$ aryl, or 5- to 9-membered heteroaryl is optionally substituted with one or more $R^{2a}$;

$R^{2a}$ is hydrogen, deuterium, $C_1$-$C_6$ alkyl, halo or $C_1$-$C_6$ haloalkyl;

$R^4$ is a bond, $C_1$-$C_6$ alkyl, $C_2$-$C_6$ alkenyl, or $C_2$-$C_6$ alkynyl;

$R^5$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl, wherein the alkyl is optionally substituted with one or more D;

$R^6$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl;

$R^7$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl;

$R^8$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl; or $R^7$ and $R^8$, together with the atoms to which they are attached, form a 3- to 8-membered heterocycloalkyl;

n is an integer from 0 to 4; and t is 1 or 2;

provided that $R^1$ is not $C_2$ or $C_4$ alkyl substituted with morpholinyl.

In some aspects, the present disclosure provides compounds obtainable by, or obtained by, a method for preparing a compound as described herein (e.g., a method comprising one or more steps described in Schemes 1, 2, and 3).

In some aspects, the present disclosure provides pharmaceutical compositions comprising a compound of the present disclosure, or a pharmaceutically acceptable salt thereof, and a pharmaceutically acceptable diluent or carrier.

In some aspects, the present disclosure provides an intermediate as described herein, being suitable for use in a method for preparing a compound as described herein (e.g., the intermediate is selected from the intermediates described in Examples 1 and 2.

In some aspects, the present disclosure provides a method of treating or preventing a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a compound of the present disclosure or a pharmaceutically acceptable salt thereof for use in treating or preventing a disease or disorder disclosed herein.

In some aspects, the present disclosure provides a compound of the present disclosure or a pharmaceutically acceptable salt thereof for use in treating a disease or disorder disclosed herein.

In some aspects, the present disclosure provides use of a compound of the present disclosure or a pharmaceutically acceptable salt thereof in the manufacture of a medicament for treating or preventing a disease or disorder disclosed herein.

In some aspects, the present disclosure provides use of a compound of the present disclosure or a pharmaceutically acceptable salt thereof in the manufacture of a medicament for treating a disease or disorder disclosed herein.

In some embodiments, the disease or disorder is inflammation, an auto-immune disease, a cancer, an infection, a disease or disorder of the central nervous system, a metabolic disease, a cardiovascular disease, a respiratory disease, a kidney disease, a liver disease, an ocular disease, a skin disease, a lymphatic disease, a rheumatic disease, a psychological disease, graft versus host disease, allodynia, or an NLRP3-related disease in a subject that has been determined to carry a germline or somatic non-silent mutation in NLRP3.

In some embodiments, the disease or disorder of the central nervous system is Parkinson's disease, Alzheimer's disease, traumatic brain injury, spinal cord injury, amyotrophic lateral sclerosis, or multiple sclerosis.

In some embodiments, the kidney disease is an acute kidney disease, a chronic kidney disease, or a rare kidney disease.

In some embodiments, the skin disease is psoriasis, hidradenitis suppurativa (HS), or atopic dermatitis.

In some embodiments, the rheumatic disease is dermatomyositis, Still's disease, or juvenile idiopathic arthritis.

In some embodiments, the NLRP3-related disease in a subject that has been determined to carry a germline or somatic non-silent mutation in NLRP3 is cryopyrin-associated autoinflammatory syndrome.

In some embodiments, the cryopyrin-associated autoinflammatory syndrome is familial cold autoinflammatory syndrome, Muckle-Wells syndrome, or neonatal onset multisystem inflammatory disease.

In some aspects, the present disclosure provides a method of preparing a compound of the present disclosure.

In some aspects, the present disclosure provides a method of preparing a compound, comprising one or more steps described herein.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

DETAILED DESCRIPTION OF INVENTION

The present disclosure relates to pyridazine and phthalazine derivatives, pharmaceutically acceptable salts, solvates, clathrates, hydrates, single stereoisomers, mixtures of stereoisomers, or racemic mixtures of stereoisomers thereof, which may inhibit NLRP3 activity and are accordingly useful in methods of treatment of the human or animal body. The present disclosure also relates to processes for the preparation of these compounds, to pharmaceutical compositions comprising them and to their use in the treatment of disorders in which NLRP3 is implicated, such as inflammation, an auto-immune disease, a cancer, an infection, a disease or disorder of the central nervous system, a metabolic disease, a cardiovascular disease, a respiratory disease, a kidney disease, a liver disease, an ocular disease, a skin disease, a lymphatic disease, a rheumatic disease, a psychological disease, graft versus host disease, allodynia, or an NLRP3-related disease in a subject that has been determined to carry a germline or somatic non-silent mutation in NLRP3.

Definitions

Unless otherwise stated, the following terms used in the specification and claims have the following meanings set out below.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl, or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

As used herein, the term "cyano" refers to a nitrile radical (e.g., —CN).

As used herein, the term "cycloalkyl" refers to a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. In the case of polycyclic cycloalkyl, only one of the rings in the cycloalkyl needs to be non-aromatic.

As used herein, the term "heterocycloalkyl" refers to a saturated or partially unsaturated 3-8 membered monocyclic or bicyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, 5,6-dihydro-4H-cyclopenta[b]thiophenyl, and the like. In the case of multicyclic heterocycloalkyl, only one of the rings in the heterocycloalkyl needs to be non-aromatic (e.g., 4,5,6,7-tetrahydrobenzo[c]isoxazolyl).

As used herein, the term "optionally substituted heterocycloalkyl" refers to unsubstituted heterocycloalkyl having designated substituents replacing one or more hydrogen atoms on one or more carbon or heteroatom. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless otherwise specifically defined, the term "aryl" refers to cyclic, aromatic hydrocarbon groups that have 1 to 3 aromatic rings, including monocyclic or bicyclic groups such as phenyl, biphenyl, or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$) alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, —NH$_2$, NH(($C_1$-$C_6$) alkyl), N(($C_1$-$C_6$) alkyl)$_2$, —S(O)$_2$—($C_1$-$C_6$) alkyl, —S(O)NH($C_1$-$C_6$) alkyl, and —S(O)N(($C_1$-$C_6$) alkyl)$_2$. The substituents can themselves be optionally substituted. Furthermore, when containing two or more fused rings, the aryl groups herein defined may have a saturated or partially unsaturated ring fused with a fully unsaturated aromatic ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, 10,11-dihydro-5H-dibenzo[a,d][7]annulenyl, and the like.

Unless otherwise specifically defined, "heteroaryl" means a monovalent monocyclic or polycyclic aromatic radical of 5 to 24 ring atoms, containing one or more ring heteroatoms selected from N, O, S, P, Se, or B, the remaining ring atoms being C. Heteroaryl as herein defined also means a bicyclic heteroaromatic group wherein the heteroatom is selected from N, O, S, P, Se, or B. Heteroaryl as herein defined also means a tricyclic heteroaromatic group containing one or more ring heteroatoms selected from N, O, S, P, Se, or B. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolinyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4] thiazinyl, benzoxazolyl, benzisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore, when containing two or more fused rings, the heteroaryl groups defined herein may have one or more saturated or partially unsaturated ring fused with a fully unsaturated aromatic ring, e.g., a 5-membered heteroaromatic ring containing 1 to 3 heteroatoms selected from N, O, S, P, Se, or B, or a 6-membered heteroaromatic ring containing 1 to 3 nitrogens, wherein the saturated or partially unsaturated ring includes 0 to 4 heteroatoms selected from N, O, S, P, Se, or B, and is optionally substituted with one or more oxo. In heteroaryl ring systems containing more than two fused rings, a saturated or partially unsaturated ring may further be fused with a saturated or partially unsaturated ring described herein. Exemplary ring systems of these heteroaryl groups include, for example, indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuranyl, benzofuranonyl, indolinyl, oxindolyl, indolyl, 1,6-dihydro-7H-pyrazolo[3,4-c]pyridin-7-onyl, 7,8-dihydro-6H-pyrido[3,2-b]pyrrolizinyl, 8H-pyrido[3,2-b]pyrrolizinyl, 1,5,6,7-tetrahydrocyclopenta[b]pyrazolo[4,3-e]pyridinyl, 7,8-dihydro-6H-pyrido[3,2-b]pyrrolizine, pyrazolo[1,5-a]pyrimidin-7(4H)-only, 3,4-dihydropyrazino[1,2-a]indol-1(2H)-onyl, or benzo[c][1,2]oxaborol-1(3H)-olyl.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a RM, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term "hydroxy" or "hydroxyl" includes groups with an —OH or —O—.

As used herein, the term "halo" or "halogen" refers to fluoro, chloro, bromo and iodo.

The term "haloalkyl" or "haloalkoxyl" refers to an alkyl or alkoxyl substituted with one or more halogen atoms.

As used herein, the term "optionally substituted haloalkyl" refers to unsubstituted haloalkyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

It is to be understood that the present disclosure provides methods for the synthesis of the compounds of any of the Formulae described herein. The present disclosure also provides detailed methods for the synthesis of various disclosed compounds of the present disclosure according to the following schemes as well as those shown in the Examples.

It is to be understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry: Reactions, Mechanisms, and Structure, 5th edition, John Wiley & Sons: New York, 2001; Greene, T. W., Wuts, P. G. M., Protective Groups in Organic Synthesis, 3rd edition, John Wiley & Sons: New York, 1999; R. Larock, Comprehensive Organic Transformations, VCH Publishers (1989); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), incorporated by reference herein, are useful and recognised reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognise that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., Protective Groups in Organic Synthesis, 3rd edition, John Wiley & Sons: New York, 1999.

It is to be understood that, unless otherwise stated, any description of a method of treatment or prevention includes use of the compounds to provide such treatment or prevention as is described herein. It is to be further understood, unless otherwise stated, any description of a method of treatment or prevention includes use of the compounds to prepare a medicament to treat or prevent such condition. The treatment or prevention includes treatment or prevention of human or non-human animals including rodents and other disease models.

It is to be understood that, unless otherwise stated, any description of a method of treatment includes use of the compounds to provide such treatment as is described herein. It is to be further understood, unless otherwise stated, any description of a method of treatment includes use of the compounds to prepare a medicament to treat such condition. The treatment includes treatment of human or non-human animals including rodents and other disease models. As used herein, the term "subject" is interchangeable with the term "subject in need thereof", both of which refer to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or a pig. In one embodiment, the mammal is a human. A subject in need thereof can be one who has been previously diagnosed or identified as having a disease or disorder disclosed herein. A subject in need thereof can also be one who is suffering from a disease or disorder disclosed herein. Alternatively, a subject in need thereof can be one who has an increased risk of developing such disease or disorder relative to the population at large (i.e., a subject who is predisposed to developing such disorder relative to the population at large). A subject in need thereof can have a refractory or resistant a disease or disorder disclosed herein (i.e., a disease or disorder disclosed herein that does not respond or has not yet responded to treatment). The subject may be resistant at start of treatment or may become resistant during treatment. In some embodiments, the subject in need thereof received and failed all known effective therapies for a disease or disorder disclosed herein. In some embodiments, the subject in need thereof received at least one prior therapy.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model. It is to be appreciated that references to "treating" or "treatment" include the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

It is to be understood that a compound of the present disclosure, or a pharmaceutically acceptable salt, polymorph or solvate thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

It is to be understood that one skilled in the art may refer to general reference texts for detailed descriptions of known techniques discussed herein or equivalent techniques. These texts include Ausubel et al., Current Protocols in Molecular Biology, John Wiley and Sons, Inc. (2005); Sambrook et al., Molecular Cloning, A Laboratory Manual (3rd edition), Cold Spring Harbor Press, Cold Spring Harbor, New York.

(2000); Coligan et al., Current Protocols in Immunology, John Wiley & Sons, N.Y.; Enna et al., Current Protocols in Pharmacology, John Wiley & Sons, N.Y.; Fingl et al., The Pharmacological Basis of Therapeutics (1975), Remington's Pharmaceutical Sciences, Mack Publishing Co., Easton, PA, 18th edition (1990). These texts can, of course, also be referred to in making or using an aspect of the disclosure.

It is to be understood that the present disclosure also provides pharmaceutical compositions comprising any compound described herein in combination with at least one pharmaceutically acceptable excipient or carrier.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral (e.g., ingestion), inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for chemotherapeutic treatment. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition (e.g., a disease or disorder disclosed herein) and the health of the patient should preferably be closely monitored during and for a reasonable period after treatment.

As used herein, the term "therapeutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

It is to be understood that, for any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilising processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilisation. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch: a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebuliser.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the symptoms of the disease or disorder disclosed herein and also preferably causing complete regression of the disease or disorder. Dosages can range from about 0.01 mg/kg per day to about 5000 mg/kg per day. An effective amount of a pharmaceutical agent is that which provides an objectively identifiable improvement as noted by the clinician or other qualified observer. Improvement in survival and growth indicates regression. As used herein, the term "dosage effective manner" refers to amount of an active compound to produce the desired biological effect in a subject or cell.

It is to be understood that the pharmaceutical compositions can be included in a container, pack, or dispenser together with instructions for administration.

It is to be understood that, for the compounds of the present disclosure being capable of further forming salts, all of these forms are also contemplated within the scope of the claimed disclosure.

As used herein, the term "pharmaceutically acceptable salts" refer to derivatives of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

In some embodiments, the pharmaceutically acceptable salt is a sodium salt, a potassium salt, a calcium salt, a magnesium salt, a diethylamine salt, a choline salt, a meglumine salt, a benzathine salt, a tromethamine salt, an ammonia salt, an arginine salt, or a lysine salt.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3.

It is to be understood that all references to pharmaceutically acceptable salts include solvent addition forms (solvates) or crystal forms (polymorphs) as defined herein, of the same salt.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognise the advantages of certain routes of administration.

The dosage regimen utilising the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition. An ordinarily skilled physician or veterinarian can readily determine and prescribe the effective amount of the drug required to counter or arrest the progress of the condition.

Techniques for formulation and administration of the disclosed compounds of the disclosure can be found in Remington: the Science and Practice of Pharmacy, 19th edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

As use herein, the phrase "compound of the disclosure" refers to those compounds which are disclosed herein, both generically and specifically.

Compounds of the Present Disclosure

In one aspect, the present disclosure provides, inter alia, compounds of Formula (I)

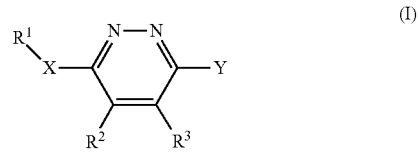

and pharmaceutically acceptable salts, solvates, clathrates, hydrates, stereoisomers or tautomers thereof, wherein:

X, Y, $R^1$, $R^2$, $R^3$ are described herein as set forth in Formula I.

In some embodiments, the compound is of Formula (I')

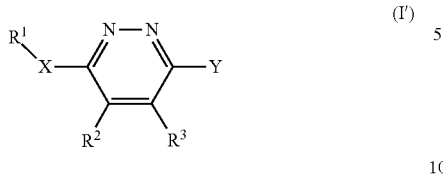

and pharmaceutically acceptable salts, solvates, clathrates, hydrates, stereoisomers, or tautomers thereof, wherein:

X, Y, and $R^1$ are described herein as set forth in Formula I;

$R^2$ and $R^3$, together with the atoms to which they are attached, form a $C_3$-$C_8$ cycloalkyl, 3- to 8-membered heterocycloalkyl, $C_6$-$C_{10}$ aryl, or 5- to 9-membered heteroaryl, wherein the $C_3$-$C_8$ cycloalkyl, 3- to 8-membered heterocycloalkyl, $C_6$-$C_{10}$ aryl, or 5- to 9-membered heteroaryl is optionally substituted with one or more $R^{2a}$; and $R^{2a}$ is hydrogen, deuterium, $C_1$-$C_6$ alkyl, halo or $C_1$-$C_6$ haloalkyl.

In some embodiments, the compound is of Formula (I")

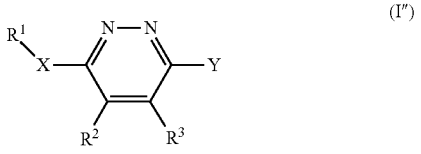

and pharmaceutically acceptable salts, solvates, clathrates, hydrates, stereoisomers, or tautomers thereof, wherein:

X, Y, and $R^1$ are described herein as set forth in Formula I";

$R^2$ is hydrogen, halo, cyano, $C_1$-$C_6$ alkyl, $C_2$-$C_6$ alkenyl, $C_2$-$C_6$ alkynyl, $C_3$-$C_8$ cycloalkyl, 3- to 8-membered heterocycloalkyl, $C_6$-$C_{10}$ aryl, 5- to 9-membered heteroaryl, —$R^4OR^5$, —$R^4SR^6$, —$R^4C(O)OR^6$, —$R^4C(O)N(R^7)(R^8)$, —$R^4S(O)_rR^5$, —$R^4S(O)_tN(R^7)(R^8)$, —$R^4P(O)(R^8)_2$, or —$R^4SF_5$, wherein the $C_1$-$C_6$ alkyl, $C_2$-$C_6$ alkenyl, or $C_2$-$C_6$ alkynyl, is optionally substituted with one or more $C_1$-$C_6$ alkyl, halo, or $C_1$-$C_6$ haloalkyl; and $R^3$ is hydrogen, halo, cyano, $C_1$-$C_6$ alkyl, $C_2$-$C_6$ alkenyl, $C_2$-$C_6$ alkynyl, $C_3$-$C_8$ cycloalkyl, 3- to 8-membered heterocycloalkyl, $C_6$-$C_{10}$ aryl, 5- to 9-membered heteroaryl, —$R^4OR^5$, —$R^4SR^6$, —$R^4C(O)OR^6$, —$R^4C(O)N(R^7)(R^8)$, —$R^4S(O)_rR^5$, —$R^4S(O)_tN(R^7)(R^8)$, —$R^4P(O)(R^5)_2$, or —$R^4SF_5$, wherein the $C_1$-$C_6$ alkyl, $C_2$-$C_6$ alkenyl, or $C_2$-$C_6$ alkynyl, is optionally substituted with one or more $C_1$-$C_6$ alkyl, halo, or $C_1$-$C_6$ haloalkyl.

In some embodiments, the compound of formula (I) is a compound of formula (II):

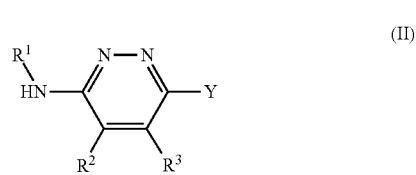

and pharmaceutically acceptable salts, solvates, clathrates, hydrates, stereoisomers, or tautomers thereof, wherein:

Y, $R^1$, $R^2$, and $R^3$ are described herein as set forth in Formula II.

In some embodiments, the compound of formula (TI) is a compound of formula (II-a):

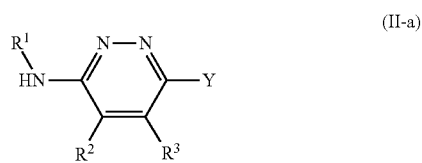

and pharmaceutically acceptable salts, solvates, clathrates, hydrates, stereoisomers, or tautomers thereof, wherein:

Y, $R^{2a}$, $R^4$, and $R^5$ are described herein as set forth in Formula II;

$R^1$ is $C_1$-$C_6$ alkyl substituted with one more halo, —$R^4OR^5$, an optionally substituted 3- to 8-membered heterocycloalkyl, or an optionally substituted 5- to 9-membered heteroaryl; and $R^2$ and $R^3$, together with the atoms to which they are attached, form a $C_3$-$C_8$ cycloalkyl, 3- to 8-membered heterocycloalkyl, $C_6$-$C_{10}$ aryl, or 5- to 9-membered heteroaryl, wherein the $C_3$-$C_8$ cycloalkyl, 3- to 8-membered heterocycloalkyl, $C_6$-$C_{10}$ aryl, or 5- to 9-membered heteroaryl is optionally substituted with one or more $R^{2a}$.

In some embodiments, the compound of formula (II) is a compound of formula (II-b):

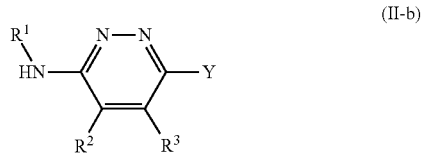

or pharmaceutically acceptable salts, solvates, clathrates, hydrates, stereoisomers, or tautomers thereof, wherein:

Y, $R^{2a}$, $R^4$, and $R^5$ are described herein as set forth in Formula II;

$R^1$ is $C_1$-$C_6$ alkyl substituted with one more halo, —$R^4OR^5$, an optionally substituted 3- to 8-membered heterocycloalkyl, or an optionally substituted 5- to 9-membered heteroaryl; and $R^2$ and $R^3$, together with the atoms to which they are attached, form a $C_3$-$C_8$ cycloalkyl optionally substituted with one or more $R^{2a}$.

In some embodiments, the compound of formula (II) is a compound of formula (II-c):

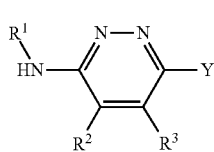

(II-c)

and pharmaceutically acceptable salts, solvates, clathrates, hydrates, stereoisomers, or tautomers thereof, wherein:
Y, $R^{2a}$, $R^4$, and $R^5$ are described herein as set forth in Formula II;
$R^1$ is $C_1$-$C_6$ alkyl substituted with one more halo, —$R^4OR^5$, an optionally substituted 3- to 8-membered heterocycloalkyl, or an optionally substituted 5- to 9-membered heteroaryl; and
$R^2$ and $R^3$, together with the atoms to which they are attached, form a 3- to 8-membered heterocycloalkyl optionally substituted with one or more $R^{2a}$.

In some embodiments, the compound of formula (II) is a compound of formula (II-d):

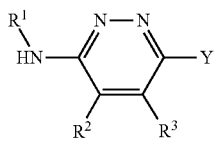

(II-d)

and pharmaceutically acceptable salts, solvates, clathrates, hydrates, stereoisomers, or tautomers thereof, wherein:
Y, $R^{2a}$, $R^4$, and $R^5$ are described herein as set forth in Formula II;
$R^1$ is $C_1$-$C_6$ alkyl substituted with one more halo, —$R^4OR^5$, 3- to 8-membered heterocycloalkyl, or 5- to 9-membered heteroaryl; and
$R^2$ and $R^3$, together with the atoms to which they are attached, form a $C_6$-$C_{10}$ aryl optionally substituted with one or more $R^{2a}$.

In some embodiments, the compound of formula (II) is a compound of formula (II-d-1):

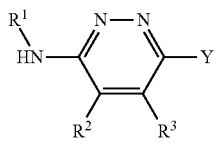

(II-d-1)

and pharmaceutically acceptable salts, solvates, clathrates, hydrates, stereoisomers, or tautomers thereof, wherein:
Y, $R^2$, $R^4$, and $R^5$ are described herein as set forth in Formula II;
$R^1$ is $C_1$-$C_6$ alkyl substituted with one more halo, —$R^4OR^5$, an optionally substituted 3- to 8-membered heterocycloalkyl, or an optionally substituted 5- to 9-membered heteroaryl; and
$R^2$ and $R^3$, together with the atoms to which they are attached, form a 5- to 9-membered heteroaryl optionally substituted with one or more $R^2$.

In some embodiments, the compound of formula (II) is a compound of formula (II-e):

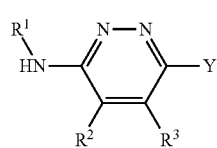

(II-e)

and pharmaceutically acceptable salts, solvates, clathrates, hydrates, stereoisomers, or tautomers thereof, wherein:
$R^{2a}$, $R^4$, and $R^5$ are described herein as set forth in Formula II;
$R^1$ is $C_1$-$C_6$ alkyl substituted with one more halo, —$R^4OR^5$, an optionally substituted 3- to 8-membered heterocycloalkyl, or an optionally substituted 5- to 9-membered heteroaryl;
$R^2$ and $R^3$, together with the atoms to which they are attached, form a $C_6$-$C_{10}$ aryl or 5- to 9-membered heteroaryl, wherein the $C_3$-$C_8$ cycloalkyl, 3- to 8-membered heterocycloalkyl, $C_5$-$C_{10}$ aryl, or 5- to 9-membered heteroaryl is optionally substituted with one or more $R^{2a}$; and
Y is 3- to 8-membered heterocycloalkyl, $C_6$-$C_{10}$ aryl, or 5- to 9-membered heteroaryl, wherein the 3- to 8-membered heterocycloalkyl, $C_6$-$C_{10}$ aryl, or 5- to 9-membered heteroaryl is optionally substituted with one, two, or three of any of $C_1$-$C_6$ haloalkyl, $C_3$-$C_8$ cycloalkyl, halo, cyano, or —$R^4OR^5$.

In some embodiments, the compound of formula (II) is a compound of formula (II-f):

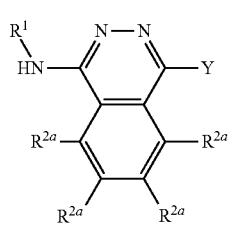

(II-f)

and pharmaceutically acceptable salts, solvates, clathrates, hydrates, stereoisomers, or tautomers thereof, wherein:
$R^{2a}$, $R^4$, and $R^5$ are described herein as set forth in Formula II;
$R^1$ is $C_1$-$C_6$ alkyl substituted with one more halo, —$R^4OR^5$, an optionally substituted 3- to 8-membered heterocycloalkyl, or an optionally substituted 5- to 9-membered heteroaryl; and
Y is 3- to 8-membered heterocycloalkyl, $C_6$-$C_{10}$ aryl, or 5- to 9-membered heteroaryl, wherein the 3- to 8-membered heterocycloalkyl, $C_6$-$C_{10}$ aryl, or 5- to 9-membered heteroaryl is optionally substituted with one, two, or three of any of $C_1$-$C_6$ haloalkyl, $C_3$-$C_8$ cycloalkyl, halo, cyano, or —$R^4OR^5$.

In some embodiments, the compound of formula (II) is a compound of formula (II-g):

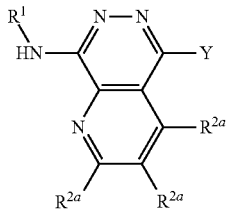

(II-g)

and pharmaceutically acceptable salts, solvates, clathrates, hydrates, stereoisomers, or tautomers thereof, wherein:
$R^{2a}$, $R^4$, and $R^5$ are described herein as set forth in Formula II;
$R^1$ is $C_1$-$C_6$ alkyl substituted with one more halo, —$R^4OR^5$, an optionally substituted 3- to 8-membered heterocycloalkyl, or an optionally substituted 5- to 9-membered heteroaryl; and
Y is 3- to 8-membered heterocycloalkyl, $C_6$-$C_{10}$ aryl, or 5- to 9-membered heteroaryl, wherein the 3- to 8-membered heterocycloalkyl, $C_6$-$C_{10}$ aryl, or 5- to 9-membered heteroaryl is optionally substituted with one, two, or three of any of $C_1$-$C_6$ haloalkyl, $C_3$-$C_8$ cycloalkyl, halo, cyano, or —$R^4OR^5$.

In some embodiments, the compound of formula (II) is a compound of formula (II-h):

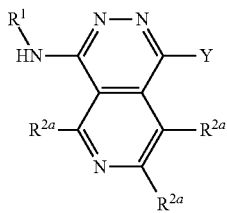

(II-h)

and pharmaceutically acceptable salts, solvates, clathrates, hydrates, stereoisomers, or tautomers thereof, wherein:
each $R^{2a}$ is hydrogen or deuterium;
$R^1$ is $C_1$-$C_6$ alkyl, —$(CH_2)_n$—$(C_3$-$C_{10}$ cycloalkyl), —$(CH_2)_n$—$(C_6$-$C_{10}$ aryl), —$(CH_2)_n$-(3- to 8-membered heterocycloalkyl), or —$(CH_2)_n$-(5- to 9-membered heteroaryl), wherein the alkyl, cycloalkyl, aryl, heterocycloalkyl, or heteroaryl is optionally substituted with one or more halo, CN, $C_1$-$C_6$ alkyl, $C_6$-$C_{10}$ aryl, —$NR^5R^6$, or —$R^4OR^5$; and
Y is $C_6$-$C_{10}$ aryl, wherein the aryl is optionally substituted with one or more halo, $C_1$-$C_6$ alkyl, $C_1$-$C_6$ haloalkyl, or —$R^4OR^5$.
$R^4$ is a bond, $C_1$-$C_6$ alkyl, $C_2$-$C_6$ alkenyl, or $C_2$-$C_6$ alkynyl;
$R^5$ and $R^6$ independently are hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl, wherein the alkyl is optionally substituted with one or more D; and
n is an integer from 0 to 4. In some embodiments, the compound of formula (I) is a compound of formula (II-i):

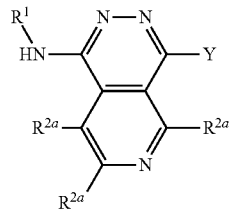

(II-i)

and pharmaceutically acceptable salts, solvates, clathrates, hydrates, stereoisomers, or tautomers thereof, wherein:
$R^{2a}$, $R^4$, and $R^5$ are described herein as set forth in Formula II;
$R^1$ is $C_1$-$C_6$ alkyl substituted with one more halo, —$R^4OR^5$, an optionally substituted 3- to 8-membered heterocycloalkyl, or an optionally substituted 5- to 9-membered heteroaryl; and
Y is 3- to 8-membered heterocycloalkyl, $C_6$-$C_{10}$ aryl, or 5- to 9-membered heteroaryl, wherein the 3- to 8-membered heterocycloalkyl, $C_6$-$C_{10}$ aryl, or 5- to 9-membered heteroaryl is optionally substituted with one, two, or three of any of $C_1$-$C_6$ haloalkyl, $C_3$-$C_8$ cycloalkyl, halo, cyano, or —$R^4OR^5$.

In some embodiments the compound of formula II is a compound of formula (II-j):

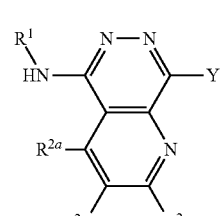

(II-j)

and pharmaceutically acceptable salts, solvates, clathrates, hydrates, stereoisomers, or tautomers thereof, wherein:
$R^{2a}$, $R^4$, and $R^5$ are described herein as set forth in Formula II;
$R^1$ is $C_1$-$C_6$ alkyl substituted with one more halo, —$R^4OR^5$, an optionally substituted 3- to 8-membered heterocycloalkyl, or an optionally substituted 5- to 9-membered heteroaryl; and
Y is 3- to 8-membered heterocycloalkyl, $C_6$-$C_{10}$ aryl, or 5- to 9-membered heteroaryl, wherein the 3- to 8-membered heterocycloalkyl, $C_6$-$C_{10}$ aryl, or 5- to 9-membered heteroaryl is optionally substituted with one, two, or three of any of $C_1$-$C_6$ haloalkyl, $C_3$-$C_8$ cycloalkyl, halo, cyano, or —$R^4OR^5$.

Variables X, Y, $R^a$, $R^b$, and $R^c$
In some embodiments, X is $N(R^a)$, O, S or $C(R^b)(R^c)$.
In some embodiments, X is $N(R^a)$.
In some embodiments, X is O.
In some embodiments, X is S.
In some embodiments, X is $C(R^b)(R^c)$.
In some embodiments, $R^a$ is H.
In some embodiments, $R^a$ is $C_1$-$C_6$ alkyl. In some embodiments, $R^1$ is methyl.
In some embodiments, Y is 3- to 8-membered heterocycloalkyl, $C_6$-$C_{10}$ aryl, or 5- to 9-membered heteroaryl, wherein the 3- to 8-membered heterocycloalkyl, $C_6$-$C_{10}$ aryl, or 5- to 9-membered heteroaryl is optionally substituted with one or more $C_1$-$C_6$ alkyl, $C_1$-$C_6$ haloalkyl, $C_3$-$C_8$ cycloalkyl, halo, cyano, or —$R^4OR^5$.

In some embodiments, Y is 3- to 8-membered heterocycloalkyl, $C_6$-$C_{10}$ aryl, or 5- to 9-membered heteroaryl, wherein the 3- to 8-membered heterocycloalkyl, $C_6$-$C_{10}$ aryl, or 5- to 9-membered heteroaryl is substituted with one or more $C_1$-$C_6$ alkyl, $C_1$-$C_6$ haloalkyl, $C_3$-$C_8$ cycloalkyl, halo, cyano, or —$R^4OR^5$.

In some embodiments, Y is 3- to 8-membered heterocycloalkyl, $C_6$-$C_{10}$ aryl, or 5- to 9-membered heteroaryl, wherein the 3- to 8-membered heterocycloalkyl, $C_6$-$C_{10}$ aryl, or 5- to 9-membered heteroaryl is substituted with one $C_1$-$C_6$ alkyl, $C_1$-$C_6$ haloalkyl, $C_3$-$C_8$ cycloalkyl, halo, cyano, or —$R^4OR^5$.

In some embodiments, Y is 3- to 8-membered heterocycloalkyl, $C_6$-$C_{10}$ aryl, or 5- to 9-membered heteroaryl, wherein the 3- to 8-membered heterocycloalkyl, $C_6$-$C_{10}$ aryl, or 5- to 9-membered heteroaryl is substituted with two of $C_1$-$C_6$ alkyl, $C_1$-$C_6$ haloalkyl, $C_3$-$C_8$ cycloalkyl, halo, cyano, or —$R^4OR^5$.

In some embodiments, Y is 3- to 8-membered heterocycloalkyl, $C_6$-$C_{10}$ aryl, or 5- to 9-membered heteroaryl, wherein the 3- to 8-membered heterocycloalkyl, $C_6$-$C_{10}$ aryl, or 5- to 9-membered heteroaryl is substituted with three of $C_1$-$C_6$ alkyl, $C_1$-$C_6$ haloalkyl, $C_3$-$C_8$ cycloalkyl, halo, cyano, or —$R^4OR^5$.

In some embodiments, Y is 3- to 8-membered heterocycloalkyl substituted with one or more $C_1$-$C_6$ alkyl, $C_1$-$C_6$ haloalkyl, $C_3$-$C_8$ cycloalkyl, halo, cyano, or —$R^4OR^5$. In some embodiments, Y is piperidinyl substituted with one or more $C_1$-$C_6$ alkyl, $C_1$-$C_6$ haloalkyl, $C_3$-$C_8$ cycloalkyl, halo, cyano, or —$R^4OR^5$.

In some embodiments, Y is $C_6$-$C_{10}$ aryl substituted with one or more $C_1$-$C_6$ alkyl, $C_1$-$C_6$ haloalkyl, $C_3$-$C_8$ cycloalkyl, halo, cyano, or —$R^4OR^5$. In some embodiments, Y is phenyl substituted with one or more $C_1$-$C_6$ alkyl, $C_1$-$C_6$ haloalkyl, $C_3$-$C_8$ cycloalkyl, halo, cyano, or —$R^4OR^5$.

In some embodiments, Y is 5- to 9-membered heteroaryl substituted with one or more $C_1$-$C_6$ alkyl, $C_1$-$C_6$ haloalkyl, $C_3$-$C_8$ cycloalkyl, halo, cyano, or —$R^4OR^5$. In some embodiments, Y is pyridyl substituted with one or more $C_1$-$C_6$ alkyl, $C_1$-$C_6$ haloalkyl, $C_3$-$C_8$ cycloalkyl, halo, cyano, or —$R^4OR^5$.

In some embodiments, Y is $C_6$-$C_{10}$ aryl optionally with one or more $C_1$-$C_6$ alkyl, $C_1$-$C_6$ haloalkyl, $C_3$-$C_8$ cycloalkyl, halo, cyano, or —$R^4OR^5$.

In some embodiments, —Y is phenyl optionally with one or more $C_1$-$C_6$ alkyl, $C_1$-$C_6$ haloalkyl, $C_3$-$C_8$ cycloalkyl, halo, cyano, or —$R^4OR^5$ In some embodiments, Y is

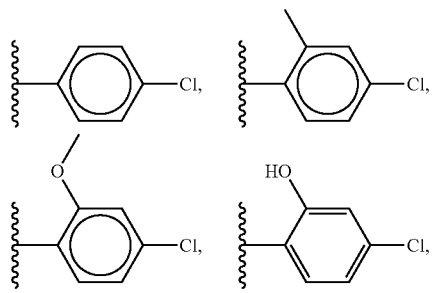

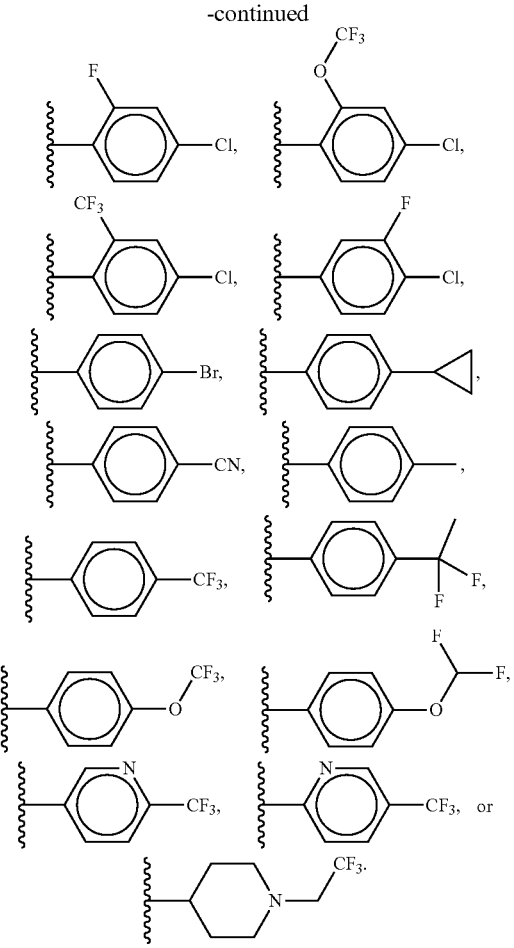

In some embodiments, Y is

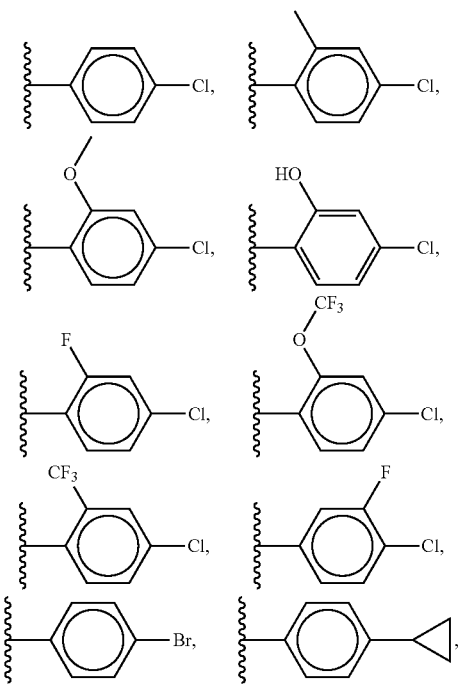

-continued

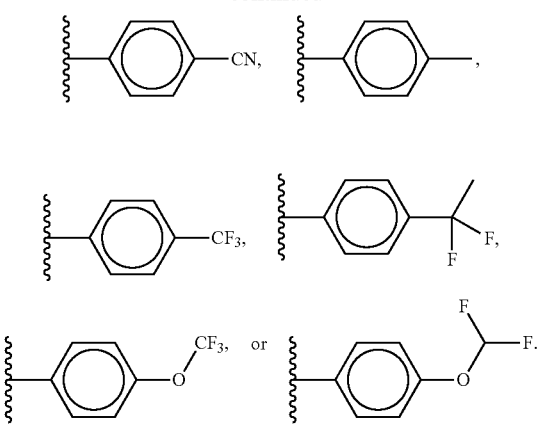

In some embodiments Y is

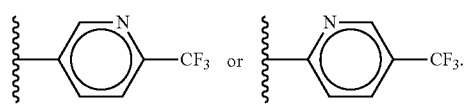

In some embodiments, Y is

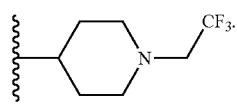

Variables R, $R^{2a}$, and $R^3$

In some embodiments, $R^2$ is hydrogen.

In some embodiments, $R^2$ is $C_1$-$C_6$ alkyl. In some embodiments, $R^2$ is methyl.

In some embodiments, $R^3$ is hydrogen.

In some embodiments, $R^3$ is $C_1$-$C_6$ alkyl. In some embodiments, $R^3$ is methyl.

In some embodiments, $R^3$ is $C_1$-$C_6$ alkyl substituted with one or more halo. In some embodiments, $R^3$ is $CF_3$.

In some embodiments, $R^2$ and $R^3$, together with the atoms to which they are attached, form a $C_3$-$C_8$ cycloalkyl, $C_6$-$C_{10}$ aryl, or 5- to 9-membered heteroaryl, wherein the $C_3$-$C_8$ cycloalkyl, $C_6$-$C_{10}$ aryl, or 5- to 9-membered heteroaryl is optionally substituted with one or more $R^2$.

In some embodiments, $R^2$ and $R^3$, together with the atoms to which they are attached, form a $C_3$-$C_8$ cycloalkyl, $C_6$-$C_{10}$ aryl, or 5- to 9-membered heteroaryl, wherein the $C_3$-$C_8$ cycloalkyl, $C_6$-$C_{10}$ aryl, or 5- to 9-membered heteroaryl is substituted with one or more $R^{2a}$.

In some embodiments, $R^2$ and $R^3$, together with the atoms to which they are attached, form a $C_3$-$C_8$ cycloalkyl, $C_6$-$C_{10}$ aryl, or 5- to 9-membered heteroaryl, wherein the $C_3$-$C_8$ cycloalkyl, $C_6$-$C_{10}$ aryl, or 5- to 9-membered heteroaryl is substituted with one $R^{2'}$.

In some embodiments, $R^{2a}$ is hydrogen or deuterium.

In some embodiments, $R^{2a}$ is halo. In some embodiments, $R^{2a}$ is Cl.

In some embodiments, $R^2$ and $R^3$, together with the atoms to which they are attached, form

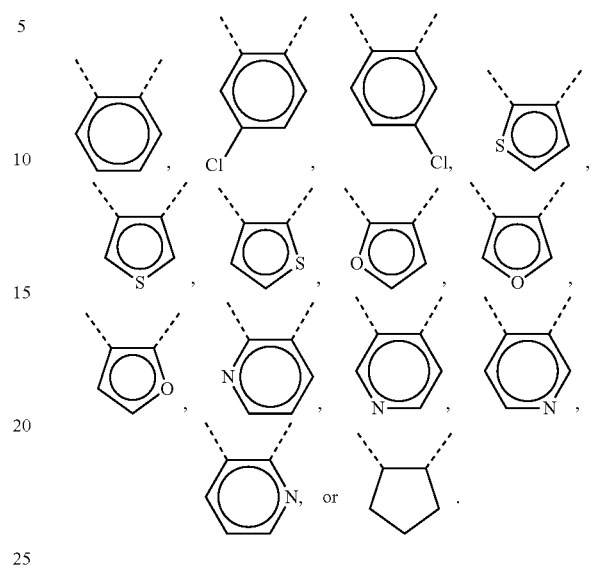

In some embodiments, $R^2$ and $R^3$, together with the atoms to which they are attached, form

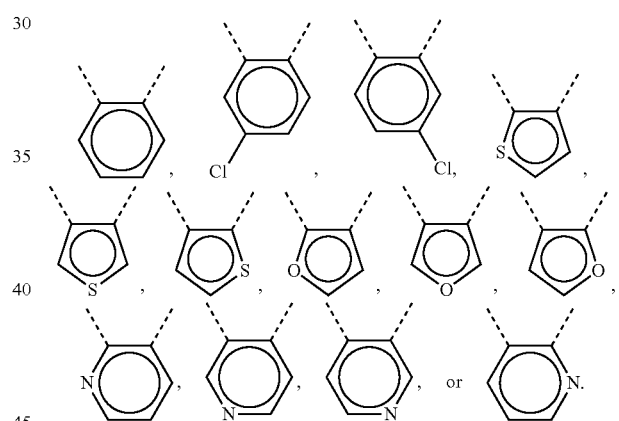

In some embodiments, $R^2$ and $R^3$, together with the atoms to which they are attached, form

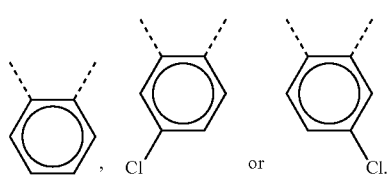

In some embodiments, $R^2$ and $R^3$, together with the atoms to which they are attached, form

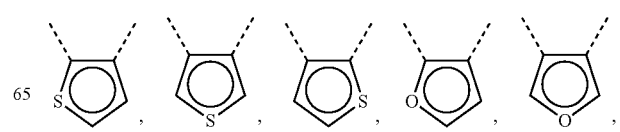

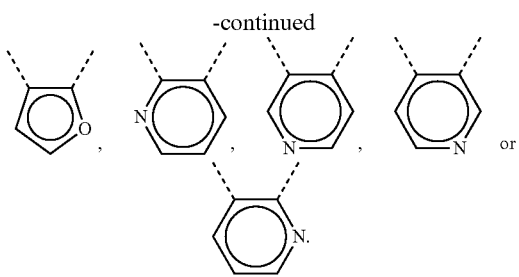

In some embodiments, $R^2$ and $R^3$, together with the atoms to which they are attached, form

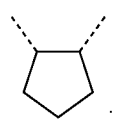

Variables R1, R4, R5, R6, R7, R7, R8, and t

In some embodiments, $R^1$ is $C_1$-$C_6$ alkyl, $C_2$-$C_6$ alkenyl, $C_2$-$C_6$ alkynyl, $C_1$-$C_6$ haloalkyl, —$(CH_2)_n$—$(C_3$-$C_{10}$ cycloalkyl), —$(CH_2)_n$-(3- to 8-membered heterocycloalkyl), —$(CH_2)_n$—$(C_6$-$C_{10}$ aryl), —$(CH_2)_n$-(5- to 9-membered heteroaryl), —$R^4SR^6$, —$R^4C(O)OR$, —$R^4C(O)N(R^7)(R^8)$, —$R^4S(O)_tR^5$, —$R^4S(O)_tN(R^7)(R^8)$, —$R^4P(O)(R^5)_2$, or —$R^4SF_5$ wherein the $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl is optionally substituted with one more halo, CN, $C_1$-$C_6$ alkyl, —$R^4OR^5$, —$NR^5SR^6$, an optionally substituted 3- to 8-membered heterocycloalkyl, an optionally substituted $C_6$-$C_{10}$ aryl, or an optionally substituted 5- to 9-membered heteroaryl.

In some embodiments, $R^1$ is $C_1$-$C_6$ alkyl, —$(CH_2)_n$—$(C_3$-$C_{10}$ cycloalkyl), —$(CH_2)_n$—$(C_6$-$C_{10}$ aryl), —$(CH_2)_n$-(3- to 8-membered heterocycloalkyl), or —$(CH_2)_n$-(5- to 9-membered heteroaryl), wherein the alkyl, cycloalkyl, aryl, heterocycloalkyl, or heteroaryl is optionally substituted with one or more halo, CN, $C_1$-$C_6$ alkyl, $C_6$-$C_{10}$ aryl, —$NR^5SR^6$, or —$R^4OR^5$.

In some embodiments, wherein $R^1$ is —$(CH_2)_n$—$(C_3$-$C_{10}$ cycloalkyl) optionally substituted with one or more halo, $C_1$-$C_6$ alkyl, or —$R^4OR^5$.

In some embodiments, $R^1$ is —$(CH_2)_n$-(3- to 8-membered heterocycloalkyl) optionally substituted with one or more halo, $C_1$-$C_6$ alkyl, or —$R^4OR^5$.

In some embodiments, $R^1$ is $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one more halo, —$R^4OR^5$, an optionally substituted 3- to 8-membered heterocycloalkyl, an optionally substituted $C_6$-$C_{10}$ aryl, or an optionally substituted 5- to 9-membered heteroaryl.

In some embodiments, $R^1$ is $C_1$-$C_6$ alkyl optionally substituted with one more halo, —$R^4OR^5$, an optionally substituted 3- to 8-membered heterocycloalkyl, an optionally substituted $C_6$-$C_{10}$ aryl, or an optionally substituted 5- to 9-membered heteroaryl.

In some embodiments, $R^1$ is 3- to 8-membered heterocycloalkyl optionally substituted with one more halo, —$R^4OR^5$, an optionally substituted 3- to 8-membered heterocycloalkyl, an optionally substituted $C_6$-$C_{10}$ aryl, or an optionally substituted 5- to 9-membered heteroaryl.

In some embodiments, $R^1$ is 3- to 8-membered heterocycloalkyl. In some embodiments, $R^1$ is tetrahydrofuranyl.

In some embodiments, $R^1$ is 5- to 9-membered heteroaryl optionally substituted with one more halo, —$R^4OR^5$, an optionally substituted 3- to 8-membered heterocycloalkyl, an optionally substituted $C_6$-$C_{10}$ aryl, or an optionally substituted 5- to 9-membered heteroaryl.

In some embodiments, $R^1$ is 5- to 9-membered heteroaryl. In some embodiments, $R^1$ is furanyl.

In some embodiments, $R^1$ is $C_1$-$C_6$ alkyl optionally substituted with one or more CN, $C_1$-$C_6$ alkyl, or —$R^4OR^5$.

In some embodiments, $R^1$ is $C_1$-$C_6$ alkyl optionally substituted with one or more CN, $C_1$-$C_6$ alkyl, or —$R^4OR^5$.

$R^1$ is $C_1$-$C_6$ alkyl optionally substituted with one or more CN, $C_1$-$C_6$ alkyl, or —$R^4OR^5$ In some embodiments, $R^1$ is

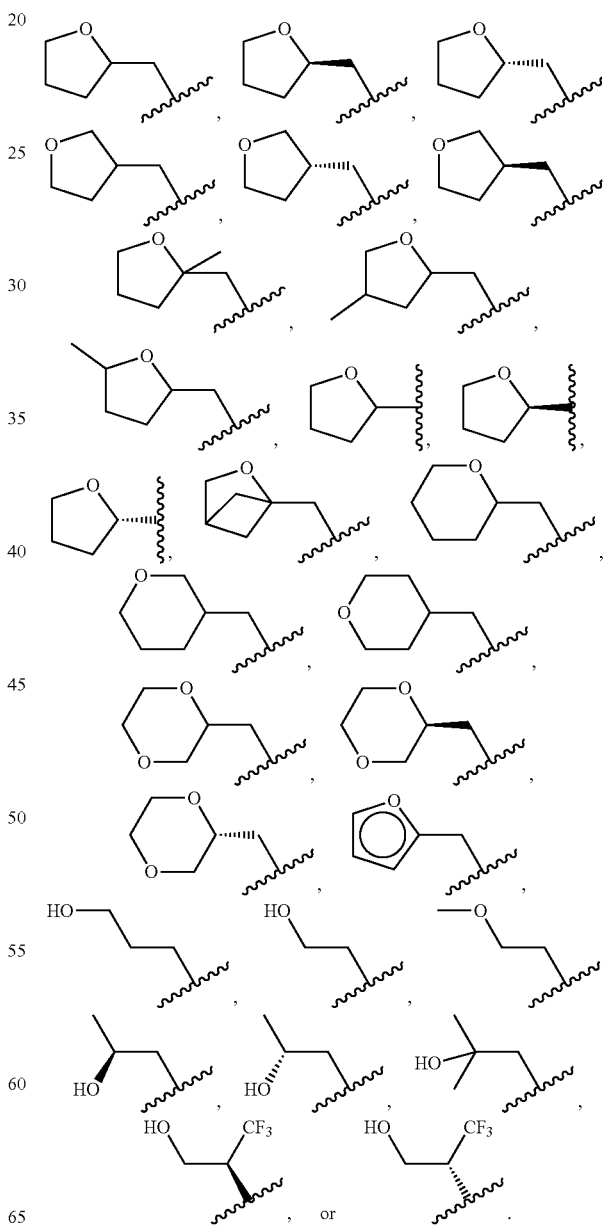

In some embodiments, $R^1$ is

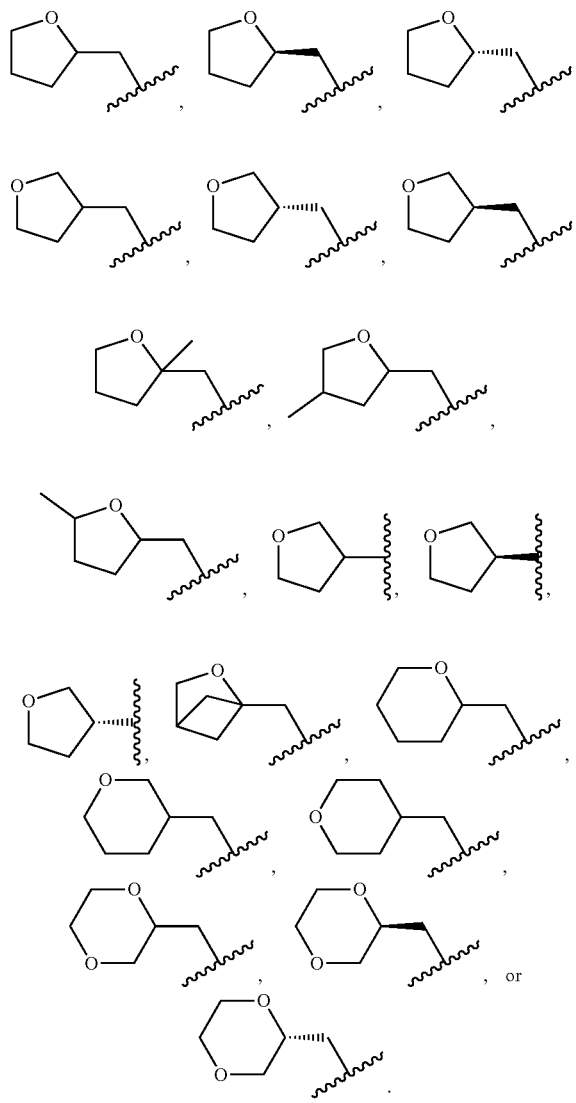

In some embodiments, $R^1$ is

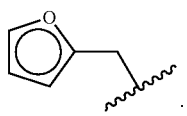

In some embodiments, $R^1$ is

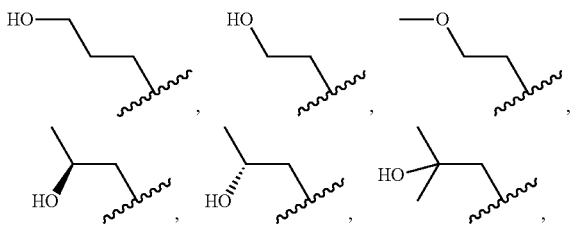

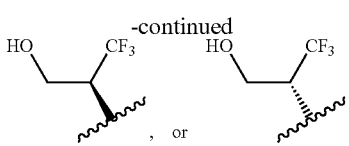
, or
.

In some embodiments, $R^4$ is a bond, $C_1$-$C_6$ alkyl, $C_2$-$C_6$ alkenyl, or $C_2$-$C_6$ alkynyl. In some embodiments, $R^4$ is a bond.

In some embodiments, $R^5$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl. In some embodiments, $R^5$ is hydrogen. In some embodiments, $R^5$ is $C_1$-$C_6$ alkyl. In some embodiments, $R^5$ is methyl.

In some embodiments, $R^6$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl.

In some embodiments, $R^7$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl.

In some embodiments, $R^8$ is hydrogen, $C_1$-$C_6$ alkyl, $C_1$-$C_6$ haloalkyl, $C_3$-$C_8$ cycloalkyl, 3- to 8-membered heterocycloalkyl, $C_6$-$C_{10}$ aryl, or 5- to 9-membered heteroaryl; or $R^7$ and $R^8$, together with the atoms to which they are attached, form a 3- to 8-membered heterocycloalkyl.

In some embodiments, t is 1 or 2. In some embodiments, t is 1. In some embodiments, t is 2.

In some embodiments, $R^1$ is not $C_1$-$C_6$ alkyl substituted with morpholinyl.

In some embodiments, $R^1$ is not $C_1$-$C_3$ alkyl substituted with morpholinyl.

In some embodiments, $R^1$ is not $C_2$ alkyl substituted with morpholinyl.

In some embodiments, $R^1$ is not $C_4$ alkyl substituted with morpholinyl.

In some embodiments, $R^1$ is not

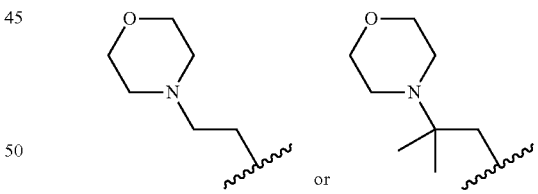

In some embodiments, n is 0. In other embodiments, n is 1. In other embodiments, n is 2. In other embodiments, n is 3. In other embodiments, n is 4.

In some embodiments, the compound is selected from the compounds described in Table 1 and pharmaceutically acceptable salts, solvates, clathrates, hydrates, and stereoisomers thereof.

In some embodiments, the compound is selected from the compounds described in Table 1 and pharmaceutically acceptable thereof.

In some embodiments, the compound is selected from the compounds described in Table 1.

TABLE 1

| Listing of Compounds. | | |
|---|---|---|
| Cmp. # | Structure | MS (ESI; m/z; M + H) |
| 1 | (S)-1-(4-chlorophenyl)-N-((tetrahydrofuran-2-yl)methyl)pyrido[3,4-d]pyridazin-4-amine | 341.1 |
| 2 | (S)-4-(4-chlorophenyl)-N-((tetrahydrofuran-2-yl)methyl)pyrido[3,4-d]pyridazin-1-amine | 341.2 |
| 3 | (R)-1-(4-chlorophenyl)-4-((tetrahydrofuran-2-yl)methoxy)pyrido[3,4-d]pyridazine | 342.0 |
| 4 | (R)-4-(4-chlorophenyl)-1-((tetrahydrofuran-2-yl)methoxy)pyrido[3,4-d]pyridazine | 342.0 |
| 5 | 4-(4-chlorophenyl)-N-(tetrahydrofuran-2-ylmethyl)phthalazin-1-amine | 342.2 |

TABLE 1-continued

Listing of Compounds.

| Cmp. # | Structure | MS (ESI; m/z; M + H) |
|---|---|---|
| 6 | 6-(4-bromophenyl)-N-[(2-methyltetrahydrofuran-2-yl)methyl]pyridazin-3-amine | 349.9 |
| 7 | 4-(4-bromophenyl)-N-(tetrahydrofuran-2-ylmethyl)phthalazin-1-amine | 386.1 |
| 8 | 4-(4-chlorophenyl)-N-[(2-methyltetrahydrofuran-2-yl)methyl]phthalazin-1-amine | 354.3 |
| 9 | 4-(4-chlorophenyl)-N-(tetrahydropyran-3-ylmethyl)phthalazin-1-amine | 356.2 |
| 10 | 4-(4-chlorophenyl)-N-(tetrahydropyran-4-ylmethyl)phthalazin-1-amine | 356.1 |

TABLE 1-continued

Listing of Compounds.

| Cmp. # | Structure | MS (ESI; m/z; M + H) |
|---|---|---|
| 11 | N-(tetrahydrofuran-2-ylmethyl)-4-[4-(trifluoromethyl)phenyl]phthalazin-1-amine | 375.3 |
| 12 | 4-(4-chlorophenyl)-N-[[rac-(2R)-tetrahydrofuran-2-yl]methyl]phthalazin-1-amine | 340.1 |
| 13 | 4-(4-chlorophenyl)-N-[[rac-(2S)-tetrahydrofuran-2-yl]methyl]phthalazin-1-amine | 340.2 |
| 14 | 1-(4-chlorophenyl)-N-(tetrahydrofuran-2-ylmethyl)pyrido[3,4-d]pyridazin-4-amine | 341.1 |
| 15 | 4-(4-chlorophenyl)-N-(tetrahydrofuran-2-ylmethyl)pyrido[3,4-d]pyridazin-1-amine | 341.2 |

TABLE 1-continued

Listing of Compounds.

| Cmp. # | Structure | MS (ESI; m/z; M + H) |
|---|---|---|
| 16 | 2-[[4-(4-chlorophenyl)phthalazin-1-yl]amino]ethanol | 302.1 |
| 17 | 4-(4-chlorophenyl)-N-(tetrahydropyran-2-ylmethyl)phthalazin-1-amine | 356.1 |
| 18 | 4-(4-chlorophenyl)-N-(2-methoxyethyl)phthalazin-1-amine | 315.9 |
| 19 | 4-(4-chlorophenyl)-N-methyl-N-(tetrahydrofuran-2-ylmethyl)phthalazin-1-amine | 354.1 |
| 20 | 4-(4-chloro-2-methyl-phenyl)-N-(tetrahydrofuran-2-ylmethyl)phthalazin-1-amine | 354.2 |

TABLE 1-continued

Listing of Compounds.

| Cmp. # | Structure | MS (ESI; m/z; M + H) |
|---|---|---|
| 21 | 7-chloro-4-(4-chlorophenyl)-N-[[rac-(2R)-tetrahydrofuran-2-yl]methyl]phthalazin-1-amine | 374.2 |
| 22 | 4-(4-chlorophenyl)-N-[(4-methyltetrahydrofuran-2-yl)methyl]phthalazin-1-amine | 356.0 |
| 23 | (R)-N-((1,4-dioxan-2-yl)methyl)-4-(4-chlorophenyl)phthalazin-1-amine | 356.3 |
| 24 | (S)-N-((1,4-dioxan-2-yl)methyl)-4-(4-chlorophenyl)phthalazin-1-amine | 356.1 |
| 25 | 4-(4-chlorophenyl)-N-[(5-methyltetrahydrofuran-2-yl)methyl]phthalazin-1-amine | 354.1 |

TABLE 1-continued

Listing of Compounds.

| Cmp. # | Structure | MS (ESI; m/z; M + H) |
|---|---|---|
| 26 | 7-chloro-4-(4-chlorophenyl)-N-[[rac-(2S)-tetrahydrofuran-2-yl]methyl]phthalazin-1-amine | 374 |
| 27 | 5-(4-chlorophenyl)-N-(tetrahydrofuran-2-ylmethyl)pyrido[2,3-d]pyridazin-8-amine | 341 |
| 28 | 8-(4-chlorophenyl)-N-(tetrahydrofuran-2-ylmethyl)pyrido[2,3-d]pyridazin-5-amine | 341.1 |
| 29 | N-(tetrahydrofuran-2-ylmethyl)-4-[6-(trifluoromethyl)-3-pyridyl]phthalazin-1-amine | 375.1 |
| 30 | 4-(4-chlorophenyl)-N-(tetrahydrofuran-3-ylmethyl)phthalazin-1-amine | 342.0 |

TABLE 1-continued

Listing of Compounds.

| Cmp. # | Structure | MS (ESI; m/z; M + H) |
|---|---|---|
| 31 | N-(tetrahydrofuran-2-ylmethyl)-1-[4-(trifluoromethyl)phenyl]pyrido[3,4-d]pyridazin-4-amine | 375.2 |
| 32 | N-(tetrahydrofuran-2-ylmethyl)-4-[4-(trifluoromethyl)phenyl]pyrido[3,4-d]pyridazin-1-amine | 375.2 |
| 33 | N-(tetrahydrofuran-2-ylmethyl)-4-[5-(trifluoromethyl)-2-pyridyl]phthalazin-1-amine | 375.1 |
| 34 | 1-(4-chlorophenyl)-N-[[rac-(2R)-tetrahydrofuran-2-yl]methyl]pyrido[3,4-d]pyridazin-4-amine | 341 |
| 35 | 1-[4-(1,1-difluoroethyl)phenyl]-N-[[rac-(2R)-tetrahydrofuran-2-yl]methyl]pyrido[3,4-d]pyridazin-4-amine | 371.4 |

TABLE 1-continued

Listing of Compounds.

| Cmp. # | Structure | MS (ESI; m/z; M + H) |
|---|---|---|
| 36 | N-[[rac-(2R)-tetrahydrofuran-2-yl]methyl]-1-[4-(trifluoromethoxy)phenyl]pyrido[3,4-d]pyridazin-4-amine | 391.1 |
| 37 | rac-(2R)-1-[[1-(4-chlorophenyl)pyrido[3,4-d]pyridazin-4-yl]amino]propan-2-ol | 315.1 |
| 38 | rac-(2S)-1-[[1-(4-chlorophenyl)pyrido[3,4-d]pyridazin-4-yl]amino]propan-2-ol | 315.1 |
| 39 | 1-(4-chlorophenyl)-N-(tetrahydropyran-4-ylmethyl)pyrido[3,4-d]pyridazin-4-amine | 355.1 |
| 40 | rac-(2R)-1-[[4-(4-chlorophenyl)pyrido[3,4-d]pyridazin-1-yl]amino]propan-2-ol | 315.1 |

TABLE 1-continued

Listing of Compounds.

| Cmp. # | Structure | MS (ESI; m/z; M + H) |
|---|---|---|
| 41 | 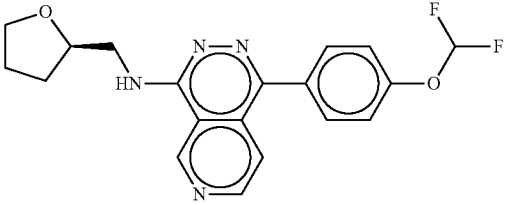 rac-(2S)-1-[[4-(4-chlorophenyl)pyrido[3,4-d]pyridazin-1-yl]amino]propan-2-ol | 315 |
| 42 | 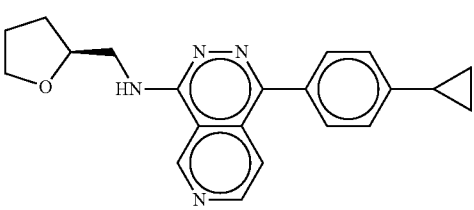 4-(4-chlorophenyl)-N-[[rac-(2R)-tetrahydrofuran-2-yl]methyl]pyrido[3,4-d]pyridazin-1-amine | 341.1 |
| 43 | 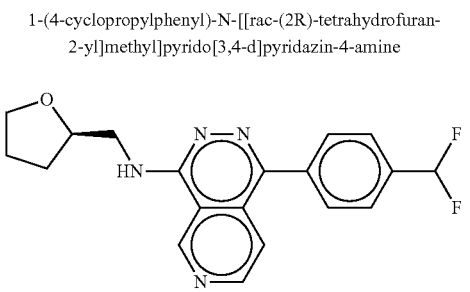 1-[4-(difluoromethoxy)phenyl]-N-[[rac-(2R)-tetrahydrofuran-2-yl]methyl]pyrido[3,4-d]pyridazin-4-amine | 373.2 |
| 44 | 1-(4-cyclopropylphenyl)-N-[[rac-(2R)-tetrahydrofuran-2-yl]methyl]pyrido[3,4-d]pyridazin-4-amine | 347.2 |
| 45 | 1-[4-(difluoromethyl)phenyl]-N-[[rac-(2R)-tetrahydrofuran-2-yl]methyl]pyrido[3,4-d]pyridazin-4-amine | 357.1 |

TABLE 1-continued

Listing of Compounds.

| Cmp. # | Structure | MS (ESI; m/z; M + H) |
|---|---|---|
| 46 | 1-[[1-(4-chlorophenyl)pyrido[3,4-d]pyridazin-4-yl]amino]-2-methyl-propan-2-ol | 329.1 |
| 47 | 1-(4-chloro-3-fluoro-phenyl)-N-[[rac-(2R)-tetrahydrofuran-2-yl]methyl]pyrido[3,4-d]pyridazin-4-amine | 359 |
| 48 | 1-(4-chloro-2-methoxy-phenyl)-N-[[rac-(2R)-tetrahydrofuran-2-yl]methyl]pyrido[3,4-d]pyridazin-4-amine | 371.1 |
| 49 | 4-(4-chlorophenyl)-N-(2-furylmethyl)pyrido[3,4-d]pyridazin-1-amine | 337 |
| 50 | 1-(4-chlorophenyl)-N-[[rac-(3R)-tetrahydropyran-3-yl]methyl]pyrido[3,4-d]pyridazin-4-amine | 355.1 |

TABLE 1-continued

Listing of Compounds.

| Cmp. # | Structure | MS (ESI; m/z; M + H) |
|---|---|---|
| 51 | 1-(4-chloro-2-fluoro-phenyl)-N-[[rac-(2R)-tetrahydrofuran-2-yl]methyl]pyrido[3,4-d]pyridazin-4-amine | 359.1 |
| 52 | 1-[4-chloro-2-(trifluoromethyl)phenyl]-N-[[rac-(2R)-tetrahydrofuran-2-yl]methyl]pyrido[3,4-d]pyridazin-4-amine | 409.2 |
| 53 | 1-(4-chlorophenyl)-N-(2-oxabicyclo[2.1.1]hexan-1-ylmethyl)pyrido[3,4-d]pyridazin-4-amine | 353.1 |
| 54 | 1-(4-chlorophenyl)-N-[[rac-(3R)-tetrahydrofuran-3-yl]methyl]pyrido[3,4-d]pyridazin-4-amine | 341.2 |
| 55 | 4-(4-chlorophenyl)-N-[[rac-(2R)-tetrahydrofuran-2-yl]methyl]thieno[2,3-d]pyridazin-7-amine | 346 |
| 56 | 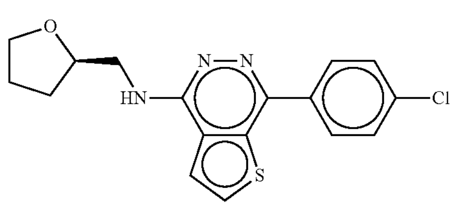 | 346.1 |

TABLE 1-continued

Listing of Compounds.

| Cmp. # | Structure | MS (ESI; m/z; M + H) |
|---|---|---|
| 57 | 7-(4-chlorophenyl)-N-[[rac-(2R)-tetrahydrofuran-2-yl]methyl]thieno[2,3-d]pyridazin-4-amine | 318.2 |
| 58 | 6-(4-chlorophenyl)-4,5-dimethyl-N-[[rac-(2R)-tetrahydrofuran-2-yl]methyl]pyridazin-3-amine | 353.1 |
| 59 | 4-(4-chlorophenyl)-N-(2-oxabicyclo[2.1.1]hexan-1-ylmethyl)pyrido[3,4-d]pyridazin-1-amine | 396.1 |
| 60 | N-[[rac-(2R)-tetrahydrofuran-2-yl]methyl]-1-[1-(2,2,2-trifluoroethyl)-4-piperidyl]pyrido[3,4-d]pyridazin-4-amine | 425.2 |
| 61 | 1-[4-chloro-2-(trifluoromethoxy)phenyl]-N-[[rac-(2R)-tetrahydrofuran-2-yl]methyl]pyrido[3,4-d]pyridazin-4-amine | 330 |
| | 4-(4-chlorophenyl)-N-[[rac-(2R)-tetrahydrofuran-2-yl]methyl]furo[2,3-d]pyridazin-7-amine | |

TABLE 1-continued

Listing of Compounds.

| Cmp. # | Structure | MS (ESI; m/z; M + H) |
|---|---|---|
| 62 | 1-(4-chlorophenyl)-N-[[rac-(3S)-tetrahydrofuran-3-yl]methyl]pyrido[3,4-d]pyridazin-4-amine | 341.1 |
| 63 | 1-(4-chlorophenyl)-N-[rac-(3S)-tetrahydrofuran-3-yl]pyrido[3,4-d]pyridazin-4-amine | 327.1 |
| 64 | 1-(4-chlorophenyl)-N-[rac-(3R)-tetrahydrofuran-3-yl]pyrido[3,4-d]pyridazin-4-amine | 327 |
| 65 | 3-[[1-(4-chlorophenyl)pyrido[3,4-d]pyridazin-4-yl]amino]propan-1-ol | 315.2 |
| 66 | 1-(4-chlorophenyl)-N-(tetrahydrofuran-2-ylmethyl)-6,7-dihydro-5H-cyclopenta[d]pyridazin-4-amine | 330.1 |

TABLE 1-continued

Listing of Compounds.

| Cmp. # | Structure | MS (ESI; m/z; M + H) |
|---|---|---|
| 67 | 4-(4-chlorophenyl)-N-[[rac-(3R)-tetrahydrofuran-3-yl]methyl]pyrido[3,4-d]pyridazin-1-amine | 341.1 |
| 68 | 4-(4-chlorophenyl)-N-[rac-(3S)-tetrahydrofuran-3-yl]pyrido[3,4-d]pyridazin-1-amine | 327.1 |
| 69 | 4-(4-chlorophenyl)-N-[rac-(3R)-tetrahydrofuran-3-yl]pyrido[3,4-d]pyridazin-1-amine | 327 |
| 70 | 3-[[4-(4-chlorophenyl)pyrido[3,4-d]pyridazin-1-yl]amino]propan-1-ol | 315.1 |
| 71 | 4-[4-[[rac-(2R)-tetrahydrofuran-2-yl]methylamino]pyrido[3,4-d]pyridazin-1-yl]benzonitrile | 332.3 |

TABLE 1-continued

Listing of Compounds.

| Cmp. # | Structure | MS (ESI; m/z; M + H) |
|---|---|---|
| 72 | 7-(4-chlorophenyl)-N-[[rac-(2R)-tetrahydrofuran-2-yl]methyl]furo[2,3-d]pyridazin-4-amine | 330 |
| 73 | rac-(2R)-2-[[1-(4-chlorophenyl)pyrido[3,4-d]pyridazin-4-yl]amino]-3,3,3-trifluoro-propan-1-ol | 369 |
| 74 | rac-(2S)-2-[[1-(4-chlorophenyl)pyrido[3,4-d]pyridazin-4-yl]amino]-3,3,3-trifluoro-propan-1-ol | 369.1 |
| 75 | 1-(4-chlorophenyl)-N-[[rac-(2R)-tetrahydrofuran-2-yl]methyl]thieno[3,4-d]pyridazin-4-amine | 346.1 |
| 76 | 6-(4-chlorophenyl)-N-[[rac-(2R)-tetrahydrofuran-2-yl]methyl]-5-(trifluoromethyl)pyridazin-3-amine | 358.2 |

TABLE 1-continued

Listing of Compounds.

| Cmp. # | Structure | MS (ESI; m/z; M + H) |
|---|---|---|
| 77 | 4-(4-chlorophenyl)-N-[[rac-(3S)-tetrahydrofuran-3-yl]methyl]pyrido[3,4-d]pyridazin-1-amine | 341.1 |
| 78 | 1-(4-chlorophenyl)-N-[[rac-(2S)-1,4-dioxan-2-yl]methyl]pyrido[3,4-d]pyridazin-4-amine | 357.2 |
| 79 | 1-(4-chlorophenyl)-N-[[rac-(2R)-1,4-dioxan-2-yl]methyl]pyrido[3,4-d]pyridazin-4-amine | 357.1 |
| 80 | 1-(p-tolyl)-N-[[rac-(2R)-tetrahydrofuran-2-yl]methyl]pyrido[3,4-d]pyridazin-4-amine | 321.3 |
| 81 | 4-(4-chlorophenyl)-N-[[rac-(2S)-1,4-dioxan-2-yl]methyl]pyrido[3,4-d]pyridazin-1-amine | 357.1 |

TABLE 1-continued

Listing of Compounds.

| Cmp. # | Structure | MS (ESI; m/z; M + H) |
|---|---|---|
| 82 | 5-chloro-2-(4-((2-hydroxy-2-methylpropyl)amino)pyrido[3,4-d]pyridazin-1-yl)phenol | 345.1 |
| 83 | 5-chloro-2-(4-((2-methoxy-2-methylpropyl)amino)pyrido[3,4-d]pyridazin-1-yl)phenol | 359.2 |
| 84 | 5-methoxy-2-(4-((2-methoxy-2-methylpropyl)amino)pyrido[3,4-d]pyridazin-1-yl)phenol | 355.0 |
| 85 | 2-(4-((2-methoxy-2-methylpropyl)amino)pyrido[3,4-d]pyridazin-1-yl)-5-methylphenol | 339.2 |
| 86 | 5-bromo-2-(4-((2-methoxy-2-methylpropyl)amino)pyrido[3,4-d]pyridazin-1-yl)phenol | 403.1 |

TABLE 1-continued

Listing of Compounds.

| Cmp. # | Structure | MS (ESI; m/z; M + H) |
|---|---|---|
| 87 | 2-(4-((2-methoxy-2-methylpropyl)amino)pyrido[3,4-d]pyridazin-1-yl)-5-(trifluoromethyl)phenol | 393.2 |
| 88 | 2-(4-((2-methoxy-2-methylpropyl)amino)pyrido[3,4-d]pyridazin-1-yl)-5-(trifluoromethoxy)phenol | 409.1 |
| 89 | (S)-5-chloro-2-(4-((tetrahydrofuran-3-yl)amino)pyrido[3,4-d]pyridazin-1-yl)phenol | 343.1 |
| 90 | 5-chloro-2-(4-((3-hydroxy-3-methylbutyl)amino)pyrido[3,4-d]pyridazin-1-yl)phenol | 359.0 |
| 91 | (S)-5-chloro-2-(4-(((3,3-difluorocyclopentyl)methyl)amino)pyrido[3,4-d]pyridazin-1-yl)phenol | 391.1 |

TABLE 1-continued

Listing of Compounds.

| Cmp. # | Structure | MS (ESI; m/z; M + H) |
|---|---|---|
| 92 | (S)-5-chloro-2-(4-(((tetrahydrofuran-3-yl)methyl)amino)pyrido[3,4-d]pyridazin-1-yl)phenol | 357.2 |
| 93 | (S)-5-chloro-2-(4-(((1-methylpyrrolidin-2-yl)methyl)amino)pyrido[3,4-d]pyridazin-1-yl)phenol | 370.2 |
| 94 | (R)-5-chloro-2-(4-(((3-fluorotetrahydrofuran-3-yl)methyl)amino)pyrido[3,4-d]pyridazin-1-yl)phenol | 375.1 |
| 95 | 5-chloro-2-(4-(((1S,2S)-2-hydroxycyclopentyl)amino)pyrido[3,4-d]pyridazin-1-yl)phenol | 357.0 |
| 96 | 5-chloro-2-(4-(((1-(hydroxymethyl)cyclopropyl)methyl)amino)pyrido[3,4-d]pyridazin-1-yl)phenol | 357.0 |

TABLE 1-continued

Listing of Compounds.

| Cmp. # | Structure | MS (ESI; m/z; M + H) |
|---|---|---|
| 97 | (R)-5-chloro-2-(4-((3,3,3-trifluoro-2-methoxypropyl)amino)pyrido[3,4-d]pyridazin-1-yl)phenol | 399.1 |
| 98 | (S)-5-chloro-2-(4-((1-methylpyrrolidin-3-yl)amino)pyrido[3,4-d]pyridazin-1-yl)phenol | 356.2 |
| 99 | 5-chloro-2-(4-((2-(methoxy-d3)-2-methylpropyl)amino)pyrido[3,4-d]pyridazin-1-yl)phenol | 362.0 |
| 100 | (R)-5-chloro-2-(4-((1-methoxypropan-2-yl)amino)pyrido[3,4-d]pyridazin-1-yl)phenol | 344.9 |
| 101 | (R)-5-chloro-2-(4-(((4-methylmorpholin-2-yl)methyl)amino)pyrido[3,4-d]pyridazin-1-yl)phenol | 386.2 |

TABLE 1-continued

Listing of Compounds.

| Cmp. # | Structure | MS (ESI; m/z; M + H) |
|---|---|---|
| 102 | 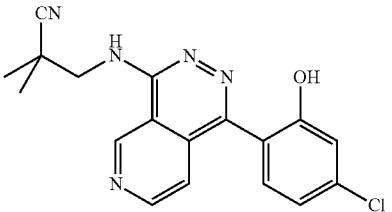 [SMILES: CC(C)(C#N)CNc1nnc(-c2ccc(Cl)cc2O)c2ccncc12]<br>3-((1-(4-chloro-2-hydroxyphenyl)pyrido[3,4-d]pyridazin-4-yl)amino)-2,2-dimethylpropanenitrile | 354.1 |
| 103 | 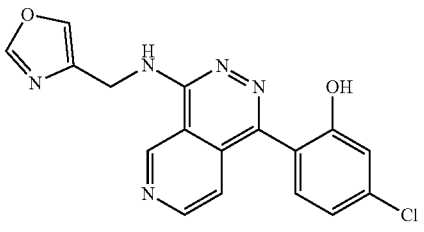 [SMILES: Oc1cc(Cl)ccc1-c1nnc(NCc2cocn2)c2cnccc12]<br>(R)-5-chloro-2-(4-(((4-methylmorpholin-2-yl)methyl)amino)pyrido[3,4-d]pyridazin-1-yl)phenol | 354.1 |
| 104 | 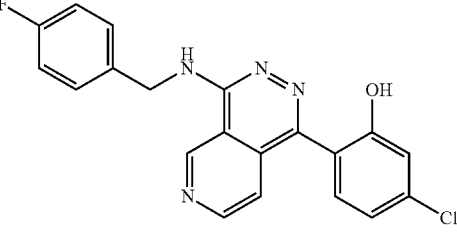<br>5-chloro-2-(4-((4-fluorobenzyl)amino)pyrido[3,4-d]pyridazin-1-yl)phenol | 381.1 |
| 105 | 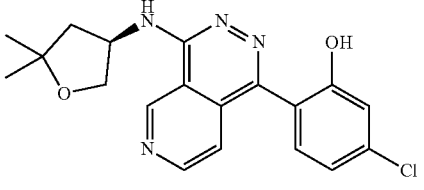 [SMILES: CC1(C)C[C@@H](Nc2nnc(-c3ccc(Cl)cc3O)c3ccncc23)CO1]<br>(R)-5-chloro-2-(4-((5,5-dimethyltetrahydrofuran-3-yl)amino)pyrido[3,4-d]pyridazin-1-yl)phenol | 371.1 |

In some embodiments, the compound is selected from the compounds described in Table 1.

In some embodiments, the compound is a pharmaceutically acceptable salt of any one of the compounds described in Table 1.

In some aspects, the present disclosure provides a compound being an isotopic derivative (e.g., isotopically labeled compound) of any one of the compounds of the Formulae disclosed herein.

In some embodiments, the compound is an isotopic derivative of any one of the compounds described in Table 1 and prodrugs and pharmaceutically acceptable salts thereof.

In some embodiments, the compound is an isotopic derivative of any one of the compounds described in Table 1 and pharmaceutically acceptable salts thereof.

In some embodiments, the compound is an isotopic derivative of any one of prodrugs of the compounds described in Table 1 and pharmaceutically acceptable salts thereof.

In some embodiments, the compound is an isotopic derivative of any one of the compounds described in Table 1.

It is understood that the isotopic derivative can be prepared using any of a variety of art-recognised techniques. For example, the isotopic derivative can generally be prepared by carrying out the procedures disclosed in the Schemes and/or in the Examples described herein, by substituting an isotopically labeled reagent for a non-isotopically labeled reagent.

In some embodiments, the isotopic derivative is a deuterium labeled compound.

In some embodiments, the isotopic derivative is a deuterium labeled compound of any one of the compounds of the Formulae disclosed herein.

The term "isotopic derivative", as used herein, refers to a derivative of a compound in which one or more atoms are isotopically enriched or labelled. For example, an isotopic derivative of a compound of Formula (I) is isotopically enriched with regard to, or labelled with, one or more isotopes as compared to the corresponding compound of Formula (I). In some embodiments, the isotopic derivative is enriched with regard to, or labelled with, one or more atoms selected from $^{2}H$, $^{13}C$, $^{14}C$, $^{15}N$, $^{18}O$, $^{29}Si$, $^{31}P$, and $^{34}S$. In some embodiments, the isotopic derivative is a deuterium labeled compound (i.e., being enriched with $^{2}H$ with regard to one or more atoms thereof). In some embodiments, the compound is a $^{18}F$ labeled compound. In some embodiments, the compound is a $^{123}I$ labeled compound, a $^{124}I$ labeled compound, a $^{125}I$ labeled compound, a $^{121}I$ labeled compound, a $^{131}I$ labeled compound, a $^{135}I$ labeled compound, or any combination thereof. In some embodiments, the compound is a $^{33}S$ labeled compound, a $^{34}S$ labeled compound, a $^{35}S$ labeled compound, a $^{36}S$ labeled compound, or any combination thereof.

It is understood that the $^{18}F$, $^{123}I$, $^{124}I$, $^{125}I$, $^{129}I$, $^{131}I$, $^{135}I$, $^{32}S$, $^{34}S$, $^{35}S$, and/or $^{36}S$ labeled compound, can be prepared using any of a variety of art-recognised techniques. For example, the deuterium labeled compound can generally be prepared by carrying out the procedures disclosed in the Schemes and/or in the Examples described herein, by substituting a $^{18}F$, $^{123}I$, $^{124}I$, $^{125}I$, $^{129}I$, $^{131}I$, $^{135}I$, $^{32}S$, $^{34}S$, $^{35}S$, and/or $^{36}S$ labeled reagent for a non-isotope labeled reagent.

A compound of the invention or a pharmaceutically acceptable salt or solvate thereof that contains one or more of the aforementioned $^{18}F$, $^{123}I$, $^{124}I$, $^{125}I$, $^{129}I$, $^{131}I$, $^{135}I$, $^{32}S$, $^{34}S$, $^{35}S$, and $^{36}S$ atom(s) is within the scope of the invention. Further, substitution with isotope (e.g., $^{18}F$, $^{123}I$, $^{124}I$, $^{125}I$, $^{129}I$, $^{131}I$, $^{135}I$, $^{32}S$, $^{34}S$, $^{35}S$, and/or $^{36}S$) may afford certain therapeutic advantages resulting from greater metabolic stability, e.g., increased in vivo half-life or reduced dosage requirements.

For the avoidance of doubt it is to be understood that, where in this specification a group is qualified by "described herein", the said group encompasses the first occurring and broadest definition as well as each and all of the particular definitions for that group.

A suitable pharmaceutically acceptable salt of a compound of the disclosure is, for example, an acid-addition salt of a compound of the disclosure which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the disclosure which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, diethylamine, trimethylamine, piperidine, morpholine or tris-(2-hydroxyethyl)amine.

It will be understood that the compounds of any one of the Formulae disclosed herein and any pharmaceutically acceptable salts thereof, comprise stereoisomers, mixtures of stereoisomers, polymorphs of all isomeric forms of said compounds.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral center" refers to a carbon atom bonded to four nonidentical substituents.

As used herein, the term "chiral isomer" means a compound with at least one chiral centre. Compounds with more than one chiral centre may exist either as an individual diastereomer or as a mixture of diastereomers, termed "diastereomeric mixture." When one chiral centre is present, a stereoisomer may be characterised by the absolute configuration (R or S) of that chiral centre. Absolute configuration refers to the arrangement in space of the substituents attached to the chiral centre. The substituents attached to the chiral centre under consideration are ranked in accordance with the Sequence Rule of Cahn, Ingold and Prelog. (Cahn et al., Angew. Chem. Inter. Edit. 1966, 5, 385; errata 511; Cahn et al., Angew. Chem. 1966, 78, 413; Cahn and Ingold, J. Chem. Soc. 1951 (London), 612; Cahn et al., Experientia 1956, 12, 81; Cahn, J. Chem. Educ. 1964, 41, 116).

As used herein, the term "geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

It is to be understood that the structures and other compounds discussed in this disclosure include all atropic isomers thereof. It is also to be understood that not all atropic isomers may have the same level of activity.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerisation is possible, a chemical equilibrium of the tautomers will be reached. The exact ratio of the tautomers depends on several factors, including temperature, solvent and pH. The concept of tautomers that are interconvertible by tautomerisations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups, a pair of enantiomers is possible. An enantiomer can be characterised by the absolute configuration of its asymmetric centre and is described by the R- and S-sequencing rules of Cahn and Prelog, or by the manner in which the molecule rotates the plane of polarised light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this disclosure may possess one or more asymmetric centres; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the disclosure may have geometric isomeric centres (E- and Z-isomers). It is to be understood that the present disclosure encompasses all optical, diastereoisomers and geometric isomers and mixtures thereof that possess inflammasome inhibitory activity.

It is to be understood that the compounds of any Formula described herein include the compounds themselves, as well as their salts, and their solvates, if applicable. A salt, for example, can be formed between an anion and a positively charged group (e.g., amino) on a substituted compound disclosed herein. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted compound disclosed herein. Suitable cations include sodium ion, potassium ion, magnesium ion, calcium ion, and an ammonium cation such as tetramethylammonium ion or diethylamine ion. The substituted compounds disclosed herein also include those salts containing quaternary nitrogen atoms.

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as H2O.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As used herein, the term "derivative" refers to compounds that have a common core structure and are substituted with various groups as described herein.

It is also to be understood that certain compounds of any one of the Formulae disclosed herein may exist in solvated as well as unsolvated forms such as, for example, hydrated forms. A suitable pharmaceutically acceptable solvate is, for example, a hydrate such as hemi-hydrate, a mono-hydrate, a di-hydrate or a tri-hydrate. It is to be understood that the disclosure encompasses all such solvated forms that possess inflammasome inhibitory activity.

It is also to be understood that certain compounds of any one of the Formulae disclosed herein may exhibit polymorphism, and that the disclosure encompasses all such forms, or mixtures thereof, which possess inflammasome inhibitory activity. It is generally known that crystalline materials may be analysed using conventional techniques such as X-Ray Powder Diffraction analysis, Differential Scanning Calorimetry, Thermal Gravimetric Analysis, Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

Compounds of any one of the Formulae disclosed herein may exist in a number of different tautomeric forms and references to compounds of Formula (I) include all such forms. For the avoidance of doubt, where a compound can exist in one of several tautomeric forms, and only one is specifically described or shown, all others are nevertheless embraced by Formula (I). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

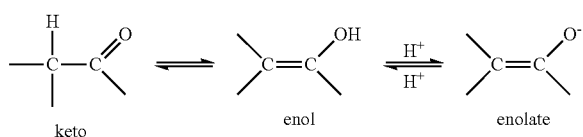

keto  enol  enolate

The compounds of any one of the Formulae disclosed herein may be administered in the form of a prodrug which is broken down in the human or animal body to release a compound of the disclosure. A prodrug may be used to alter the physical properties and/or the pharmacokinetic properties of a compound of the disclosure. A prodrug can be formed when the compound of the disclosure contains a suitable group or substituent to which a property-modifying group can be attached. Examples of prodrugs include derivatives containing in vivo cleavable alkyl or acyl substitutents at the ester or amide group in any one of the Formulae disclosed herein.

Accordingly, the present disclosure includes those compounds of any one of the Formulae disclosed herein as defined hereinbefore when made available by organic synthesis and when made available within the human or animal body by way of cleavage of a prodrug thereof. Accordingly, the present disclosure includes those compounds of any one of the Formulae disclosed herein that are produced by organic synthetic means and also such compounds that are produced in the human or animal body by way of metabolism of a precursor compound, that is a compound of any one of the Formulae disclosed herein may be a synthetically-produced compound or a metabolically-produced compound.

A suitable pharmaceutically acceptable prodrug of a compound of any one of the Formulae disclosed herein is one that is based on reasonable medical judgment as being suitable for administration to the human or animal body without undesirable pharmacological activities and without undue toxicity. Various forms of prodrug have been described, for example in the following documents: a) Methods in Enzymology, Vol. 42, p. 309-396, edited by K. Widder, et al. (Academic Press, 1985); b) Design of Pro-drugs, edited by H. Bundgaard, (Elsevier, 1985); c) A Textbook of Drug Design and Development, edited by Krogsgaard-Larsen and H. Bundgaard, Chapter 5 "Design and Application of Pro-drugs", by H. Bundgaard p. 113-191 (1991); d) H. Bundgaard, Advanced Drug Delivery Reviews, 8, 1-38 (1992); e) H. Bundgaard, et al., Journal of Pharmaceutical Sciences, 77, 285 (1988); f) N. Kakeya, et al., Chem. Pharm. Bull., 32, 692 (1984); g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

A suitable pharmaceutically acceptable prodrug of a compound of any one of the Formulae disclosed herein that possesses a hydroxy group is, for example, an in vivo cleavable ester or ether thereof. An in vivo cleavable ester or ether of a compound of any one of the Formulae disclosed herein containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_1$-$C_{10}$ alkanoyl groups such as acetyl, benzoyl, phenylacetyl and substituted benzoyl and phenylacetyl groups, $C_1$-$C_{10}$ alkoxycarbonyl groups such as ethoxycarbonyl, N,N—($C_1$-$C_6$ alkyl)2carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable prodrug of a compound of any one of the Formulae disclosed herein that possesses a carboxy group is, for example, an in vivo cleavable amide thereof, for example an amide formed with an amine such as ammonia, a $C_{1-4}$alkylamine such as methylamine, a ($C_1$-$C_4$ alkyl)$_2$-amine such as dimethylamine, N-ethyl-N-methylamine or diethylamine, a $C_1$-$C_4$ alkoxy-$C_2$-$C_4$ alkylamine such as 2-methoxyethylamine, a phenyl-$C_1$-$C_4$ alkylamine such as benzylamine and amino acids such as glycine or an ester thereof.

A suitable pharmaceutically acceptable prodrug of a compound of any one of the Formulae disclosed herein that possesses an amino group is, for example, an in vivo cleavable amide derivative thereof. Suitable pharmaceutically acceptable amides from an amino group include, for example an amide formed with $C_1$-$C_{10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl.

The in vivo effects of a compound of any one of the Formulae disclosed herein may be exerted in part by one or more metabolites that are formed within the human or animal body after administration of a compound of any one of the Formulae disclosed herein. As stated hereinbefore, the in vivo effects of a compound of any one of the Formulae disclosed herein may also be exerted by way of metabolism of a precursor compound (a prodrug).

A suitable general route for the preparation of a compound of the application can be described in Scheme 1 herein.

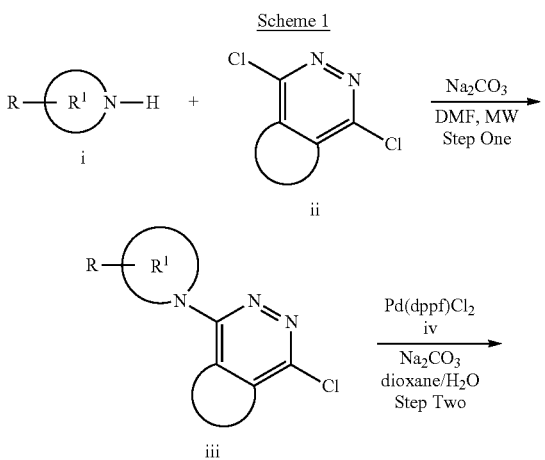

Scheme 1

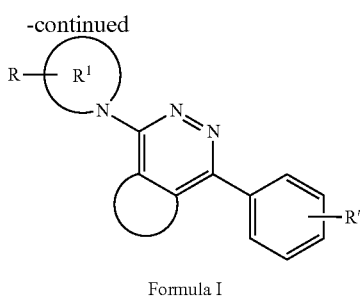

Formula I where R² and R³ are combined;
R represents substituents of R¹;
R′ represents substituents of Y;
R¹ is cyclic Examples presented herein, unless otherwise stated, are synthesized according to the general procedure presented in Scheme 1. Step One involves an $S_NAr$ reaction between an amine (i) and an aryl dichloride (ii), to provide the target chloroaryl intermediate (iii). Step Two involves cross-coupling between intermediate (iii) and the desired boronic acids or boronates iv to generate the desired compound of Formula I. Amines i, aryl dichlorides ii and boronic acids or boronates iv are either commercially available or known in the chemical literature, unless otherwise indicated.

Biological Assays

Compounds designed, selected and/or optimised by methods described above, once produced, can be characterised using a variety of assays known to those skilled in the art to determine whether the compounds have biological activity. For example, the molecules can be characterised by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described below.

Various in vitro or in vivo biological assays are may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, and the assays described herein.

In some embodiments, the biological assay is described in the Examples herein.

Pharmaceutical Compositions

In some aspects, the present disclosure provides a pharmaceutical composition comprising a compound of the present disclosure as an active ingredient. In some embodiments, the present disclosure provides a pharmaceutical composition comprising at least one compound of each of the formulae described herein, or a pharmaceutically acceptable salt or solvate thereof, and one or more pharmaceutically acceptable carriers or excipients. In some embodiments, the present disclosure provides a pharmaceutical composition comprising at least one compound selected from Table 1.

In one embodiment of the instant disclosure the pharmaceutical composition comprises a compound of Formula I as described herein and a pharmaceutically acceptable carrier.

In another embodiment of the disclosure, the pharmaceutical composition comprises a compound of Formula I' as described herein and a pharmaceutically acceptable carrier.

In another embodiment of the disclosure, the pharmaceutical composition comprises a compound of Formula I″ as described herein and a pharmaceutically acceptable carrier.

In another embodiment of the disclosure, the pharmaceutical composition comprises a compound of Formula II as described herein and a pharmaceutically acceptable carrier.

In one embodiment of the instant disclosure the pharmaceutical composition comprises a compound of Formula II-a as described herein and a pharmaceutically acceptable carrier.

In one embodiment of the instant disclosure the pharmaceutical composition comprises a compound of Formula II-b as described herein and a pharmaceutically acceptable carrier.

In one embodiment of the instant disclosure the pharmaceutical composition comprises a compound of Formula II-c as described herein and a pharmaceutically acceptable carrier.

In one embodiment of the instant disclosure the pharmaceutical composition comprises a compound of Formula II-d as described herein and a pharmaceutically acceptable carrier.

In one embodiment of the instant disclosure the pharmaceutical composition comprises a compound of Formula II-e as described herein and a pharmaceutically acceptable carrier.

In one embodiment of the instant disclosure the pharmaceutical composition comprises a compound of Formula II-f as described herein and a pharmaceutically acceptable carrier.

In one embodiment of the instant disclosure the pharmaceutical composition comprises a compound of Formula II-g as described herein and a pharmaceutically acceptable carrier.

In one embodiment of the instant disclosure the pharmaceutical composition comprises a compound of Formula II-h as described herein and a pharmaceutically acceptable carrier.

In one embodiment of the instant disclosure the pharmaceutical composition comprises a compound of Formula II-i as described herein and a pharmaceutically acceptable carrier.

In one embodiment of the instant disclosure the pharmaceutical composition comprises a compound of Formula II-j as described herein and a pharmaceutically acceptable carrier.

The compounds of present disclosure can be formulated for oral administration in forms such as tablets, capsules (each of which includes sustained release or timed release formulations), pills, powders, granules, elixirs, tinctures, suspensions, syrups and emulsions. The compounds of present disclosure on can also be formulated for intravenous (bolus or in-fusion), intraperitoneal, topical, subcutaneous, intramuscular or transdermal (e.g., patch) administration, all using forms well known to those of ordinary skill in the pharmaceutical arts.

The formulation of the present disclosure may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

Any suitable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulfated β-cyclodextrin (S-β-CD), maltosyl-β-cyclodextrin, β-cyclodextrin sulfobutyl ether, branched-β-cyclodextrin, hydroxypropyl-γ-cyclodextrin, randomly methylated-γ-cyclodextrin, and trimethyl-γ-cyclodextrin, and mixtures thereof.

Any suitable chelating agent can be used. Examples of a suitable chelating agent include those selected from the group consisting of ethylenediaminetetraacetic acid and metal salts thereof, disodium edetate, trisodium edetate, and tetrasodium edetate, and mixtures thereof.

Any suitable preservative can be used. Examples of a preservative include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, and sorbic acid, and mixtures thereof.

The aqueous vehicle may also include a tonicity agent to adjust the tonicity (osmotic pressure). The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof.

The aqueous vehicle may also contain a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof.

In order to adjust the formulation to an acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilise the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and ε-aminocaproic acid, and mixtures thereof.

The formulation may further comprise a wetting agent. Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavouring agent such as peppermint, methyl salicylate, or orange flavoring.

According to a further aspect of the disclosure there is provided a pharmaceutical composition which comprises a compound of the disclosure as defined hereinbefore, or a pharmaceutically acceptable salt, hydrate or solvate thereof, in association with a pharmaceutically acceptable diluent or carrier.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the disclosure may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present disclosure for use in therapy is an amount sufficient to treat or prevent an inflammasome related condition referred to herein, slow its progression and/or reduce the symptoms associated with the condition.

An effective amount of a compound of the present disclosure for use in therapy is an amount sufficient to treat an inflammasome related condition referred to herein, slow its progression and/or reduce the symptoms associated with the condition.

The size of the dose for therapeutic or prophylactic purposes of a compound of Formula (I) will naturally vary according to the nature and severity of the conditions, the age and sex of the animal or patient and the route of administration, according to well-known principles of medicine.

Methods of Use

In some aspects, the present disclosure provides a method of inhibiting NLRP3 activity (e.g., in vitro or in vivo), comprising contacting a cell with an effective amount of a compound of the present disclosure or a pharmaceutically acceptable salt thereof.

In some aspects, the present disclosure provides a method of treating or preventing a disease or disorder inhibited by NLRP3 as disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some embodiments, the disease or disorder is a disease or disorder in which NLRP3 activity is implicated.

In some embodiments, the disease or disorder is inflammation, an auto-immune disease, a cancer, an infection, a disease or disorder of the central nervous system, a metabolic disease, a cardiovascular disease, a respiratory disease, a kidney disease, a liver disease, an ocular disease, a skin disease, a lymphatic disease, a rheumatic disease, a psychological disease, graft versus host disease, allodynia, or an NLRP3-related disease in a subject that has been determined to carry a germline or somatic non-silent mutation in NLRP3.

In some aspects, the present disclosure provides a method of treating or preventing inflammation, an auto-immune disease, a cancer, an infection, a disease or disorder of the central nervous system, a metabolic disease, a cardiovascular disease, a respiratory disease, a kidney disease, a liver disease, an ocular disease, a skin disease, a lymphatic disease, a rheumatic disease, a psychological disease, graft versus host disease, allodynia, or an NLRP3-related disease in a subject that has been determined to carry a germline or somatic non-silent mutation in NLRP3 in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating inflammation, an auto-immune disease, a cancer, an infection, a disease or disorder of the central nervous system, a metabolic disease, a cardiovascular disease, a respiratory disease, a kidney disease, a liver disease, an ocular disease, a skin disease, a lymphatic disease, a rheumatic disease, a psychological disease, graft versus host disease, allodynia, or an NLRP3-related disease in a subject that has been determined to carry a germline or somatic non-silent mutation in NLRP3 in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a compound of the present disclosure or a pharmaceutically acceptable salt thereof for use in inhibiting NLRP3 activity (e.g., in vitro or in vivo).

In some aspects, the present disclosure provides a compound of the present disclosure or a pharmaceutically acceptable salt thereof for use in inhibiting NLRP3 (e.g., in vitro or in vivo).

In some aspects, the present disclosure provides a compound of the present disclosure or a pharmaceutically acceptable salt thereof for use as an antagonist for NLRP3 (e.g., in vitro or in vivo).

In some aspects, the present disclosure provides a compound of the present disclosure or a pharmaceutically acceptable salt thereof for use in treating or preventing a disease or disorder disclosed herein.

In some aspects, the present disclosure provides a compound of the present disclosure or a pharmaceutically acceptable salt thereof for use in treating a disease or disorder disclosed herein.

In some aspects, the present disclosure provides use of a compound of the present disclosure or a pharmaceutically acceptable salt thereof in the manufacture of a medicament for inhibiting NLRP3 activity (e.g., in vitro or in vivo).

In some aspects, the present disclosure provides use of a compound of the present disclosure or a pharmaceutically acceptable salt thereof in the manufacture of a medicament for inhibiting NLRP3 (e.g., in vitro or in vivo). In some aspects, the present disclosure provides use of a compound of the present disclosure or a pharmaceutically acceptable salt thereof in the manufacture of a medicament for treating or preventing a disease or disorder disclosed herein.

In some aspects, the present disclosure provides use of a compound of the present disclosure or a pharmaceutically acceptable salt thereof in the manufacture of a medicament for treating a disease or disorder disclosed herein.

Effectiveness of compounds of the disclosure can be determined by industry-accepted assays/disease models according to standard practices of elucidating the same as described in the art and are found in the current general knowledge.

In some embodiments, the disease or disorder is inflammation, an auto-immune disease, a cancer, an infection, a disease or disorder of the central nervous system, a metabolic disease, a cardiovascular disease, a respiratory disease, a kidney disease, a liver disease, an ocular disease, a skin disease, a lymphatic disease, a rheumatic disease, a psychological disease, graft versus host disease, allodynia, or an NLRP3-related disease in a subject that has been determined to carry a germline or somatic non-silent mutation in NLRP3.

In some embodiments, the disease or disorder of the central nervous system is Parkinson's disease, Alzheimer's disease, traumatic brain injury, spinal cord injury, amyotrophic lateral sclerosis, or multiple sclerosis.

In some embodiments, the kidney disease is an acute kidney disease, a chronic kidney disease, or a rare kidney disease.

In some embodiments, the skin disease is psoriasis, hidradenitis suppurativa (HS), or atopic dermatitis.

In some embodiments, the rheumatic disease is dermatomyositis, Still's disease, or juvenile idiopathic arthritis.

In some embodiments, the NLRP3-related disease in a subject that has been determined to carry a germline or somatic non-silent mutation in NLRP3 is cryopyrin-associated autoinflammatory syndrome.

In some embodiments, the cryopyrin-associated autoinflammatory syndrome is familial cold autoinflammatory syndrome, Muckle-Wells syndrome, or neonatal onset multisystem inflammatory disease.

Routes of Administration

Compounds of the present disclosure, or pharmaceutically acceptable salts thereof, may be administered alone as a sole therapy or can be administered in addition with one or more other substances and/or treatments. Such conjoint treatment may be achieved by way of the simultaneous, sequential or separate administration of the individual components of the treatment.

For example, therapeutic effectiveness may be enhanced by administration of an adjuvant (i.e. by itself the adjuvant may only have minimal therapeutic benefit, but in combination with another therapeutic agent, the overall therapeutic benefit to the individual is enhanced). Alternatively, by way of example only, the benefit experienced by an individual may be increased by administering the compound of Formula (I) with another therapeutic agent (which also includes a therapeutic regimen) that also has therapeutic benefit.

In the instances where the compound of the present disclosure is administered in combination with other therapeutic agents, the compound of the disclosure need not be administered via the same route as other therapeutic agents, and may, because of different physical and chemical characteristics, be administered by a different route. For example, the compound of the disclosure may be administered orally to generate and maintain good blood levels thereof, while the other therapeutic agent may be administered intravenously. The initial administration may be made according to established protocols known in the art, and then, based upon the observed effects, the dosage, modes of administration and times of administration can be modified by the skilled clinician.

The particular choice of other therapeutic agent will depend upon the diagnosis of the attending physicians and their judgment of the condition of the individual and the appropriate treatment protocol. According to this aspect of the disclosure there is provided a combination for use in the treatment of a disease in which inflammasome activity is implicated comprising a compound of the disclosure as defined hereinbefore, or a pharmaceutically acceptable salt thereof, and another suitable agent.

According to a further aspect of the disclosure there is provided a pharmaceutical composition which comprises a compound of the disclosure, or a pharmaceutically acceptable salt thereof, in combination with a suitable, in association with a pharmaceutically acceptable diluent or carrier.

In any of the above-mentioned pharmaceutical composition, process, method, use, medicament, and manufacturing features of the instant disclosure, any of the alternate embodiments of macromolecules of the present disclosure described herein also apply.

The compounds of the disclosure or pharmaceutical compositions comprising these compounds may be administered to a subject by any convenient route of administration, whether systemically/peripherally or topically (i.e., at the site of desired action).

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

EXAMPLES

For exemplary purpose, neutral compounds of Formula (I) are synthesized and tested in the examples. It is understood that the neutral compounds of Formula (I) may be converted to the corresponding pharmaceutically acceptable salts of the compounds using routine techniques in the art (e.g., by saponification of an ester to the carboxylic acid salt, or by hydrolyzing an amide to form a corresponding carboxylic acid and then converting the carboxylic acid to a carboxylic acid salt).

Nuclear magnetic resonance (NMR) spectra were recorded at 400 MHz as stated and at 300.3 K unless otherwise stated; the chemical shifts ($\delta$) are reported in parts per million (ppm). Spectra were recorded using a Bruker Avance 400instrument with 8, 16 or 32 scans.

LC-MS chromatograms and spectra were recorded using a Shimadzu LCMS-2020. Injection volumes were 0.7-8.0 µl and the flow rates were typically 0.8 or 1.2 ml/min. Detection methods were diode array (DAD) or evaporative light scattering (ELSD) as well as positive ion electrospray ionisation. MS range was 100-1000 Da. Solvents were gradients of water and acetonitrile both containing a modifier (typically 0.01-0.04%) such as trifluoroacetic acid or ammonium carbonate.

Abbreviations

DMF N,N-dimethylformamide
DMSO dimethylsulfoxide
dppf 1,1'-bis(diphenylphosphino)ferrocene
ESI electrospray ionisation
EtOAc or EA ethyl acetate
EtOH ethanol
h hour(s)
HPLC high-performance liquid chromatography
LCMS Liquid Chromatography—Mass Spectrometry
MeCN or ACN acetonitrile
min minute(s)
mw microwave
m/z mass/charge
PE petroleum ether
prep-HPLC preparative high-performance liquid chromatography
rt room temperature
Y yield A suitable general route for the preparation of a compound of the application can be described using protocol A in Scheme 2 herein.

Scheme 2

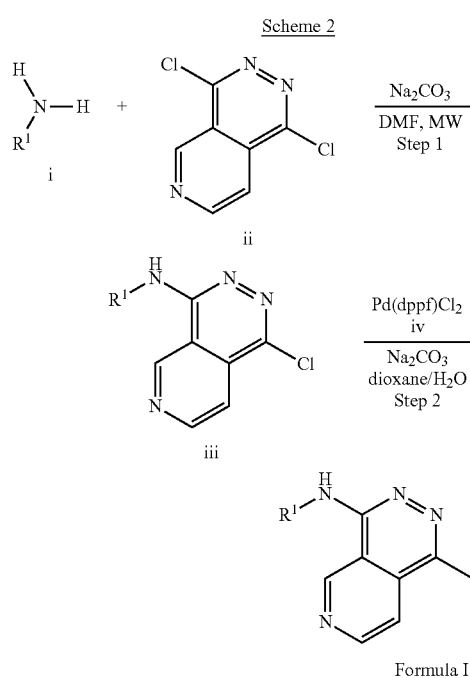

where R' represents substituents of Y

Step 1 involves an S$_N$Ar reaction between an amine (i) and an aryl dichloride (ii), to provide the target chloroaryl intermediate (iii). Step 2 involves cross-coupling between intermediate (iii) and the desired boronic acids or boronates iv to generate the desired compound of Formula I. Amines i, aryl dichlorides ii and boronic acids or boronates iv are either commercially available or known in the chemical literature, unless otherwise indicated.

A suitable general route for the preparation of a compound of the application is also described using protocol B in Scheme 3 herein.

Scheme 3

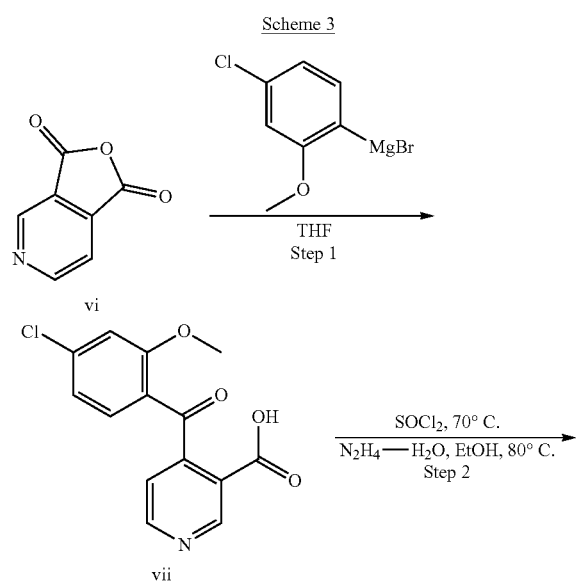

where Y is sub with OH and halo

Step 1 involves opening commercially available 3,4-pyridinedicarboxylic acid anhydride vi with a Grignard reagent to obtain carboxylic acid vii. Step 2 features chlorination, then condensation with hydrazine to furnish pyridazinol viii. Step 3 then involves another chlorination to furnish key intermediate ix, which in turn may be engaged in step 4 as a an SNAr reaction with an amine (i) to form azaphthalazines x. Step 5 then features a methyl ether deprotection then provides the compound of Formula I.

Example 1. Synthesis of (S)-1-(4-chlorophenyl)-N-((tetrahydrofuran-2-yl)methyl)pyrido[3,4-d]pyridazin-4-amine (Compound 1) and (S)-4-(4-chlorophenyl)-N-((tetrahydrofuran-2-yl)methyl)pyrido[3,4-d]pyridazin-1-amine (Compound 2)

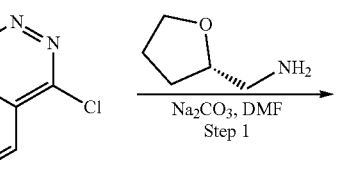

-continued

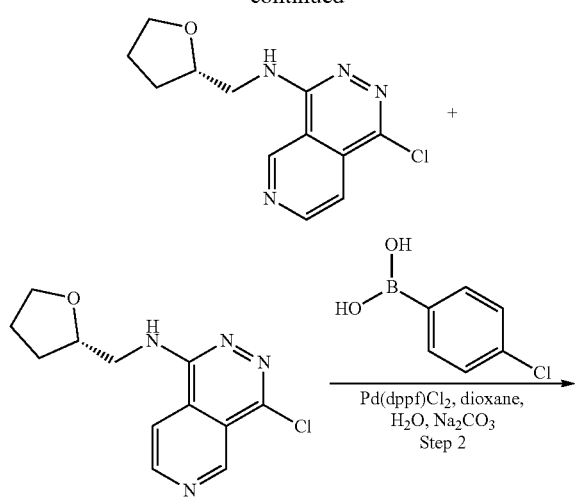

1

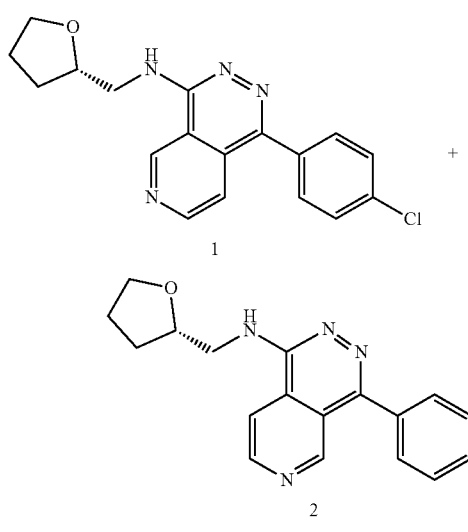

2

Step 1. Synthesis of (S)-1-chloro-N-((tetrahydrofuran-2-yl)methyl)pyrido[3,4-d]pyridazin-4-amine and (S)-4-chloro-N-((tetrahydrofuran-2-yl)methyl)pyrido[4,3-d]pyridazin-1-amine

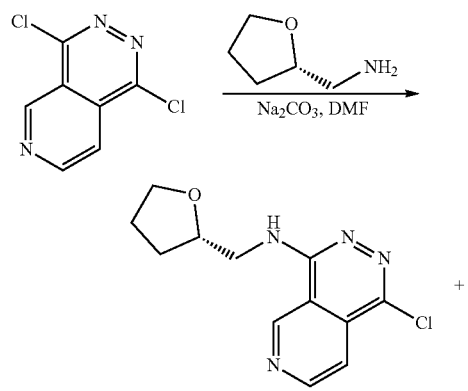

-continued

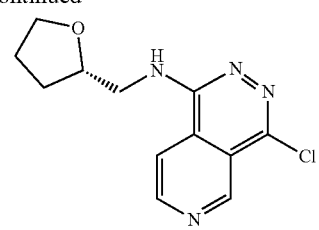

Into a 8 mL microwave tube were added 1,4-dichloro-pyrido[3,4-d]pyridazine (250 mg, 1.25 mmol, 1.00 equiv), 1-[(2S)-oxolan-2-yl]methanamine (152 mg, 1.50 mmol, 1.20 equiv), Na$_2$CO$_3$ (397 mg, 3.75 mmol, 3.00 equiv) and DMF (2 ml). The final reaction mixture was irradiated with microwave radiation for 30 min at 130° C. Reaction progress was monitored by LCMS. The reaction was then quenched by the addition of 20 mL of water. The resulting solution was extracted with 3×15 mL of ethyl acetate. The resulting mixture was concentrated under vacuum. The residue was purified by silica gel column chromatography, eluting with PE/EA (1:9) to afford (S)-1-chloro-N-((tetrahydrofuran-2-yl)methyl)pyrido[3,4-d]pyridazin-4-amine and (S)-4-chloro-N-((tetrahydrofuran-2-yl)methyl)pyrido[4,3-d]pyridazin-1-amine (150 mg, 45%, mixture of two isomers) as a yellow oil. LCMS (ES, m/z): RT=0.54 min, m/z=265.0 [M+1]+.

Step 2. Synthesis of (S)-1-(4-chlorophenyl)-N-((tetrahydrofuran-2-yl)methyl)pyrido[3,4-d]pyridazin-4-amine (Compound 1) and (S)-4-(4-chlorophenyl)-N-((tetrahydrofuran-2-yl)methyl)pyrido[3,4-d]pyridazin-1-amine (Compound 2)

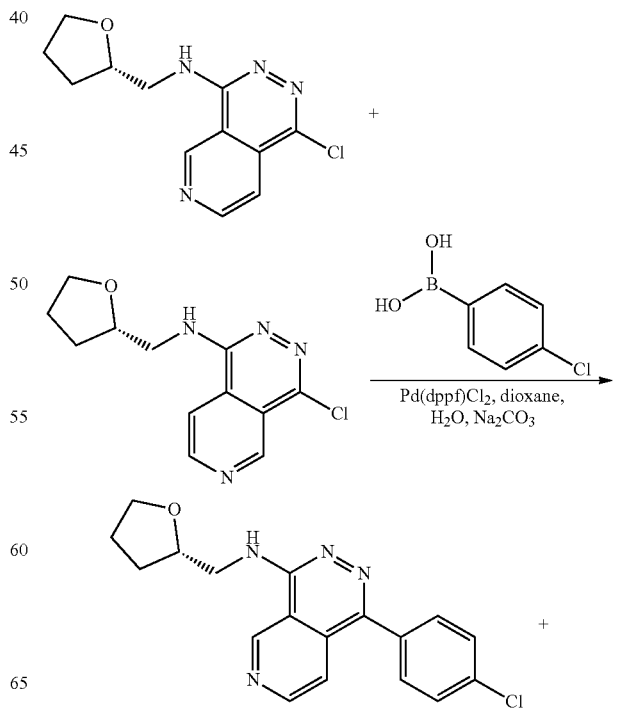

97

-continued

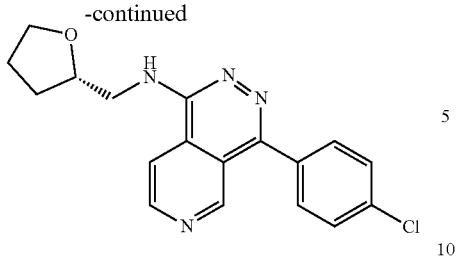

Into a 8 mL microwave tube purged and maintained with an inert atmosphere of nitrogen, was placed a mixture of (S)-1-chloro-N-((tetrahydrofuran-2-yl)methyl)pyrido[3,4-d]pyridazin-4-amine and (S)-4-chloro-N-((tetrahydrofuran-2-yl)methyl)pyrido[4,3-d]pyridazin-1-amine (150 mg, 0.56 mmol, 1.00 equiv), β-chloro-benzeneboronic acid (106 mg, 0.68 mmol, 1.20 equiv), Pd(dppf)Cl$_2$ (82.9 mg, 0.11 mmol, 0.20 equiv), Na$_2$CO$_3$ (180 mg, 1.70 mmol, 3.00 equiv), dioxane (2.0 mL, 23.61 mmol, 41.7 equiv), and H$_2$O (0.4 mL, 22.20 mmol, 39.2 equiv). The resulting solution was stirred for 2 h at 80° C. in an oil bath. Reaction progress was monitored by LCMS. The resulting solution was extracted with 3×5 mL of ethyl acetate and the resulting mixture was concentrated under vacuum. The residue was purified by silica gel column chromatography, eluting with PE/EA (1:5) to afford (S)-1-(4-chlorophenyl)-N-((tetrahydrofuran-2-yl)methyl)pyrido[3,4-d]pyridazin-4-amine and (S)-4-(4-chlorophenyl)-N-((tetrahydrofuran-2-yl)methyl)pyrido[4,3-d]pyridazin-1-amine (160 mg, mixture of two isomers) as a yellow solid. The crude product (160 mg, purity=83.23%) was purified by prep-HPLC with the following conditions (2 #SHIMADZU (HPLC-01)), Column: XBridge Prep OBD C18, 30*150 mm, 5 μm; Mobile Phase A: Water (10 mmol/L NH$_4$HCO$_3$), Mobile Phase B: ACN; Flow rate: 60 mL/min; Gradient: 25% B to 42% B in 8 min; Wave Length: 254/220 nm. This resulted in Compound 1 (53.3 mg, 27%) as an off-white solid and Compound 2 (5.6 mg, 7.3%) as an off-white solid. Compound 1: LCMS (ES, m/z): RT=0.66 min, m/z=341.1 [M+1]+. $^1$H NMR (400 MHz, DMSO-d$_6$) δ 9.80 (d, J=1.0 Hz, 1H), 8.92 (d, J=5.7 Hz, 1H), 8.21 (t, J1=J2=5.7 Hz, 1H), 7.73-7.66 (m, 2H), 7.66-7.59 (m, 3H), 4.28-4.25 (m, 1H), 3.87-3.82 (m, 1H), 3.80-3.63 (m, 3H), 2.02-1.97 (m, 1H), 1.97-1.77 (m, 2H), 1.71-1.66 (m, 1H). Compound 2: LCMS (ES, m/z): RT=0.65 min, m/z=341.2 [M+1]+. $^1$H NMR (400 MHz, DMSO-d$_6$) δ 9.16 (s, 1H), 9.01 (d, J=5.6 Hz, 1H), 8.31 (d, J=5.6 Hz, 1H), 8.00 (t, J1=J1=5.7 Hz, 1H), 7.78-7.71 (m, 2H), 7.67-7.60 (m, 2H), 4.31-4.20 (m, 1H), 3.84-3.81 (m, 1H), 3.77-3.61 (m, 3H), 2.07-1.77 (m, 3H), 1.74-1.61 (m, 1H).

Example 2. Synthesis of (R)-1-(4-chlorophenyl)-4-((tetrahydrofuran-2-yl)methoxy)pyrido[3,4-d]pyridazine (Compound 3) and (R)-4-(4-chlorophenyl)-1-((tetrahydrofuran-2-yl)methoxy)pyrido[3,4-d]pyridazine (Compound 4)

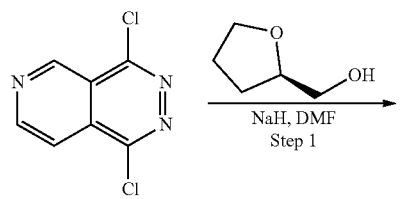

98

-continued

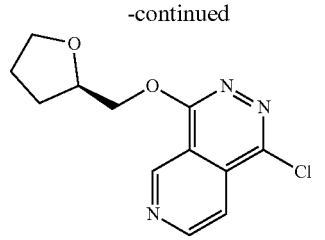

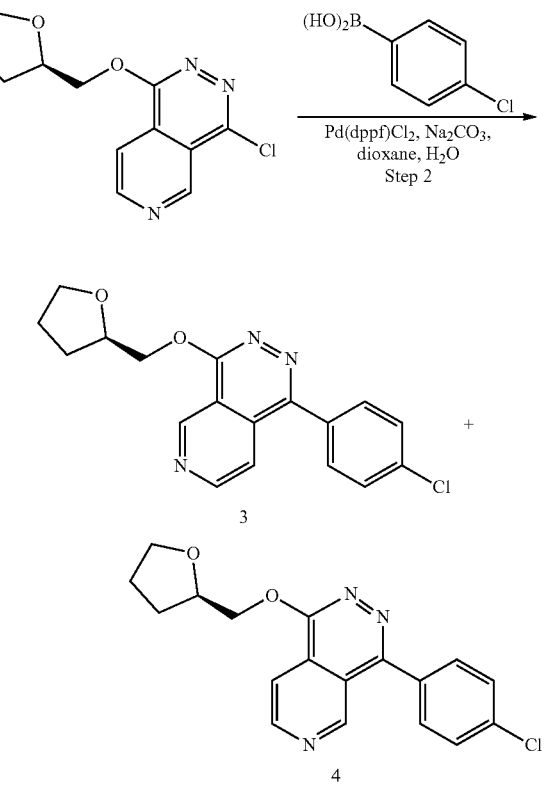

Step 1: Synthesis of (R)-1-chloro-4-((tetrahydrofuran-2-yl)methoxy)pyrido[3,4-d]pyridazine and (R)-4-chloro-1-((tetrahydrofuran-2-yl)methoxy)pyrido[4,3-d]pyridazine

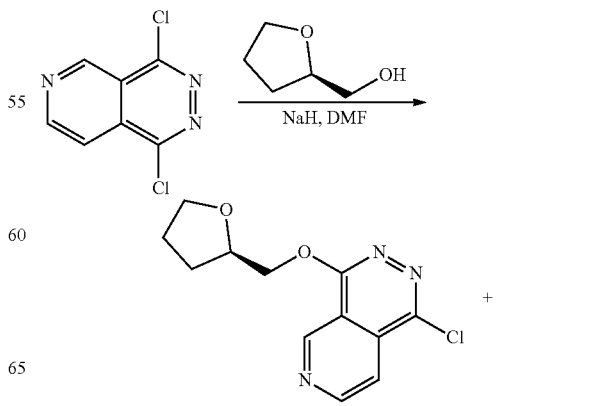

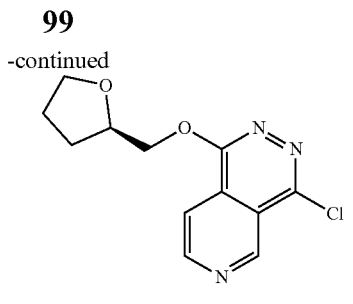

Into a 50 mL 3-necked round-bottom flask, was placed (R)-(tetrahydrofuran-2-yl)methanol (61.3 mg, 0.60 mmol, 0.80 equiv), DMF (1.5 mL, 19.38 mmol, 25.9 equiv), and NaH (36.0 mg, 1.50 mmol, 2.00 equiv, 60% in mineral). The resulting mixture was stirred for 1 h at 0° C. This was followed by the addition of 1,4-dichloropyrido[3,4-d]pyridazine (150 mg, 0.75 mmol, 1.00 equiv) portionwise at 0° C. The resulting solution was stirred for 2 h at 25° C. Reaction progress was monitored by LCMS. The reaction was then quenched by the addition of 5 mL of water. The resulting solution was extracted with 3×5 mL of ethyl acetate. The resulting mixture was concentrated under vacuum. The residue was purified by silica gel column chromatography, eluting with PE/EA (5:1) to afford (R)-1-chloro-4-((tetrahydrofuran-2-yl)methoxy)pyrido[3,4-d]pyridazine and (R)-4-chloro-1-((tetrahydrofuran-2-yl)methoxy)pyrido[4,3-d]pyridazine (160 mg, 80%, mixture of two isomers) as a light yellow oil. LCMS (ES, m/z). RT=0.60 min, m/z=266[M+1]$^+$.

Step 2: Synthesis of (R)-1-(4-chlorophenyl)-4-((tetrahydrofuran-2-yl)methoxy)pyrido[3,4-d]pyridazine (Compound 3) and (R)-4-(4-chlorophenyl)-1-((tetrahydrofuran-2-yl)methoxy)pyrido[3,4-d]pyridazine (Compound 4)

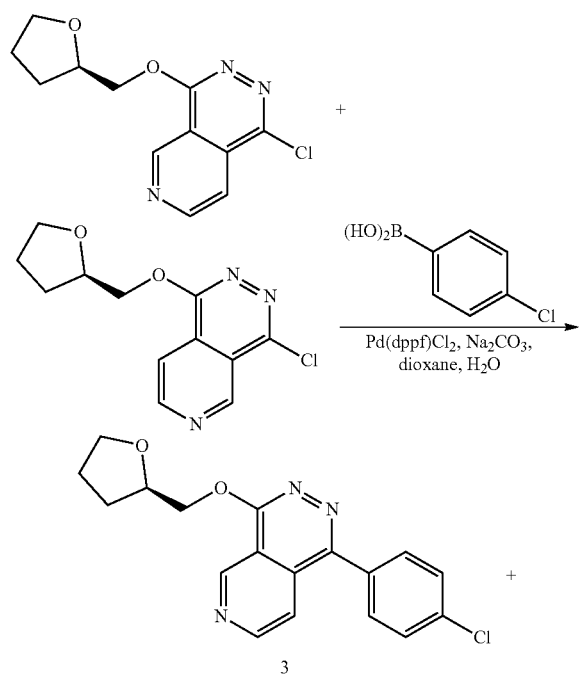

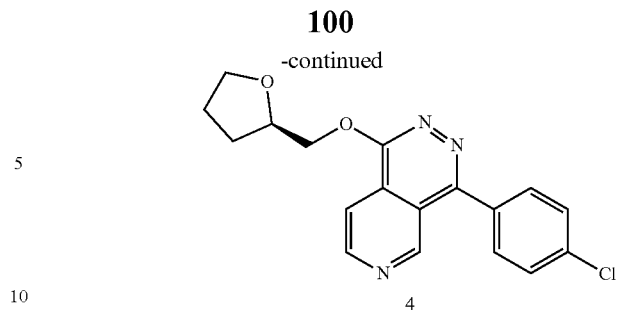

Into a 10 mL sealed tube were added (R)-1-chloro-4-((tetrahydrofuran-2-yl)methoxy)pyrido[3,4-d]pyridazine and (R)-4-chloro-1-((tetrahydrofuran-2-yl)methoxy)pyrido[4,3-d]pyridazine (150 mg, 0.56 mmol, 1.00 equiv), β-chloro-benzeneboronic acid, (106 mg, 0.67 mmol, 1.20 equiv), Pd(dppf)Cl$_2$ (82.6 mg, 0.11 mmol, 0.20 equiv), Na$_2$CO$_3$ (119 mg, 1.13 mmol, 2.00 equiv), dioxane (1.5 mL, 17.7 mmol, 31.4 equiv), and H$_2$O (0.3 mL, 16.7 mmol, 29.5 equiv) at 25° C. The resulting mixture was stirred for 2 h at 80° C. under nitrogen atmosphere. Reaction progress was monitored by LCMS. The resulting solution was extracted with 3×5 mL of ethyl acetate. The resulting mixture was concentrated under vacuum. The residue was purified by silica gel column chromatography, eluting with PE/EA (1:3) to afford (R)-1-(4-chlorophenyl)-4-((tetrahydrofuran-2-yl)methoxy)pyrido[3,4-d]pyridazine and (R)-4-(4-chlorophenyl)-1-((tetrahydrofuran-2-yl)methoxy)pyrido[4,3-d]pyridazine (150 mg, purity=78.30%, mixture of two isomers) as a light yellow oil. The crude product (150 mg, purity=78.30%) was purified by Prep-HPLC with the following conditions (2 #SHIMADZU (HPLC-01)): Column, XBridge Shield RP18 OBD, 30*150 mm, 5 μm; mobile phase, Water (10 mmol/L NH$_4$HCO$_3$) and ACN (hold 35% ACN in 12 min); Detector, UV254/220 nm. This resulted in Compound 3 (3.3 mg, 12%) as a white solid and Compound 4 (75.8 mg, 39%) as a white solid. Compound 3: LCMS (ES, m/z): RT=1.57 min, m/z=342[M+1]$^+$. $^1$H NMR (400 MHz, DMSO-d$_6$) δ 9.63 (d, J=1.0 Hz, 1H), 9.08 (d, J=5.7 Hz, 1H), 7.83-7.73 (m, 3H), 7.73-7.66 (m, 2H), 4.69-4.59 (m, 2H), 4.42-4.39 (m, 1H), 4.01-3.86 (m, 1H), 3.80-3.71 (m, 1H), 2.19-2.06 (m, 1H), 2.06-1.79 (m, 3H). Compound 4: LCMS (ES, m/z): RT=1.04 min, m/z=342[M+1]$^+$. $^1$H NMR (400 MHz, DMSO-d$_6$) δ 9.63-9.30 (m, 1H), 9.13-9.07 (m, 1H), 8.12-7.77 (m, 3H), 7.76-7.74 (m, 1H), 7.72-7.66 (m, 1H), 4.76-4.58 (m, 2H), 4.42-4.37 (m, 1H), 3.88-3.81 (m, 1H), 3.79-3.71 (m, 1H), 2.12-2.08 (m, 1H), 2.00-1.95 (m, 1H), 1.94-1.82 (m, 2H).

Example 3. 5-chloro-2-(4-((2-hydroxy-2-methylpropyl)amino)pyrido[3,4-d]pyridazin-1-yl)phenol (Compound 82)

Step 1: Synthesis of 1-({1-chloropyrido[3,4-d]pyridazin-4-yl}amino)-2-methylpropan-2-ol

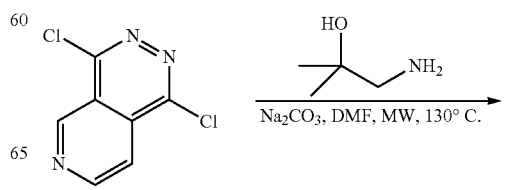

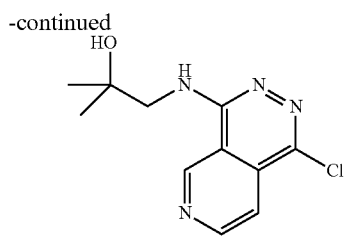

Into a 20 mL sealed tube were added 1,4-dichloropyrido[3,4-d]pyridazine (1.00 g, 5.00 mmol, 1.00 equiv), 1-amino-2-methylpropan-2-ol (0.42 g, 4.75 mmol, 0.95 equiv) DMF (10.00 mL) and Na$_2$CO$_3$ (1.59 g, 15.00 mmol, 3.00 equiv) at room temperature. The final reaction mixture was microwave irradiated for 30 min at 130° C. The reaction was performed two hundred times in parallel. All of reaction solutions were then collected and filtered to remove inorganic salts. Then the filtrate was concentrated to 160-200 mL under reduced pressure. The residue was diluted in DCM (200 mL) and shaken in an ultrasonic bath for 10 min (dark brown solids were precipitated in the solution), then petroleum ether (200 mL) was added. After stirring for 20 min, the resulting mixture was diluted with another portion of petroleum ether (80 mL). The precipitated solids were collected by filtration and the filter cake was then washed with water (2×60 mL). The solids were collected and dried under vacuum. (If the undesired regio-isomer is still detected by LC-MS and H-NMR, the solids will be dissolved again in DMF and the above work up procedures were repeated). This resulted in 1-({1-chloropyrido[3,4-d]pyridazin-4-yl}amino)-2-methylpropan-2-ol (103.0 g, yield: 40%) as a yellow solid. LCMS (LCMS, ESI): RT=0.83 min, m/z=253.0 [M+H]$^+$. $^1$H NMR (400 MHz, DMSO-d$_6$) δ 9.83 (d, J=1.0 Hz, 1H), 9.06 (d, J=5.6 Hz, 1H), 7.96 (t, J=6.0 Hz, 1H), 7.93-7.77 (m, 1H), 4.82 (s, 1H), 3.64 (d, J=5.9 Hz, 2H), 1.19 (s, 6H).

Step 2: Synthesis of 5-chloro-2-(4-((2-hydroxy-2-methylpropyl)amino)pyrido[3,4-d]pyridazin-1-yl)phenol (Compound 82)

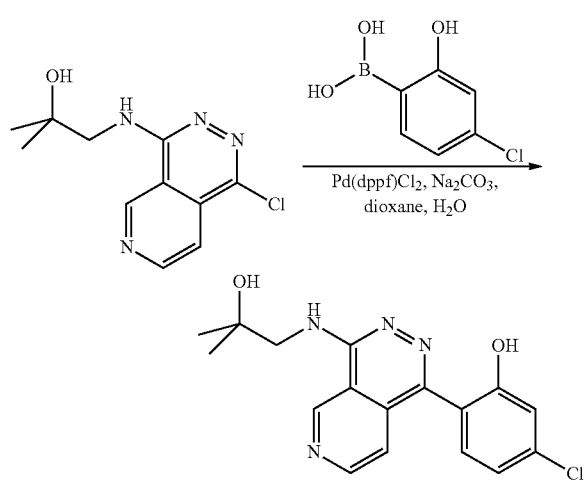

To a stirred solution of 1-($1-chloropyrido[3,4-d]pyridazin-4-yl)amino)-2-methylpropan-2-ol (500 mg, 1.98 mmol, 1.00 equiv) and 4-chloro-2-hydroxyphenylboronic acid (375 mg, 2.176 mmol, 1.10 equiv) in dioxane and H$_2$O (5:1.8 mL) were added Pd(dppf)Cl$_2$ (275 mg, 0.376 mmol, 0.19 equiv) and Na$_2$CO$_3$ (426 mg, 4.019 mmol, 2.03 equiv) in portions at room temperature. The resulting mixture was stirred for 1 h at 80 degrees C. under nitrogen atmosphere. The residue was purified by reverse flash chromatography with the following conditions; column, C18 silica gel; mobile phase, MeOH in water, 30% gradient in 10 min; detector, UV 254 nm to afford the crude product. Then the crude product was purified by Prep-HPLC with the following conditions (Column: XSelect CSH Prep C18 OBD Column, 19*250 mm, 5 μm; Mobile Phase A: Water (10 mmol/L NH$_4$HCO$_3$), Mobile Phase B: DCM:EtOH=9:1-HPLC; Flow rate: 25 mL/min; Gradient: 55% B to 55% B in 13 min, 55% B; Wave Length: 254 nm; RT1(min): 11.5; to afford 5-chloro-2-{4-[(2-hydroxy-2-methylpropyl)amino]pyrido[3,4-d]pyridazin-1-yl}phenol (118.7 mg, 17.38%) as a yellow solid. LCMS (ES, m/z): m/z=345.10 [M+H]$^+$. $^1$H NMR (400 MHz, DMSO-d$_6$) δ 10.25 (s, 1H), 9.80 (d, J=1.0 Hz, 1H), 8.87 (d, J=5.6 Hz, 1H), 7.84 (t, J=5.9 Hz, 1H), 7.39-7.25 (m, 2H), 7.03 (d, J=7.7 Hz, 2H), 5.07 (s, 1H), 3.70 (d, J=5.8 Hz, 2H), 1.23 (s, 6H).

Example 4. Synthesis of 5-chloro-2-(4-((2-methoxy-2-methylpropyl)amino)pyrido[3,4-d]pyridazin-1-yl)phenol (Compound 83)

Step 1: Synthesis of 1-chloro-N-(2-methoxy-2-methylpropyl)pyrido[3,4-d]pyridazin-4-amine and 4-chloro-N-(2-methoxy-2-methylpropyl)pyrido[4,3-d]pyridazin-1-amine

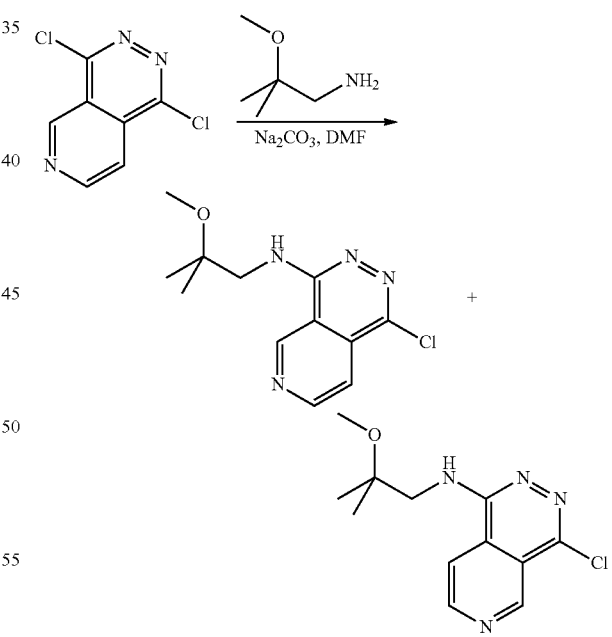

Into a 8 mL microwave sealed tube were added 1,4-dichloropyrido[3,4-d] pyridazine (200 mg, 1.00 mmol, 1.00 equiv), 2-methoxy-2-methylpropan-1-amine (103 mg, 1.00 mmol, 1.00 equiv), Na2CO3 (318 mg, 3.00 mmol, 3.00 equiv) and DMF (3.00 mL). The final reaction mixture was irradiated with microwave radiation for 0.5 h at 130° C. Desired product could be detected by LCMS. The resulting mixture was concentrated under reduced pressure. The residue was purified by silica gel column chromatography, eluted with PE/EA (1:1) to afford 1-chloro-N-(2-methoxy-2-methylpropyl)pyrido[3,4-d]pyridazin-4-amine and 4-chloro-N-(2-methoxy-2-methylpropyl)pyrido[4,3-d]pyridazin-1-amine (180.0 mg, yield=67.5%, mixture of two isomers) as a yellow solid. LCMS (ES, m/z): RT=0.61 min, m/z=267[M+1]$^+$.

Step 2: Synthesis of 5-chloro-2-{4-[(2-methoxy-2-methylpropyl)amino]pyrido[3,4-d]pyridazin-1-yl}phenol (compound 83)

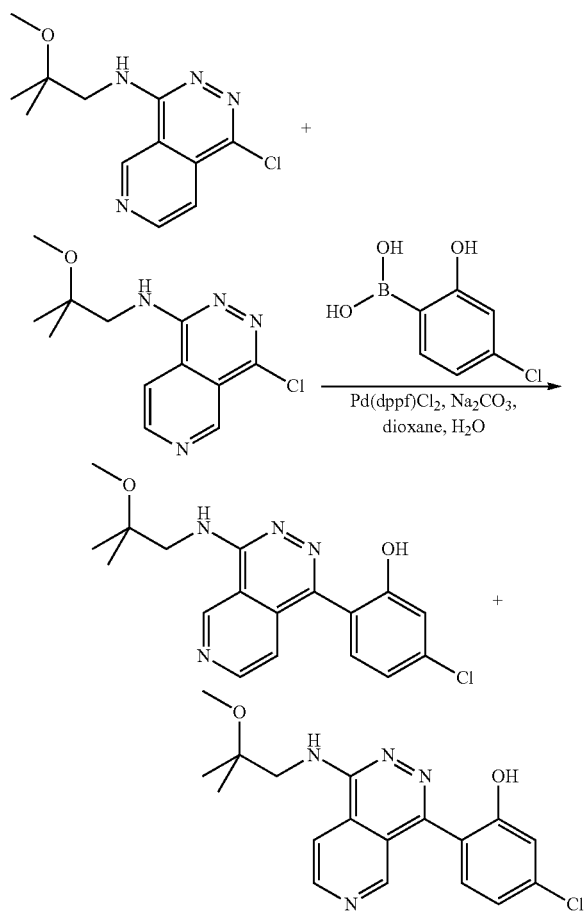

Into a 8 mL sealed tube were added 1-chloro-N-(2-methoxy-2-methylpropyl)pyrido[3,4-d]pyridazin-4-amine (140 mg, 0.52 mmol, 1.00 equiv), 4-chloro-2-hydroxyphenylboronic acid (181 mg, 1.05 mmol, 2.00 equiv), Pd(dppf)Cl2 (76.8 mg, 0.10 mmol, 0.20 equiv), Na2CO3 (167 mg, 1.57 mmol, 3.00 equiv), Dioxane (2.00 mL) and H2O (0.30 mL). The resulting mixture was stirred for 2 h at 80° C. under nitrogen atmosphere. Desired product could be detected by LCMS. The resulting mixture was extracted with EA (3×5 mL). The combined organic layers were washed with water (3×5 mL), dried over anhydrous MgSO4. After filtration, the filtrate was concentrated under reduced pressure. The resulting mixture was concentrated under vacuum. The residue was purified by silica gel column chromatography, eluted with PE/EA (1:1) to afford 5-chloro-2-{4-[(2-methoxy-2-methylpropyl)amino]pyrido[3,4-d]pyridazin-1-yl}phenol and 5-chloro-2-{4-[(2-methoxy-2-methylpropyl)amino]pyrido[3,4-d]pyridazin-1-yl}phenol (68.0 mg, purity=85.00%, mixture of two isomers) as a yellow oil. The crude product (68.0 mg, purity=85.00%, mixture of two isomers) was purified by Prep-HPLC with the following conditions (2 #SHIMADZU (HPLC-01)): Column, XBridge Shield RP18 OBD Column, 30*150 mm, 5 μm; mobile phase, Water (10 mmol/L NH4HCO3) and ACN (35% ACN up to 45% in 8 min); Detector, UV254 nm. This resulted in 5-chloro-2-{4-[(2-methoxy-2-methylpropyl)amino]pyrido[3,4-d]pyridazin-1-yl}phenol (28.1 mg, yield=14.9/6) as a yellow solid and 5-chloro-2-{4-[(2-methoxy-2-methylpropyl)amino]pyrido[3,4-d]pyridazin-1-yl}phenol (4.00 mg, yield=2.12%) as a yellow green solid.

5-chloro-2-{4-[(2-methoxy-2-methylpropyl)amino]pyrido[3,4-d]pyridazin-1-yl}phenol (compound 83)

LCMS (ES, m/z). RT=0.65 min, m/z=359[M+1]$^+$. $^1$H NMR (400 MHz, DMSO-d$_6$) δ 10.23 (s, 1H), 9.82 (s, 1H), 8.85 (d, J=2.4 Hz, 1H), 7.68-7.65 (m, 1H), 7.36-7.29 (m, 2H), 7.04-7.02 (m, 2H), 3.80 (d, J=6 Hz, 2H), 3.23 (s, 3H), 1.24 (s, 6H).

5-chloro-2-{4-[(2-methoxy-2-methylpropyl)amino]pyrido[3,4-d]pyridazin-1-yl}phenol LCMS (ES, m/z): RT=1.23 min, m/z=359[M+1]$^+$. $^1$H NMR (400 MHz, DMSO-d$_6$) δ 10.28 (s, 1H), 8.93 (d, J=5.6 Hz, 1H), 8.85 (s, 1H), 8.36 (s, 1H), 7.40 (d, J=8.8 Hz, 2H), 7.06-7.04 (m, 2H), 3.77 (d, J=6 Hz, 2H), 3.22 (s, 3H), 1.23 (s, 6H).

Example 5. 5-chloro-2-[4-({[(1S)-3,3-difluorocyclopentyl]methyl}amino)pyrido[3,4-d]pyridazin-1-yl]phenol (Compound 91)

Step 1: 1-chloro-N-[(3,3-difluorocyclopentyl)methyl]pyrido[3,4-d]pyridazin-4-amine

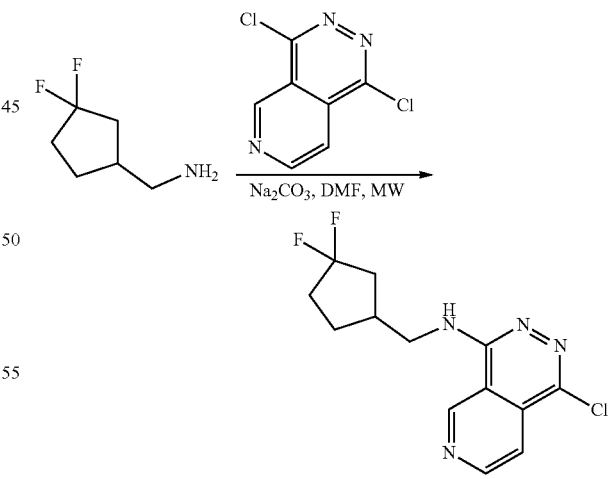

Into a 20 mL pressure tank reactor were added 1-(3,3-difluorocyclopentyl)methanamine (300 mg, 2.22 mmol, 1.00 equiv), 1,4-dichloropyrido[3,4-d]pyridazine (444 mg, 2.22 mmol, 1.00 equiv), Na$_2$CO$_3$ (707 mg, 6.66 mmol, 3.00 equiv), DMF (6.00 mL). The resulting mixture was irradiated with microwave radiation for 30 min at 130° C. The reaction progress was monitored by LCMS. The resulting mixture was filtered, the filter cake was washed with EtOAc (3×5 mL). The filtrate was concentrated under reduced pressure. The crude product was purified by Prep-HPLC with the following conditions: Column: XBridge Prep Phenyl OBD Column, 19*250 mm, 5 μm; Mobile Phase A: Water (10 mmol/L NH$_4$HCO$_3$), Mobile Phase B: ACN; Flow rate: 25 mL/min; Gradient: 40% B to 55% B in 10 min, 55% B; Wave Length: 254 nm; RT1(min): 9. This result in 1-chloro-N-[(3,3-difluorocyclopentyl)methyl]pyrido[3,4-d]pyridazin-4-amine (150 mg, yield=22.62%) as a yellow solid. LCMS: (ES, m/z): RT=0.791 min, m/z=299.0[M+1]$^+$. $^1$H NMR (400 MHz, DMSO-d$_6$) δ 9.75 (s, 1H), 9.06 (d, J=5.6 Hz, 1H), 8.23 (t, J=5.5 Hz, 1H), 7.87 (d, J=5.6 Hz, 1H), 3.61-3.57 (m, 5.6 Hz, 2H), 2.71-2.63 (m, 1H), 2.46-1.75 (m, 5H), 1.65-1.55 (m, 1H).

Step 2: S-chloro-2-[4-({[(1S)-3,3-difluorocyclopentyl]methyl}amino)pyrido[3,4-d]pyridazin-1-yl]phenol (Compound 91)

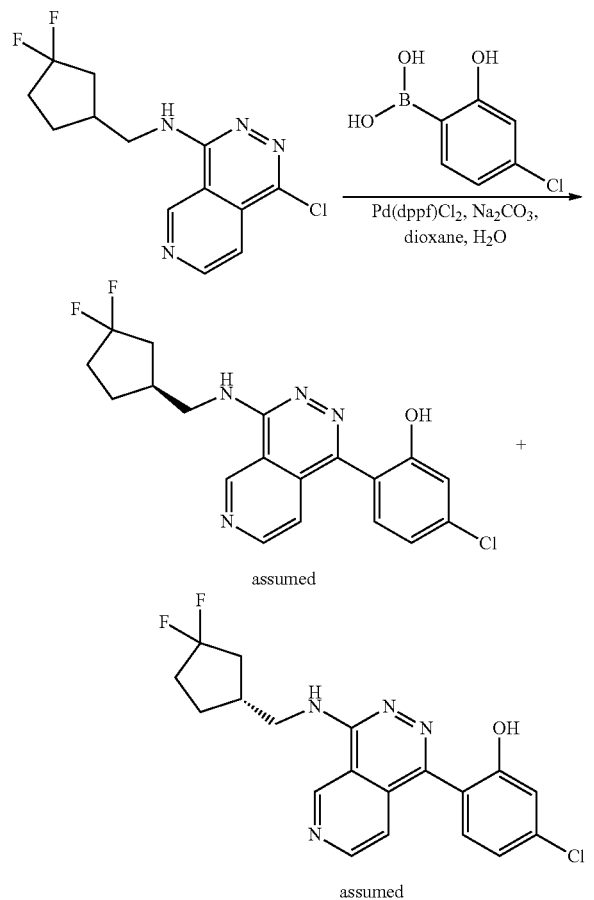

Into a 8 mL vial were added 1-chloro-N-[(3,3-difluorocyclopentyl)methyl]pyrido[3,4-d]pyridazin-4-amine (100 mg, 0.33 mmol, 1.00 equiv), 4-chloro-2-hydroxyphenylboronic acid (69.2 mg, 0.40 mmol, 1.20 equiv), Pd(dppf)Cl$_2$ (73.5 mg, 0.10 mmol, 0.30 equiv), dioxane (0.50 mL), Na$_2$CO$_3$ (106.44 mg, 1.00 mmol, 3.00 equiv), H$_2$O (0.10 mL). The resulting mixture was stirred for 2 h at 80° C. under nitrogen atmosphere. The resulting mixture was concentrated under reduced pressure. The residue was purified by silica gel column chromatography, eluted with PE/EA (1:1) to afford 1-chloro-N-((3,3-difluorocyclopentyl)methyl)pyrido[3,4-d]pyridazin-4-amine (105 mg, purity=92%, mixture of two isomers). The mixture product (105 mg) was purified by Chiral-Prep-HPLC with the following conditions: Column: CHIRALPAK IF, 2*25 cm, 5 μm; Mobile Phase A: Hex(0.2% FA)-HPLC, Mobile Phase B: MeOH:EtOH=1:1-HPLC; Flow rate: 20 mL/min; Gradient: 15% B to 15% B in 21 min; Wave Length: 220/254 nm; RT1(min): 13.98: RT2(min): 17.41; Sample Solvent: MeOH:DCM=1:1; Injection Volume: 0.5 mL; Number Of Runs: 4. This resulted in 5-chloro-2-[4-({[(0S)-3,3-difluorocyclopentyl]methyl}amino)pyrido[3,4-d]pyridazin-1-yl]phenol (26.10 mg, yield=19.17%) as a yellow solid and 5-chloro-2-[4-({[(1R)-3,3-difluorocyclopentyl]methyl}amino)pyrido[3,4-d]pyridazin-1-yl]phenol (14.00 mg, yield=10.69%) as a yellow solid.
First Eluting Peak (Compound 91):
LCMS: (ES, m/z): RT=1.09 min, m/z=391.1[M+1]$^+$.
$^1$H NMR (400 MHz, DMSO-d$_6$) δ 10.23 (s, 1H), 9.74 (s, 1H), 8.86 (d, J=5.6 Hz, 1H), 8.11 (s, 1H), 7.38-7.28 (m, 2H), 7.08-7.00 (m, 2H), 3.67-3.31 (m, 2H), 2.75-2.67 (m, 1H), 2.35-2.31 (m, 1H), 2.24-1.95 (m, 4H), 1.66-1.61 (m, 1H).
Second Eluting Peak:
LCMS: (ES, m/z): RT=1.09 min, m/z=391.1[M+1]$^+$.
$^1$H NMR (400 MHz, DMSO-d$_6$) δ 10.25 (s, 1H), 9.73 (s, 1H), 8.86 (d, J=5.6 Hz, 1H), 8.09-8.06 (m, 1H), 7.38-7.28 (m, 2H), 7.03 (d, J=7.3 Hz, 2H), 3.73-3.58 (m, 2H), 2.77-2.69 (m, 1H), 2.46-2.29 (m, 1H), 2.29-1.81 (m, 4H), 1.66-1.61 (m, 1H).
Similarly, the stereochemistry for compounds 94, 97, 100 and 105 was arbitrarily assigned.

Example 6. 5-chloro-2-(4-{[(1S,2S)-2-hydroxycyclopentyl]amino}pyrido[3,4-d]pyridazin-1-yl)phenol) (compound 95)

Step 1: Synthesis of (1S,2S)-2-((1-(4-chloro-2-methoxyphenyl)pyrido[3,4-d]pyridazin-4-yl)amino)cyclopentan-1-ol

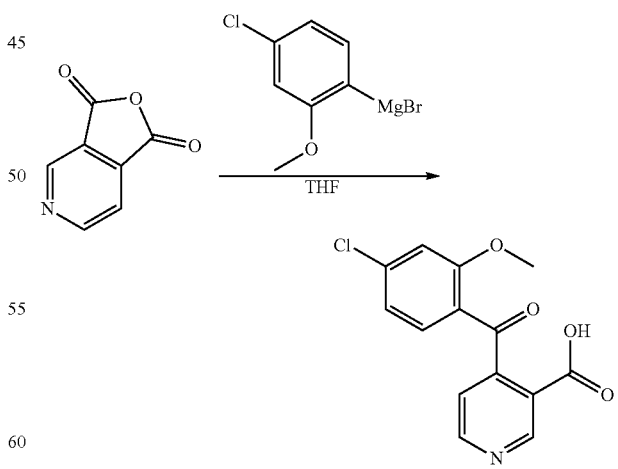

To a stirred solution of furo[3,4-c]pyridine-1,3-dione (30.0 g, 201.20 mmol, 1.00 equiv) and tetrahydrofuran (300 mL) was added bromo(4-chloro-2-methoxyphenyl)magnesium (0.5M in THF) (241 mL, 120 mmol, 0.60 equiv) dropwise at −78° C. under nitrogen atmosphere. The resulting mixture was stirred for 2 h at 25° C. under nitrogen atmosphere. The reaction progress was monitored by LCMS. The reaction was quenched by the addition of water (150 mL) at 0° C. The precipitated solids were collected by filtration and washed with water (3×50 mL). This resulted in 4-(4-chloro-2-methoxybenzoyl)pyridine-3-carboxylic acid (20 g, yield=34.08%) as a light brown solid. LCMS (ES, m/z): RT=0.662 min, m/z=292.0[M+1]+.

Step 2: Synthesis of 1-(4-chloro-2-methoxyphenyl) pyrido[3,4-d]pyridazin-4-ol

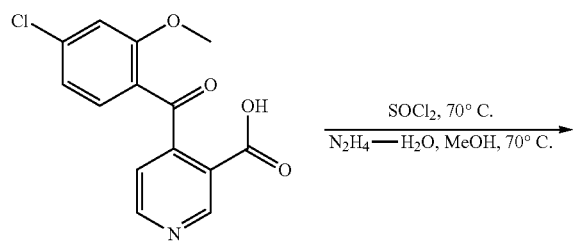

Into a 250 mL round-bottom flask were added 4-(4-chloro-2-methoxybenzoyl)pyridine-3-carboxylic acid (5.00 g, 17.1 mmol, 1.00 equiv) and SOCl₂ (50 mL). The resulting mixture was stirred for 2h at 70° C. The reaction was monitored by TLC. After the reaction was completed, the resulting mixture was concentrated under vacuum. The residue was dissolved in DCM (50 mL) and added into the solution of NH₂NH₂·H₂O (3.43 g, 68.6 mmol, 4.00 equiv), MeOH (50 mL) at 0° C. The resulting mixture was stirred for 3h at 70° C. in an oil bath. The reaction progress was monitored by LCMS. The precipitated solids were collected by filtration. The crude product (4 g, purity=90%) was purified by Prep-HPLC with the following conditions (2 #SHIMADZU (HPLC-01)): Column, XBridge Shield RP18 OBD Column, 19*250 mm, 10 μm; mobile phase, water (10 mmol/L NH4HCO3) and ACN (hold 39% ACN in 17 min); Detector, UV 254/220 nm. This resulted in 1-(4-chloro-2-methoxyphenyl)pyrido[3,4-d]pyridazin-4-ol (2.0 g, yield=40.6%) as a off-white solid. LCMS: (ES, m/z): RT=0.723 min, m/z=288.0 [M+H]+. ¹H NMR (400 MHz, DMSO-d₆) δ 12.90 (s, 1H), 9.50 (s, 1H), 8.94 (d, J=5.5 Hz, 1H), 7.41 (d, J=8.0 Hz, 1H), 7.33 (d, J=1.9 Hz, 1H), 7.23-7.15 (m, 2H), 3.75 (s, 3H).

Step 3: Synthesis of 4-chloro-1-(4-chloro-2-methoxyphenyl)pyrido[3,4-d]pyridazine

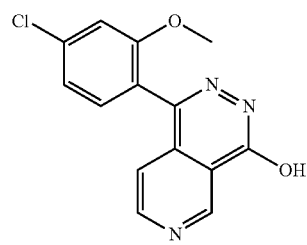

Into a 250 mL round-bottom flask were added 1-(4-chloro-2-methoxyphenyl)pyrido[3,4-d]pyridazin-4-ol (2.5 g, 8.69 mmol, 1.00 equiv) and POCl₃ (40 mL), Pyridine (4 mL). The resulting mixture was stirred for 3h at 100° C. The reaction progress was monitored by LCMS. The reaction was quenched with 500 ml of sodium bicarbonate (aq.) and 500 ml of EtOAc at 0° C. The resulting mixture was extracted with EtOAc (3×500 mL). The combined organic layers were dried over anhydrous Na₂SO₄. After filtration, the filtrate was concentrated under reduced pressure. This resulted in 4-chloro-1-(4-chloro-2-methoxyphenyl)pyrido [3,4-d]pyridazine (1.5 g, yield=56.38%) as a brown solid. LCMS (ES, m/z): RT=0.845 min, m/z=306.0[M+1]+. ¹H NMR (400 MHz, DMSO-d₆) δ 9.84-9.68 (m, 1H), 9.12 (d, J=5.7 Hz, 1H), 7.60-7.56 (m, 1H), 7.51 (d, J=8.1 Hz, 1H), 7.41 (d, J=1.9 Hz, 1H), 7.32-7.25 (m, 1H), 3.74 (s, 3H).

Step 4: Synthesis of (1S,2S)-2-((1-(4-chloro-2-methoxyphenyl)pyrido[3,4-d]pyridazin-4-yl)amino) cyclopentan-1-ol Into a 8 mL microwave tube were added 4-chloro-1-(4-chloro-2-methoxyphenyl)pyrido[3,4-d]pyridazine (90 mg, 0.29 mmol, 1.00 equiv), (1S,2S)-2-aminocyclopentan-1-ol (44.6 mg, 0.44 mmol, 1.50 equiv), Na₂CO₃ (93.5 mg, 0.88 mmol, 3.00 equiv) and 2 mL of NMP at room temperature, the final reaction mixture was stirred for 2h at 60° C. the reaction progress was monitored by LCMS. the reaction mixture was used for next step without further purification. LCMS (ES, m/z): RT=0.629 min, m/z=371 [M+1]$^+$.

Step 5: Synthesis of 5-chloro-2-(4-{[(1S,2S)-2-hydroxycyclopentyl]amino}pyrido[3,4-d]pyridazin-1-yl)phenol) (Compound 95)

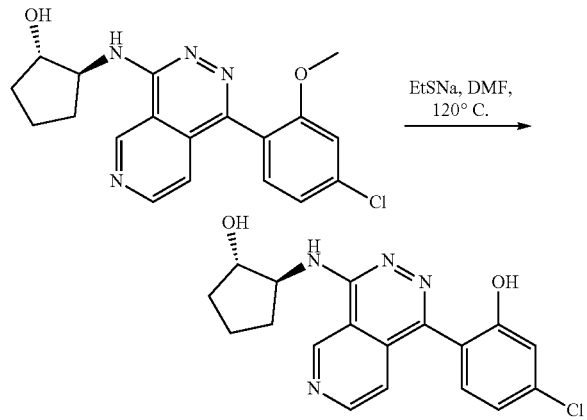

The reaction mixture from VTT-2772-1 was added (ethylsulfanyl)sodium (371.80 mg, 4.43 mmol, 15.00 equiv) at room temperature. The final reaction mixture was stirred for 2h at 120° C. the reaction progress was monitored by LCMS. The reaction was quenched with 20 ml of water, extracted with DCM (3×20 ml), after concentrated, The residue was purified by Prep-HPLC, the condition was: Column: XBridge Shield RP18 OBD Column, 30*150 mm, 5 μm; Mobile Phase A: Water (10 mmol/L NH4HCO3), Mobile Phase B: ACN; Flow rate: 60 mL/min; Gradient: 26% B to 46% B in 8 min, 46% B; Wave Length: 254 nm; RT1(min): 6.5; to afford 5-chloro-2-(4-{[(1S,2S)-2-hydroxycyclopentyl]amino}pyrido[3,4-d]pyridazin-1-yl)phenol)(44.2 mg, yield=42%) as an off-white solid. LCMS (ES, m/z): RT=0.598 min, m/z=357[M+1]$^+$. $^1$H NMR (400 MHz, Methanol-d$_4$) δ 9.73 (d, J=1.0 Hz. 1H), 8.87 (d, J=5.7 Hz, 1H), 7.52 (d, J=5.7 Hz, 1H), 7.38 (d, J=8.0 Hz, 1H), 7.05 (d, J=8.0 Hz, 2H), 4.42-4.34 (m, 1H), 4.27-4.21 (m, 1H), 2.45-2.35 (m, 1H), 2.16-2.06 (m, 1H). 1.97-1.80 (m, 3H), 1.80-1.70 (m, 1H).

Example 7. 5-chloro-2-(4-{[2-(d3)methoxy-2-methylpropyl]amino}pyrido[3,4-d]pyridazin-1-yl)phenol (Compound 99)

Step 1: Synthesis of 1-{bis[(4-methoxyphenyl)methyl]amino}-2-methylpropan-2-ol

Into a 40 mL vial were added 1-amino-2-methylpropan-2-ol (2.00 g, 22.43 mmol, 1.00 equiv), PMBCl (17.57 g, 112.18 mmol, 5.00 equiv), TEA (11.35 g, 112.18 mmol, 5.00 equiv) and DMF (20 mL) at room temperature. The resulting mixture was stirred for 2h at room temperature. The reaction progress was monitored by LCMS. After quenched with water 30 ml, and extracted with DCM (30 ml×3), the organic layer was concentration under vacuum, the residue was purified by reverse flash chromatography with the following conditions: column, C18; mobile phase, MeCN in water, 0% to 100% gradient in 30 min; detector, UV 254 nm. This resulted in 1-{bis[(4-methoxyphenyl)methyl]amino}-2-methylpropan-2-ol (2.9 g, yield=39.23%) as a brown oil. LCMS (ES, m/z): RT=0.758 min, m/z=330.0[M+1]$^+$. 1H NMR (400 MHz, Methanol-d4) δ 7.38-7.17 (m, 4H), 6.88 (d, J=8.2 Hz, 4H), 4.07 (q, J=7.1 Hz, 1H), 3.73 (d, J=5.9 Hz, 9H), 2.57 (s, 2H), 1.09 (s, 6H).

Step 2: Synthesis of [2-(d3)methoxy-2-methylpropyl]bis[(4-methoxyphenyl)methyl]amine)

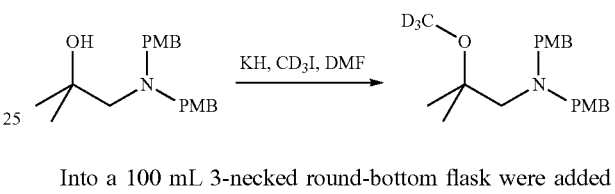

Into a 100 mL 3-necked round-bottom flask were added 1-(bis[(4-methoxyphenyl)methyl]amino)-2-methylpropan-2-ol (500 mg, 1.51 mmol, 1.00 equiv), THF (15 mL), KH (30%) (1.00 g, 7.55 mmol, 5.00 equiv) was added at 0° C. The resulting mixture was stirred for 30 min at 0° C. Then added CD$_3$I (660 mg, 4.55 mmol, 3.00 equiv) in THF (15 mL) at 0° C. The resulting mixture was stirred for 1 h at room temperature. The reaction progress was monitored by LCMS. The reaction was quenched with 50 mL of NH4Cl (aq), the resulting mixture was extracted with EtOEt (3×50 mL). The combined organic layers were washed with NaCl (aq) (2×50 mL), dried over anhydrous Na$_2$SO$_4$. After filtration, the filtrate was concentrated under reduced pressure. The residue was purified by reverse flash chromatography with the following conditions: column, C18; mobile phase, MeCN in water, 0% to 100% gradient in 30 min; detector, UV 254 nm. This resulted in [2-(d3)methoxy-2-methylpropyl]bis[(4-methoxyphenyl)methyl]amine) (400 mg, yield=76.04%) as a yellow oil. LCMS (ES, m/z): RT=0.812 min, m/z=357.0 [M+H]$^+$. $^1$H NMR (400 MHz, Methanol-d4) δ 7.31-7.18 (m, 4H), 6.95-6.79 (m, 4H), 3.79 (s, 6H), 3.56 (s, 4H), 2.45 (s, 2H), 1.06 (s, 6H).

Step 3: Synthesis of 2-(d3)methoxy-2-methylpropan-1-amine

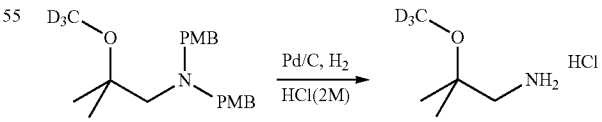

Into a 250 mL round-bottom flask were added [2-(d3)methoxy-2-methylpropyl]bis[(4-methoxyphenyl)methyl]amine (1.00 g, 2.88 mmol, 1.00 equiv), Pd/C (154 mg, 1.44 mmol, 0.50 equiv) and MeOH (100 mL) at room temperature. The resulting mixture was stirred for overnight at room temperature under hydrogen atmosphere. The reaction progress was monitored by LCMS. 5 mL of HCl(2M) was added in this solution, then the reaction mixture was stirred for 30 min at room temperature. The resulting mixture was filtered, the filter cake was washed with MeOH (3×10 mL). The filtrate was concentrated under reduced pressure. This resulted in 2-(d3)methoxy-2-methylpropan-1-amine (200 mg, yield=48.90%) as a red solid. LCMS: (ES, m/z): RT=0.268 min, m/z=107.0 [M+H]+.

Step 4: Synthesis of 1-(4-chloro-2-methoxyphenyl)-N-(2-(methoxy-d3)-2-methylpropyl)pyrido[3,4-d]pyridazin-4-amine

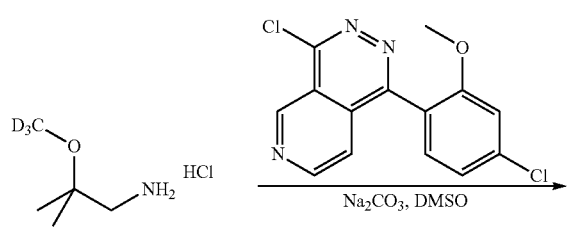

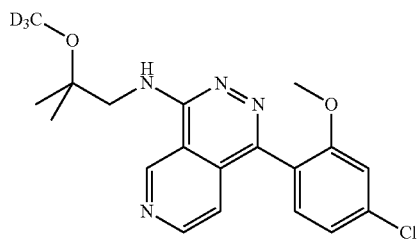

Into a 20 mL vial were added 2-(d3)methoxy-2-methylpropan-1-amine acid salt (104 mg, 0.98 mmol, 2.00 equiv), 4-chloro-1-(4-chloro-2-methoxyphenyl)pyrido[3,4-d]pyridazine (150 mg, 0.49 mmol, 1.00 equiv), Na$_2$CO$_3$ (259 mg, 2.45 mmol, 5.00 equiv) and DMSO (3 mL) at room temperature. The resulting mixture was stirred for 2h at 80° C. the reaction progress was monitored by LCMS. The resulting mixture was used in the next step directly without further purification. LCMS 110: (ES, m/z): RT=0.828 min, m/z=376.0[M+1]$^+$.

Step 5: Synthesis of 5-chloro-2-(4-{[2-(d3)methoxy-2-methylpropyl]amino}pyrido[3,4-d]pyridazin-1-yl)phenol (compound 99)

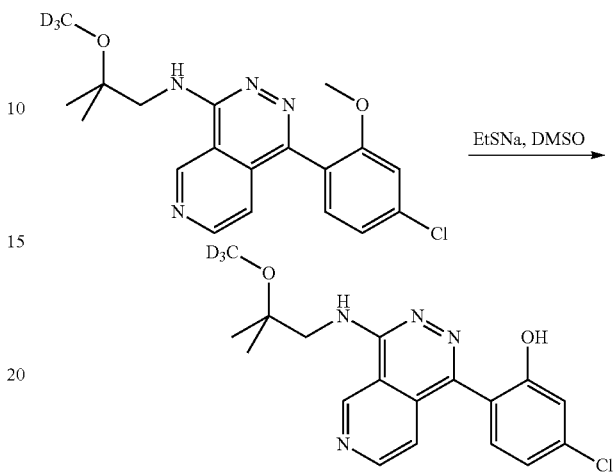

Into a 50 mL round-bottom flask were added the reaction mixture from VTT-2628-4, was added (ethylsulfanyl)sodium (179 mg, 2.13 mmol, 10.00 equiv) and DMSO (4 mL) at room temperature. The resulting mixture was stirred for 1h at 120° C. The reaction progress was monitored by LCMS. The resulting mixture was filtered, the filter cake was washed with MeOH (3×10 mL). The filtrate was concentrated under reduced pressure. The crude product (80 mg, purity=60% was purified by Prep-HPLC with the following conditions (2 #SHIMADZU (HPLC-01)): Column, XBridge Prep OBD C18 Column, 30*150 mm, 5 μm; mobile phase, Water (10 mmol/L NH4HCO3) and ACN (20% ACN up to 70% in 8 min); Detector, UV 254 nm. This resulted in 5-chloro-2-(4-{[2-(d3)methoxy-2-methylpropyl]amino}pyrido[3,4-d]pyridazin-1-yl)phenol (24.8 mg, yield=32.20%) as a yellow solid. LCMS: (ES, m/z): RT=1.266 min, m/z=362.0[M+1]$^+$. $^1$H NMR (400 MHz, Methanol-d4) δ 9.68 (s, 1H), 8.86 (d, J=5.7 Hz, 1H), 7.54-7.50 (m, 1H), 7.42-7.29 (m, 1H), 7.04 (d, J=7.1 Hz, 2H), 3.88 (s, 2H), 1.34 (s, 6H).

Example 8. $^1$H NMR Data

TABLE 2

$^1$H NMR Data

| Cmp. # | $^1$H NMR |
|---|---|
| 82 | $^1$H NMR (400 MHz, DMSO-d$_6$) δ 10.25 (s, 1H), 9.80 (d, J = 1.0 Hz, 1H), 8.87 (d, J = 5.6 Hz, 1H), 7.84 (t, J = 5.9 Hz, 1H), 7.39-7.25 (m, 2H), 7.03 (d, J = 7.7 Hz, 2H), 5.07 (s, 1H), 3.70 (d, J = 5.8 Hz, 2H), 1.23 (s, 6H). |
| 83 | $^1$H NMR (400 MHz, DMSO-d$_6$) δ 10.23 (s, 1H), 9.82 (s, 1H), 8.85 (d, J = 2.4 Hz, 1H), 7.68-7.65 (m, 1H), 7.36-7.29 (m, 2H), 7.04-7.02 (m, 2H), 3.80 (d, J = 6 Hz, 2H), 3.23 (s, 3H), 1.24 (s, 6H). |
| 84 | $^1$H NMR (400 MHz, DMSO-d$_6$) δ 9.81 (d, J = 5.6 Hz, 1H), 8.85 (d, J = 5.6 Hz, 1H), 7.57 (t, J = 6.0 Hz, 1H), 7.36 (d, J = 5.6 Hz, 1H), 7.27-7.25 (m, 1H), 6.59-6.56 (m, 2H), 3.79 (d, J = 2.4 Hz, 5H), 3.24 (s, 3H), 1.24 (s, 6H). |
| 85 | $^1$H NMR (400 MHz, DMSO-d$_6$) δ 9.81 (d, J = 0.9 Hz, 1H), 8.85 (d, J = 5.6 Hz, 1H), 7.62-7.55 (m, 1H), 7.36-7.30 (m, 1H), 7.21 (d, J = 7.6 Hz, 1H), 6.85-6.76 (m, 1H), 3.80 (d, J = 5.8 Hz, 2H), 3.24 (s, 3H), 2.34 (s, 3H), 1.25 (s, 6H). |

TABLE 2-continued

¹H NMR Data

| Cmp. # | ¹H NMR |
|---|---|
| 86 | ¹H NMR (400 MHz, DMSO-d$_6$) δ 10.22 (s, 1H), 9.83 (s, 1H), 8.86 (d, J = 5.6 Hz, 1H), 7.67 (s, 1H), 7.34-7.28 (m, 2H), 7.19-7.17 (m, 2H), 3.81 (d, J = 5.9 Hz, 2H), 3.24 (s, 3H), 1.25 (s, 6H). |
| 87 | ¹H NMR (400 MHz, DMSO-d$_6$) δ 10.44 (s, 1H), 9.85 (d, J = 1.0 Hz, 1H), 8.86 (d, J = 5.6 Hz, 1H), 7.73 (m, 1H), 7.57 (d, J = 7.7 Hz, 1H), 7.36-7.27 (m, 3H), 3.82 (d, J = 5.9 Hz, 2H), 3.24 (s, 3H), 1.25 (s, 6H). |
| 88 | ¹H NMR (400 MHz, DMSO-d$_6$) δ 10.39 (s, 1H), 9.83 (s, 1H), 8.87-8.85 (m, 1H), 7.67 (t, J = 6.0 Hz, 1H), 7.46 (d, J = 8.9 Hz, 1H), 7.30 (d, J = 5.6 Hz, 1H), 6.96 (d, J = 6.2 Hz, 2H), 3.81 (d, J = 5.8 Hz, 2H), 3.24 (s, 3H), 1.25 (d, J = 1.4 Hz, 6H). |
| 89 | ¹H NMR (400 MHz, DMSO-d$_6$) δ 9.82 (s, 1H), 8.87 (d, J = 5.6 Hz, 1H), 7.94 (d, J = 5.8 Hz, 1H), 7.43-7.27 (m, 2H), 7.04 (d, J = 7.1 Hz, 2H), 4.87-4.80 (m, 1H), 4.11-3.91 (m, 2H), 3.85-3.72 (m, 2H), 2.40-2.26 (m, 1H), 2.22-2.06 (m, 1H). |
| 90 | ¹H NMR (400 MHz, DMSO-d$_6$) δ 9.67 (s, 1H), 8.84 (d, J = 5.6 Hz, 1H), 7.94 (t, J = 5.3 Hz, 1H), 7.36-7.32 (m, 1H), 7.30 (d, J = 5.6 Hz, 1H), 7.05-7.00 (m, 2H), 4.45 (s, 1H), 3.82-3.63 (m, 2H), 1.94-1.78 (m, 2H), 1.22 (s, 6H). |
| 91 | ¹H NMR (400 MHz, DMSO-d$_6$) δ 10.23 (s, 1H), 9.74 (s, 1H), 8.86 (d, J = 5.6 Hz, 1H), 8.11 (s, 1H), 7.38-7.28 (m, 2H), 7.08-7.00 (m, 2H), 3.67-3.31 (m, 2H), 2.75-2.67 (m, 1H), 2.35-2.31 (m, 1H), 2.24-1.95 (m, 4H), 1.66-1.61 (m, 1H). |
| 92 | ¹H NMR (400 MHz, DMSO-d$_6$) δ 9.90 (s, 1H), 9.13 (dd, J = 5.5, 1.2 Hz, 1H), 7.68 (dd, J = 5.5, 1.0 Hz, 1H), 7.41 (d, J = 8.1 Hz, 1H), 7.14-7.06 (m, 2H), 4.05-3.90 (m, 2H), 3.87-3.79 (m, 1H), 3.77-3.73 (m, , 1H), 3.70 (d, J = 7.6 Hz, 2H), 2.98-2.83 (m, 1H), 2.27 (m, 1H), 1.90-1.78 (m, 1H). |
| 93 | ¹H NMR (400 MHz, Methanol-d$_4$) δ 9.72 (d, J = 4.0 Hz, 1H), 9.01 (dd, J = 5.6, 1.9 Hz, 1H), 7.64 (dd, J = 6.0, 2.2 Hz, 1H), 7.41 (dd, J = 8.0, 1.0 Hz, 1H), 7.14-7.07 (m, 2H), 4.22 (dd, J = 15.5, 2.8 Hz, 1H), 3.90-4.05 (m, 1H), 3.87-3.68 (m, 2H), 3.25 (d, J = 8.9 Hz, 1H), 3.14 (s, 3H), 2.50-2.30 (m, 1H), 2.25-1.95 (m, 3H). |
| 94 | ¹H NMR (400 MHz, DMSO-d6) δ 9.88 (s, 1H), 8.98 (d, J = 5.6 Hz, 1H), 7.52-7.32 (m, 2H), 7.07 (m, 2H), 4.20 (dd, J = 19.0, 2.5 Hz, 2H), 4.02-3.83 (m, 4H), 2.39-2.19 (m, 2H). |
| 95 | ¹H NMR (400 MHz, DMSO-d6) δ 9.73 (d, J = 1.0 Hz, 1H), 8.87 (d, J = 5.7 Hz, 1H), 7.52 (d, J = 5.7 Hz, 1H), 7.38 (d, J = 8.0 Hz, 1H), 7.05 (d, J = 8.0 Hz, 2H), 4.42-4.34 (m, 1H), 4.27-4.21 (m, 1H), 2.45-2.35 (m, 1H), 2.16-2.06 (m, 1H), 1.97-1.80 (m, 3H), 1.80-1.70 (m, 1H). |
| 96 | ¹H NMR (400 MHz, DMSO-d6) δ 9.90 (d, J = 0.9 Hz, 1H), 9.13 (d, J = 5.5 Hz, 1H), 7.67-7.65 (m, 1H), 7.40 (d, J = 8.1 Hz, 1H), 7.18-7.02 (m, 2H), 3.77 (s, 2H), 3.62 (s, 2H), 0.86-0.63 (m, 4H). |
| 97 | ¹H NMR (400 MHz, Methanol-d$_4$) δ 10.43-10.28 (m, 1H), 9.82 (s, 1H), 8.90-8.88 (m, 1H), 8.40-8.38 (m, 1H), 7.37-7.34 (m, 2H), 7.06-7.02 (m, 2H), 4.40-4.33 (m, 1H), 4.13-4.04 (m, 1H), 3.81-3.70 (m, 1H), 3.68-3.63 (m, 3H). |
| 98 | 1H NMR (400 MHz, Methanol-d$_4$) δ 10.24 (s, 1H), 9.83 (s, 1H), 8.85 (d, J = 5.6 Hz, 1H), 7.92 (d, J = 6.4 Hz, 1H), 7.38-7.32 (m, 1H), 7.32-7.27 (m, 1H), 7.07-7.00 (m, 2H), 4.82-4.72 (m, 1H), 2.88 (m, 1H), 2.73 (m, 1H), 2.64 (m, 1H), 2.50-2.48 (m, 1H), 2.41-2.34 (m, 1H), 2.32 (s, 3H), 2.02-1.89 (m, 1H). |
| 99 | ¹H NMR (400 MHz, DMSO-d6) δ 9.68 (s, 1H), 8.86 (d, J = 5.7 Hz, 1H), 7.54-7.50 (m, 1H), 7.42-7.29 (m, 1H), 7.04 (d, J = 7.1 Hz, 2H), 3.88 (s, 2H), 1.34 (s, 6H). |
| 100 | 1H NMR (400 MHz, Methanol-d$_4$) δ 9.69 (d, J = 1.1 Hz, 1H), 8.85 (d, J = 5.6 Hz, 1H), 7.52 (d, J = 5.6 Hz, 1H), 7.37 (d, J = 8.5 Hz, 1H), 7.06-7.00 (m, 2H), 3.71-3.61 (m, J = 9.7, 6.0 Hz, 1H), 3.59-3.49 (m, J = 9.6, 5.5 Hz, 1H), 3.44 (s, 3H), 1.42 (d, J = 6.7 Hz, 3H). |
| 101 | 1H NMR (400 MHz, Methanol-d$_4$) δ 9.67-9.62 (m, 1H), 8.87 (d, J = 5.7 Hz, 1H), 7.53-7.51 (m, 1H), 7.38 (d, J = 8.0 Hz, 1H), 7.06 (d, J = 8.5 Hz, 2H), 4.11-3.95 (m, 2H), 3.88-3.84 (m, J = 4.7 Hz, 1H), 3.82-3.67 (m, 2H), 3.11-3.08 (m, 1H), 2.86-2.83 (m, 1H), 2.43 (d, J = 1.5 Hz, 3H), 2.40-2.34 (m, 1H), 2.24-2.14 (m, 1H). |
| 102 | ¹H NMR (400 MHz, DMSO-d6) δ 10.25 (s, 1H), 9.83 (s, 1H), 8.89 (d, J = 5.6 Hz, 1H), 8.21 (t, J = 6.4 Hz, 1H), 7.39-7.32 (m, 2H), 7.05 (d, J = 7.2 Hz, 2H), 3.99 (d, J = 6.0 Hz, 2H), 1.47 (s, 6H). |
| 103 | ¹H NMR (400 MHz, DMSO-d6) δ 10.16 (s, 1H), 9.76 (s, 1H), 8.87 (d, J = 5.6 Hz, 1H), 8.49 (t, J = 5.7 Hz, 1H), 8.35 (d, J = 1.0 Hz, 1H), 8.07 (d, J = 1.0 Hz, 1H), 7.38-7.29 (m, 2H), 7.04 (d, J = 6.8 Hz, 2H), 4.77 (d, J = 5.5 Hz, 2H). |
| 104 | ¹H NMR (400 MHz, DMSO-d6) δ 10.24 (s, 1H), 9.79 (s, 1H), 8.88 (d, J = 5.6 Hz, 1H), 8.66 (t, J = 5.9 Hz, 1H), 7.38-7.23 (m, 5H), 7.08-6.99 (m, 3H), 4.89 (d, J = 5.9 Hz, 2H). |
| 105 | 1HNMR (400 MHz, CD3OD-d4) δ 9.71(s, 1H), 8.87-8.85 (d, J = 6.0 Hz, 1H), 7.53-7.51 (d, J = 6.0 Hz, 1H), 7.39-7.37 (d, J = 8.0 Hz, 1H), |

TABLE 2-continued

<sup>1</sup>H NMR Data

| Cmp. # | <sup>1</sup>H NMR |
|---|---|
| | 7.07-7.04 (m, 2H), 5.03-4.99 (m, 1H), 4.42-4.38 (m, 1H), 3.93-3.90 (m, 1H), 2.47-2.42 (m. 1H), 2.10-2.05 (m, 1H), 1.44 (s, 3H), 1.35 (s, 3H). |

Example 9. Biological Activity of the Compounds of the Present Disclosure

The biological activity of the compounds of the present disclosure was determined utilising the assay described herein.

Human PBMC NLRP3 Assay

Reagents: Human PBMCs (Normal): iXCells Cat #10HU-003; RPMI 1640 medium with GlutaMAX: ThermoFisher Cat #61870127 (Complete Media: 4.5 g/L D-glucose, 10% FBS, 100 mM NaPyr, 1% Pen/Strep, 10 mM HEPES and 0.05 mM of ®-mercaptoethanol; Assay Media: 4.5 g/L D-glucose, 100 mM NaPyr, 1% Pen/Strep, 10 mM HEPES and 0.05 mM of mercaptoethanol; 96-well V-bottom Plates: Costar Cat #3894; LPS (*E. coli* O26:B6): Sigma Cat #L2654, stock 5 mg/mL in PBS; ATP: Sigma Cat #A6419, prepared in a 250 mM stock in 1 M HEPES (adjusted to pH 7.4).

Human PBMC NLRP3 Assay: Cryopreserved PBMCs were rapidly thawed in a 37° C. water bath for 2 min. Cells were then centrifuged at 1200 RPM for 5 min and resuspended in ~50 mL of fresh RPMI 1640 Complete Medium. A count was undertaken using a hemocytometer and adjusted to $2.5 \times 10^5$ cells/mL. V-shaped 96-well plates were seeded with 200 µL of PMBCs ($5 \times 10^4$) per well and subsequently incubated overnight at 37° C. with 5% CO$_2$. Assay Media was then prepared containing 100 ng/ml of LPS. PBMCs were then centrifuged at 1,200 RPM for 5 min, serum containing media was aspirated, and 150 µL/well of Assay Media+LPS was immediately added. Assay Media without LPS was added in the untreated control wells. Cells were then primed with LPS for 4 h at 37° C. with 5% CO$_2$. A concentration response curve (CRC) was prepared of 1000× test compound in 100% DMSO. The CRC was then diluted 1:50 in Assay Media and then further diluted by 1:5× in Assay Media resulting in a final 4×CRC in 0.4% DMSO/Assay Media. 50 µL/well of 4× test compound CRC or vehicle (0.4% DMSO/Assay Media) was then transferred into each well and subsequently incubated for 30 min at 37° C. with 5% CO$_2$. Cells were stimulated by adding 4 µL of 250 mM ATP, using a 250 mM stock prepared in 1 M Hepes without further dilution (for a final concentration of 5 mM), for 1 h at 37° C. with 5% CO$_2$. Plates were then centrifuged at 1200 RPM for 5 min; and 50 µl of the media was transferred to a clean 96-well storage plate for cytokine measurements using the mesoscale platform, and stored at −80° C. until analyzed. Compounds were added 30 minutes before priming the cells with LPS when TNFα was required to be quantified in the cytokine panel to confirm selectivity.

Table 3 assigns each compound a code for potency in the Human PBMC NLRP3 Assay: A, B, C, or D. According to the code, A represents an IC$_{50}$ value <0.3 µM; B represents an IC$_{50}$ value ≥0.3 µM and <0.5 µM; C represents an IC$_{50}$ value ≥0.5 µM and <1.0 µM; D represents an IC$_{50}$ value ≥1.0 µM.

TABLE 3

| Cmp. # | PBMC IC$_{50}$ |
|---|---|
| 5 | B |
| 6 | D |
| 7 | A |
| 11 | A |
| 14 | B |
| 15 | D |
| 20 | B |
| 21 | B |
| 23 | C |
| 82 | A |
| 83 | A |
| 89 | A |
| 91 | A |
| 93 | A |

Human Whole Blood—NLRP3

Materials/Reagents:
  Blood collection tubes: Heparin lithium (green)
  U-bottom 96-well tissue culture, Falcon 353077
  HBSS for LPS, and compound dilutions: Gibco 24020-117
  Hepes 1M pH 7.4 for ATP dilution
  LPS, *E. coli* serotype O26:B6: Sigma L-2654
  Human IL-1b, IL-18 and TNFa MSD assay (Custom U-plex-human biomarker group 1)

Method

1. Blood is collected from healthy volunteers in heparin lithium tubes.
2. Plate 90 uL of pooled blood per well in 96-well U-bottom plates.
3. Add 5 uL of 20×LPS (20 ug/mL, final concentration of 1 ug/mL) and mix by gentle pipetting.
4. Incubate in TC incubator for 4.5 hours.
5. Add 5 uL of 20× compound or vehicle per well and mix by gentle pipetting.
   a. Compounds are diluted 1/50 in HBSS to prepare a 20× dilution curve in 2% DMSO
6. Incubate for 30 minutes in TC incubator with shaking (450 rpm).
7. Add 3.3 ul of 31×ATP (155 mM, final concentration of 5 mM) and mix by gentle pipetting
8. Incubate in TC incubator for 30 minutes with shaking (450 rpm).
9. Centrifuge plate for 10 minutes at 800×g and carefully remove ~70 uL of plasma. Freeze plasma if required.
10. Analyze human IL-1b with IL-1b MSD assay (K151TUK)
    a. If quantification of TNFα is included in the cytokine panel to confirm selectivity, compounds are added 30 minutes before the priming step with LPS (i.e. before step 3 described above)

Table 4 assigns each compound a code for potency in the Human whole blood (hWB) NLRP3 Assay: A, B, C, or D. According to the code, A represents an $IC_{50}$ value <0.3 μM; B represents an $IC_{50}$ value ≥0.3 μM and <0.5 μM; C represents an $IC_{50}$ value ≥0.5 μM and <1.0 μM; D represents an $IC_{50}$ value ≥1.0 μM.

TABLE 4

| Cmp. # | hWB $IC_{50}$ |
| --- | --- |
| 1 | A |
| 2 | A |
| 3 | B |
| 4 | B |
| 5 | A |
| 6 | A |
| 7 | D |
| 8 | A |
| 9 | C |
| 10 | D |
| 11 | A |
| 12 | B |
| 13 | A |
| 14 | C |
| 15 | C |
| 16 | C |
| 17 | D |
| 18 | A |
| 19 | B |
| 20 | B |
| 21 | A |
| 22 | C |
| 23 | D |
| 24 | A |

Example 10. Improvement in Potency for Certain Compounds

As the table below shows, significantly improved potency was observed for certain compounds. It is noted in the instant disclosure that fused bicyclic pyradine analogs exhibit ameliorated activities over monocyclic pyridazines as illustrated by the potencies in the PBMC assay:

TABLE 5

| Compound Structure | PBMC $IC_{50}$ (μM) |
| --- | --- |
| 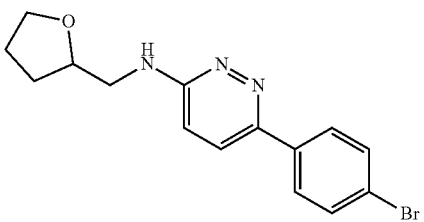 [SMILES: Brc1ccc(-c2ccc(NCC3CCCO3)nn2)cc1] | 3.8 |
| 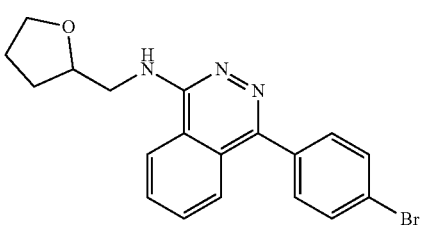 [SMILES: Brc1ccc(-c2nnc(NCC3CCCO3)c3ccccc23)cc1] | 0.19 |
| 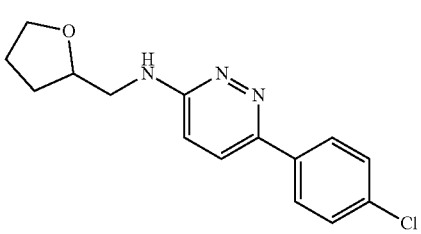 [SMILES: Clc1ccc(-c2ccc(NCC3CCCO3)nn2)cc1] | 64 |
| 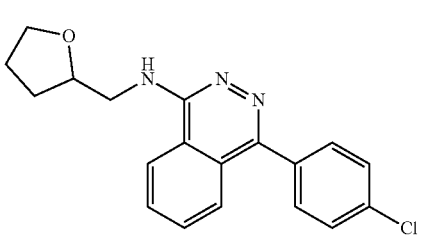 | 0.27 |

Furthermore, it is also noted that the specific pyridopyridazine regioisomer of the instant disclosure displays a potency improvement with respect to other regioisomers. Introducing the nitrogen atom within the bicyclic structure also allows for an advantageous protein binding that translates into improved whole blood potencies:

TABLE 6

| Compound Structure | PBMC $IC_{50}$ (μM) | hWB $IC_{50}$ (μM) |
| --- | --- | --- |
| 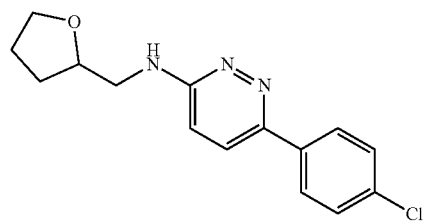 | 64 | >50 |

TABLE 6-continued

| Compound Structure | PBMC IC$_{50}$ (μM) | hWB IC$_{50}$ (μM) |
|---|---|---|
| 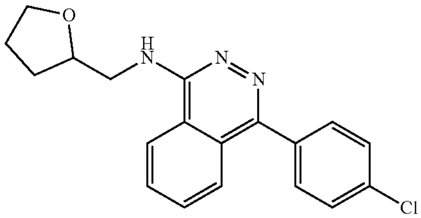 [SMILES: Clc1ccc(-c2nnc(NCC3CCCO3)c3ccccc23)cc1] | 0.27 | >50 |
| 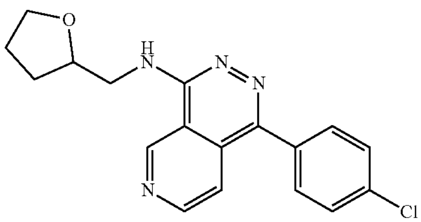 [SMILES: Clc1ccc(-c2nnc(NCC3CCCO3)c3ccccc23)cc1] | 0.36 | 8.6 |
| 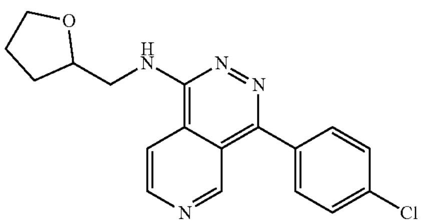 [SMILES: Clc1ccc(-c2nnc(NCC3CCCO3)c3ccncc23)cc1] | 2.9 | 42 |

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

What claimed is:

1. A method of treating a disease, condition, or disorder comprising administering to a human subject in need thereof a compound of Formula (II-h):

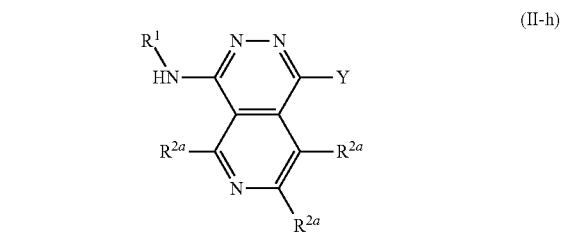

(II-h)

or a pharmaceutically acceptable salt thereof;
wherein:
R$^1$ is

Y is phenyl independently substituted with one, two, or three substituents selected from the group consisting of C$_1$-C$_6$ haloalkyl, halo, and —R$^4$OR$^5$;

$R^{2a}$ is hydrogen;

$R^4$ is a bond; and $R^5$ is hydrogen;

wherein treating is alleviation of an established symptom of said disease, condition or disorder in said human subject, and wherein said disease, condition or disorder is selected from the group consisting of a liver disease, a kidney disease, and a cardiovascular disease.

2. The method according to claim 1, wherein the disease, condition or disorder is a liver disease.

3. The method according to claim 1, wherein the disease, condition or disorder is a kidney disease.

4. The method according to claim 1, wherein the disease, condition or disorder is a cardiovascular disease.

5. The method according to claim 1, wherein $R^1$ is

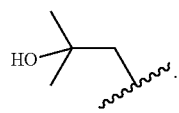

6. The method according to claim 5, wherein Y is phenyl independently substituted with one substituent selected from the group consisting of halo and —$R^4OR^5$.

7. The method according to claim 5, wherein Y is phenyl independently substituted with two substituents selected from the group consisting of halo and —$R^4OR^5$.

8. The method according to claim 7, wherein one of the two substituents is halo and the other substituent is —$R^4OR^5$.

9. The method according to claim 8, wherein the halo is chloro.

10. The method according to claim 9, wherein the disease, condition or disorder is a liver disease.

11. The method according to claim to 9, wherein the disease, condition or disorder is a kidney disease.

12. The method according to claim 9, wherein the disease, condition or disorder is a cardiovascular disease.

13. The method according to claim 1, wherein Y is phenyl substituted with one, two, or three substituents independently selected from the group consisting of $C_1$-$C_6$ haloalkyl, halo, and —$R^4OR^5$; wherein one substituent is halo.

14. The method according to claim 13, wherein the one substituent is chloro.

15. The method according to claim 14, wherein Y is phenyl further substituted with —$R^4OR^5$.

16. The method according to claim 5, wherein Y is phenyl substituted with one, two, or three substituents independently selected from the group consisting of $C_1$-$C_6$ haloalkyl, halo, and —$R^4OR^5$; wherein one substituent is halo.

17. The method according to claim 16, wherein the one substituent is chloro.

18. The method according to claim 17, wherein Y is phenyl further substituted with —$R^4OR^5$.

19. The method according to claim 1, wherein the compound is selected from the group consisting of:

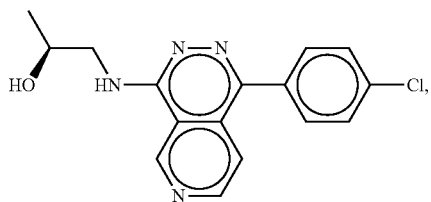
37

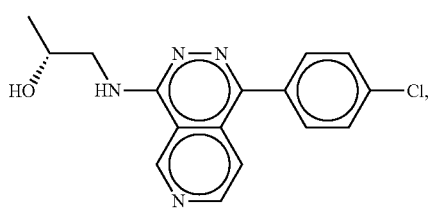
38

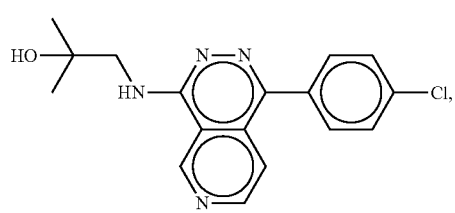
46

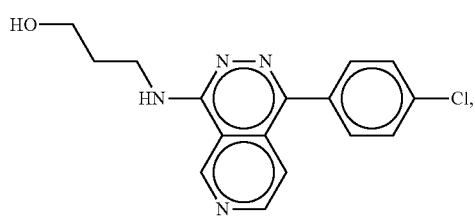
65

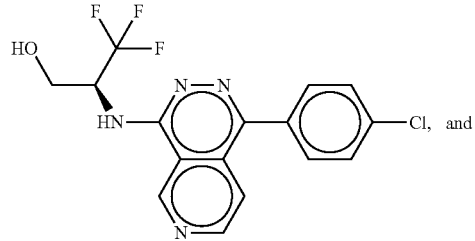
73

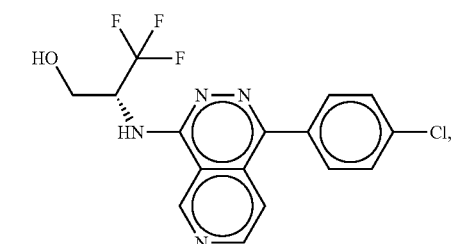
74 or a pharmaceutically acceptable salt of any of the foregoing.

20. The method according to claim 19, wherein the compound is of the formula:
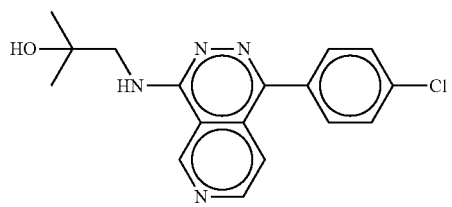
or a pharmaceutically acceptable salt thereof.
* * * * *

UNITED STATES PATENT AND TRADEMARK OFFICE
CERTIFICATE OF CORRECTION

| | | |
|---|---|---|
| PATENT NO. | : 12,351,578 B2 | Page 1 of 1 |
| APPLICATION NO. | : 17/974342 | |
| DATED | : July 8, 2025 | |
| INVENTOR(S) | : Stéphane Dorich et al. | |

It is certified that error appears in the above-identified patent and that said Letters Patent is hereby corrected as shown below:

In the Claims

At Column 121, Claim number 11, Line number 45, after "claim" delete "to"

Signed and Sealed this
Thirteenth Day of January, 2026

John A. Squires
*Director of the United States Patent and Trademark Office*